United States Patent
Pon

(10) Patent No.: US 12,409,336 B2
(45) Date of Patent: Sep. 9, 2025

(54) TREATMENT OF NON-OCULAR DISEASES/DISORDERS BY DELIVERY OF ELECTROMAGNETIC ENERGY TO OCULAR TISSUE

(71) Applicant: David Pon, San Francisco, CA (US)

(72) Inventor: David Pon, San Francisco, CA (US)

(73) Assignee: David Pon, San Francisco, CA (US)

( * ) Notice: Subject to any disclaimer, the term of this patent is extended or adjusted under 35 U.S.C. 154(b) by 0 days.

(21) Appl. No.: 18/705,350

(22) PCT Filed: Oct. 26, 2022

(86) PCT No.: PCT/US2022/047942
§ 371 (c)(1),
(2) Date: Apr. 26, 2024

(87) PCT Pub. No.: WO2023/076431
PCT Pub. Date: May 4, 2023

(65) Prior Publication Data
US 2024/0325777 A1    Oct. 3, 2024

Related U.S. Application Data

(60) Provisional application No. 63/271,856, filed on Oct. 26, 2021.

(51) Int. Cl.
*A61N 5/06*       (2006.01)
*A61N 5/067*     (2006.01)

(52) U.S. Cl.
CPC ............. *A61N 5/062* (2013.01); *A61N 5/067* (2021.08); *A61N 2005/0627* (2013.01);
(Continued)

(58) Field of Classification Search
CPC .................. A61N 5/062; A61N 5/0622; A61N 2005/0627; A61N 2005/0642;
(Continued)

(56) References Cited

U.S. PATENT DOCUMENTS 7,146,209 B2    12/2006    Gross et al.
8,506,558 B2    8/2013     Gertner et al.
(Continued)

OTHER PUBLICATIONS

International Search Report; International Searching Authority; International Application No. PCT/US2022/07942; Feb. 9, 2023; 2 pages.
(Continued)

*Primary Examiner* — Ahmed M Farah
(74) *Attorney, Agent, or Firm* — Taft Stettinius & Hollister LLP

(57) ABSTRACT

A process that provides preventative, protective and therapeutic treatment for non-ocular biological tissues or fluids includes applying a pulsed energy source to an ocular tissue or a target fluid to therapeutically or prophylactically treat the non-ocular tissue or fluid. A pulsed energy source having selected energy parameters may be applied to one or more ocular blood vessel of an individual who has a non-ocular disease/disorder. In accordance with one aspect of the present disclosure, it is determined that an individual has one or more non-ocular disease/disorder or other degenerative disease or is at a risk of developing such a disease, and pulsed electromagnetic energy is applied to an ocular tissue of the individual to therapeutically or prophylactically treat the non-ocular disease/disorder.

23 Claims, 2 Drawing Sheets

(52) U.S. Cl.
CPC ............... *A61N 2005/0642* (2013.01); *A61N 2005/0651* (2013.01); *A61N 2005/0659* (2013.01); *A61N 2005/0661* (2013.01); *A61N 2005/0663* (2013.01)

(58) Field of Classification Search
CPC ...... A61N 2005/0648; A61N 2005/065; A61N 2005/0651; A61N 2005/0658; A61N 2005/0659; A61N 2005/0661; A61N 2005/0662; A61N 2005/0663; A61N 5/067
USPC .................................. 607/88–91; 606/88–91
See application file for complete search history.

(56) References Cited

U.S. PATENT DOCUMENTS

| | | | |
|---|---|---|---|
| 10,898,708 | B2 | 1/2021 | Franco-Obregon et al. |
| 2001/0056293 | A1* | 12/2001 | Brainard ............ A61B 5/4848 607/88 |
| 2002/0183811 | A1* | 12/2002 | Irwin .................. A61N 5/0616 607/94 |
| 2007/0016074 | A1* | 1/2007 | Abreu ................. A61B 3/185 600/475 |
| 2009/0216299 | A1* | 8/2009 | Dantus ............... A61N 5/0616 385/27 |
| 2012/0041520 | A1* | 2/2012 | Colbaugh ........... A61N 5/0618 607/88 |
| 2017/0232269 | A1* | 8/2017 | Luttrull .................. A61N 2/02 601/3 |
| 2018/0264284 | A1* | 9/2018 | Alvarez .............. A61N 5/0618 |
| 2022/0023654 | A1 | 1/2022 | Carmeli et al. |

OTHER PUBLICATIONS

Written Opinion of the International Searching Authority; International Searching Authority; International Application No. PCT/US2022/047942; Feb. 9, 2023; 5 pages.

Frizziero et al.; Subthreshold Micropulse Laser Modulates Retinal Neuroinflammatory Biomarkers in Diabetic Macular Edema; Journal of Clinical Medicine, vol. 10, Jul. 15, 2021; pp. 1-10.

* cited by examiner

TREATMENT OF NON-OCULAR DISEASES/DISORDERS BY DELIVERY OF ELECTROMAGNETIC ENERGY TO OCULAR TISSUE

CROSS-REFERENCE TO RELATED APPLICATION

This application is a national stage entry under 35 U.S.C. § 371 of International Application No. PCT/US2022/04792, filed Oct. 26, 2022, which claims priority to U.S. Provisional Patent Application No. 63/271,856, which was filed Oct. 26, 2021, the entire content of each is incorporated by reference herein.

BACKGROUND

The present disclosure is generally directed to systems and processes for treating non-ocular diseases/disorders, peripheral and/or systemic disease(s)/injuries, and/or any sequelae thereof, such as diabetes mellitus, heart disease, neurodegenerative diseases such as Alzheimer's disease and multiple sclerosis, cancer and other disease states. More particularly, the present disclosure is directed to a process for treating non-ocular diseases/disorders by delivering pulsed electromagnetic energy to ocular tissue, which has a beneficial remote therapeutic effect on a non-ocular tissue.

A wide variety of diseases affecting humans and other mammals have long eluded effective treatments. While the ultimate goal of medical research is the eradication, or "cure," of disease, there are many diseases for which the underlying cause is unknown, and which either have no treatment or suboptimal treatment. Some of these diseases are either uniformly terminal in short-order, or constitute major public health problems due to increasing at-risk populations and chronicity leading to widespread increase in prevalence. Many such diseases are both chronic and progressive. A substantial proportion of medical care involves the treatment of symptoms to ease the effects of disease and/or to replace biological function that has been lost as a result of the disease. Even diseases for which effective treatments have been developed, however, are often characterized by differing results among patients that result from unique, individual characteristics of each person's genetic makeup that effect each person's individual response to a given treatment. This often results in differing responses and/or effectiveness of a treatment among any given patient population.

A disease is a disorder of biological structure or biological function. A great many diseases are caused when a healthy biological structure or a properly functioning biochemical process or cascade in a healthy person or other mammal is damaged or disrupted, such as, for example, as a result of aging, by invasion by an infectious agent; the unavailability of necessary molecular participants in a biochemical process (e.g., nutrients or other biochemical molecules) as a result of dehydration, a lack of proper nutrition, or genetic mutation; the presence of molecules that disrupt proper biochemical processes (e.g., toxins, inhibitors, etc.); and various combinations of these and/or other factors. Vast amounts of resources have been invested into research and development of medical technologies to prevent and/or treat diseases or the symptoms of diseases, including, for example, gene therapy, drug therapy, anti-inflammatory treatments, immunosuppressive treatments, stem cell transplantation and the like. Due to the complexity of biological systems, and the individualistic nature of different organisms as discussed above, however, such techniques have proven unsatisfactory, and often have adverse side effects and complications, such as ancillary damage and disruption to other important biological structures and processes, that make the treatment nearly as undesirable as the disease.

While living organisms have a capacity, through various mechanisms, to protect themselves against structural damage and disruption to biological functions, such as through immune responses to infectious agents, modulation of biochemical processes in response to nutrient deficiencies, flushing of toxins, repair of genetic mutations, and many others, these defensive mechanisms also can be disrupted or damaged, thus rendering the organism unable to withstand the disruption or repair the structure, resulting in imbalance which leads to a disease state.

A great need exists for technological advancements that enhance or improve the ability of a person or other mammal to resist or repair such damage or disruption to its biological structures and functions, thereby maintaining or restoring a healthy balanced state and preventing or recovering from disease. The present disclosure addresses this need.

SUMMARY

An ideal treatment for disease is to enhance or energize an organism's natural ability to protect itself from injury or disruption to its biological structures and processes, and its natural ability to heal. The present disclosure provides such a treatment. The treatment disclosed herein is physiologic, effective and well tolerated without significant adverse side-effects.

The present disclosure is based on the inventor's serendipitous discovery, while conducting research and development of new methods for diagnosing and treating age-related macular degeneration (AMD), that pulsed subthreshold low level laser/light therapy (LLLT) not only was highly effective to reverse the progression of wet AMD, to prevent the full transition of dry AMD to wet AMD, and to restore and improve vision to patients, but it also had surprising and substantial positive effects on other biological structures and functions remote from the patient's ocular tissues. This work therefore established that the delivery of pulsed electromagnetic energy to the patient's ocular tissues, and particularly the delivery of LLLT focused on the patient's ocular blood vessels, surprisingly produces remote (i.e., non-ocular) benefits and therapeutic effects. While not intending to be bound by any theory whereby the methods and systems described herein achieve their advantageous results, it is believed that the pulsed electromagnetic energy, delivered at low energy levels that produces no detectible injury to ocular tissues, stimulates the natural production of biological agents by the patient's own cells, or energizes molecules already existing within the patient's cells or body fluids, which then circulated or transferred or transported through the patient's bloodstream to other parts of patient's body, where they had beneficial and/or therapeutic effects.

The present disclosure is directed to systems and methods for preventing and/or treating non-ocular diseases, disorders and/or conditions, including for example and without limitation, cancers, such as, for example and without limitation, solid, soft tissue, and hematological malignancies (such as, for example and without limitation, multiple myeloma, breast, ovarian, colon, renal cell, thyroid cancers, head and neck cancer, squamous cell carcinoma and melanoma), breast cancer related lymphedema, heart disease, hypertension, metabolic/endocrine disorders, diabetes mellitus, diabetic foot ulcers, diabetic neuropathy, cerebrovascular disorders, spinal cord injuries, obesity, dyslipidemia, liver disease, renal disease, traumatic brain injury, dermatologic disorders (such as, for example and without limitation, acne vulgaris, alopecia and skin wrinkles), infections such as, for example and without limitation, fungal infections, drug-resistant infections, microbiome related disorders, body system disorder (including, for example, and without limitation, immunity, metabolic, obesity, inflammatory, cardiovascular and neurodegenerative disorders), immune/complement system disorders, dental disorders, oral mucositis, memory disorders, psychiatric disorders, musculoskeletal disorders such as, for example, and without limitation, carpal tunnel syndrome, rheumatoid arthritis, osteoarthritis, tendinopathy, shoulder injuries, muscle spasms, myofascitis, chronic joint disorders and fibromyalgia, bone disorders, osteoporosis, neurodegenerative diseases, such as, for example and without limitation, multiple sclerosis, Parkinson's disease, Alzheimer's disease and amyotrophic lateral sclerosis, excess subcutaneous adiposity, wound healing, poor exercise performance issues, sperm motility and velocity issues, chronic pain, such as, for example and without limitation, chronic neck and lower back pain, tendonitis, chronic joint disorders, temporomandibular joint pain-dysfunction syndrome, trigeminal neuralgia, postherpetic neuralgia, and diabetic neuropathy, inflammatory disorders (e.g., arthritis, gingivitis), pulmonary disorders, e.g. COVID-19/acute respiratory distress syndrome (ARDS)/cytokine storm, other degenerative aging disease or other systemic disorders (each of these diseases, disorders and/or conditions referred herein to as a "non-ocular disease/disorder" and collectively as "non-ocular diseases/disorders").

In accordance with one aspect of the present disclosure, it is determined that an individual has one or more non-ocular disease/disorder or is at a risk of developing such a non-ocular disease/disorder and, in response to such determination, pulsed electromagnetic energy is applied to at least one ocular blood vessel of the individual to prevent or treat the non-ocular disease/disorder. In certain preferred embodiments, the electromagnetic energy comprises one infrared and/or near infrared and/or visible wavelength or multiple infrared and/or near infrared and/or visible wavelengths (delivered simultaneously or sequentially) having a selected set of energy parameters selected from the group consisting of wavelength, duty cycle (e.g., continuous wave or pulsed in microseconds, nanoseconds, picoseconds, femtoseconds), power, irradiance, energy density, titration profile, beam profile, spot size, short pulse duration, short pulse interval and envelope on duration and envelope off intervals, repeat intervals and frequencies, pulse train frequencies, micropulse envelope duration, number and interval of treatment sessions, contact lens types and magnification, and delivery methods such as via slit lamp biomicroscope, indirect ophthalmoscope, or other apparatus. In one embodiment, he average temperature rise of the ocular blood vessel and surrounding tissue is maintained at or below a predetermined level so as to not permanently damage the surrounding tissue. For example, in representative embodiments in which no attempt is made to close blood vessels, the average temperature rise is controlled to a level that does not increase the temperature of the ocular blood vessel and surrounding tissue to a sustained temperature greater than 38° C., greater than 39° C., greater than 40° C., or greater than 41° C., but the temperature can be raised even higher, such as, for example, up to about 52° C. or even up to about 65° C. or greater depending on the individualized circumstances (e.g., in ocular disease, if complete ocular blood vessel closure or ocular tumor ablation is desired).

The numerous variable pulsed electromagnetic energy parameters may be precisely selected and applied, optionally in cycles, to the one or more ocular blood vessels in a localized high spatial concentration with low energy/surface area pattern to cause resonant, polaritonic or other favorable interactions within at least one molecule or atom in or around the blood vessel and/or the intraluminal blood components (e.g., cellular and/or serum components) flowing within the blood vessel. It may also biomodulate (via chromophores) at least one overlying retinal cell such as a retinal pigment epithelial cell and/or its secretome as the electromagnetic energy passes through to the blood vessel (s).

The pulsed energy parameters may be selected and applied to at least one blood vessel in stepped upward titration so as to have resonant, or polaritonic, or favorable interaction with at least one molecule or atom for quantized photonic energy delivery, transfer, or single-, two-, or multiple-photon absorption and/or non-absorptive instantaneous resonance enhanced second (or higher) order harmonic generation (SHG) at each stepped level of parameters with greater irradiance or fluence with off intervals between trains of pulses of split seconds to minutes to allow for sufficient cooling and to reverse immediately the stepwise increase if any tissue reaction is noted in real time by using direct contact lens stereoscopic visualization. The wavelength(s) utilized may vary and may include 400 to 2,900 nm, and even long infrared 10,600 ($CO^2$ laser) to 50,000 nm with the most commonly used wavelengths being red to near-infrared (600-1100 nm). The frequency of the pulsed electromagnetic energy may range from about 1 Hz to about $10^8$ megahertz (MHz), may have a duty cycle of from about 0.4% to about 50% or about 0.4% to about 100%, and may have a pulse train duration from about 10 to about 9000 milliseconds and short pulse duration from $10^{-15}$ to 1.0 seconds, from $10^{-15}$ to 60 seconds, or up to 30 minutes, with intra-envelope short pulse pulsing frequency from 1 to 10 GHz and envelope pulsing frequency (pulse repetition rate) from 1 to 10 GHz. For example Ti:sapphire type lasers can be tunable with wavelengths from 650 to 1100 nanometers, may produce ultrashort pulses as short as 10 femtoseconds ($10^{-15}$ seconds) and have pulse repetition frequencies as much as 90 MHz ($10^6$ Hz), and produce individual pulses in the picojoule to millijoule ($10^{-12}$ to $10^{-3}$) range and generate peak powers of 50 gigawatts ($10^9$ watts).

At least three families of non-tunable wavelength micropulse-capable lasers are available from the Iridex laser manufacturer: 532 nm, 577 nm and 810 nm. For example, if using the micropulse-capable Iridex Oculight Slx 810 nm laser model, the laser parameters are capable of wide variation for different conditions and purposes and the possible parameters also depend on type of delivery system and laser adapter (subject to change per the manufacturer): 810 nm infrared, flat top beam profile, 650 nm red diode beam with user-adjustable intensity up to, 1 mW maximum, coaxial with 810 nm beam, 125-500 μm spot size (prior 810 nm models had 75 μm spot size available; 50 μm spot size is not available on 810 nm models), 600-5000 μm spot sizes on large spot adapters, 0 mW, 50 mW-2000 mW power, up to 3000 mW power with G-probe adaptor, Exposure Duration: CW-Pulse: 10-9000 ms in 29 increments, LongPulse: 10 s-30 min in 26 increments, Exposure Interval: CW-Pulse 0 ms, 50-1000 ms in 11 increments and single pulse, MicroPulse® duration: 0.1-1.00 ms (on time), increments of 0.05 ms, MicroPulse® Interval: 1.0-10.0 ms (off time), increments of 0.10 ms, adjustable repeat interval between envelopes, MicroPulse® duty cycle: 5%, 10%, 15% presets but adjustable from 0.4% to 50%. The Iridex IQ 810 Laser System has similar functionality, but has MicroPulse® duration: 0.025-1.0 ms, MicroPulse® Interval: 1.0-9.50 ms, maximum power at 2000 mW. (Iridex 810 nm Infrared Solid-State Laser Family Brochure, Oculight SLx Operator Manual, SLA Operator Manual, and Iridex Corp., 2021). The 650 nm aiming laser beam is not pulsed, but for dual wavelength treatment, it is turned on and off during treatment and adjustable to a maximum output of 1 mW power (but usually set at less than one-half of maximum (providing at half maximum, e.g., a fluence of 0.02 J/cm$^2$ if at 500 μm spot size for 100 ms)). The 650 red diode beam and slit lamp illumination (with incoherent light spectrum of 400-750 nm) are kept at the smallest possible window dimensions and lowest illumination possible yet still allowing visualization and are on for not more than 120 seconds continuously at any one-time during treatment). They are both turned off during any nontreatment intervals, further allowing for recovery from temperature peaks. Furthermore, under control of an experienced surgeon, the effective fluence or irradiance can be reduced by using the micromanipulator control to "paint" the coaxial red and/or infrared (810 nm models) laser beams across a vessel and/or by defocusing the coaxial red diode beam toward the operator to allow for decreased fluence of the laser beams which are divergent, thus enlarging the effective spot size or by simply increasing the spot size on the slit lamp adaptor ("SLA").

Initially, the settings can vary and the 810 nm laser output can vary widely anywhere between 0.059 J/cm$^2$ to 4.200 J/cm$^2$ of fluence per train of micropulses in micropulse mode before the contact lens is accounted for. The parameters can certainly vary with guidance from various scans and any prior history of treatment parameters. In some embodiments, the laser is delivered via a slit lamp adapter via a fiberoptic line. In other embodiments, the laser may be delivered via an indirect ophthalmoscope. The laser parameter settings can vary the energy by some 5 orders of magnitude but can be set easily within the range for LLLT beneficial effects.

In some embodiments, for the first phase, the LLLT lasering technique is begun in the micropulse mode with automatic default setting at 15% as the laser is turned on. It is lowered at the beginning to 5% (or lower or higher) depending on the condition or combinations of conditions (e.g. degree of retinal/choroidal pigmentation, prior treatment responses, cancer diagnosis) being treated and may be varied gradually during the course of treatment. It is titrated and cycled through each step for effect and gradually increased from 5% to 15% from one to many trains of micropulses at each step (e.g. 5% intervals are preset steps at 5%, 10%, and 15%). The micropulse durations can be manually controlled and set or preset between 0.1 to 1.00 ms duration and the micropulse "off" interval set between 1.0 to 10.0 ms within the envelope. All laser settings may be gradually increased or decreased in stepwise fashion assuming there is no reaction visibly detected in real time with the stereoscopic contact lens. The duty cycle and various "off" intervals can be lowered or raised as needed as it may be adjusted manually. and the repetition frequency may also be changed to accommodate different diseases or disease stages with the guidance of any preoperative information. The SLA delivery spot size can be changed to a size of, for example, from 75 μm to 125 μm to 200 μm to 300 μm to 500 μm at any initial spot size with the standard SLA which is mounted on the biomicroscopic Haag-Streit or Zeiss slit lamp or similar slit lamp and the duration can adjusted from 1000 to 50 msec to lower or raise the irradiance or fluence even further especially if there appears to be more varying degrees of prominent pigmentation in the immediate area being treated. Initial treatment with repetitive subthreshold micropulsing laser can be beneficial in preventing scarring and its inhibitory effects on regeneration.

The effects of LLLT are not necessarily total dose dependent but instead depend on the rate at which light is delivered i.e. the power density. Research has demonstrated that the biological effects of LLLT can depend more on the power density of the light (mW/cm$^2$), than on the total energy density dose (J/cm$^2$). This would follow on a submolecular time field where photonic energy may be influencing the elementary processes of bond breaking and bond formation which are femtosecond ($10^{-15}$ sec.) to picosecond ($10^{-12}$ sec.) processes which are on the 6 to 9 orders of magnitude, or a million to a billion times faster than the fastest enzymatic turnover reactions which are in microseconds ($10^{-6}$ sec.) range, which are thousand times faster than action potential durations in milliseconds ($10^{-3}$ sec.) or a million to ten million times faster than protein folding or protein translation (1 to 10 seconds). So submolecular elementary processes or the fastest enzymatic turnover times are so fast that it may seem like a relative eternity to wait for a protein to fold to be translated. Thus, just waiting a second between two micropulse laser trains pulses is to the ultra-small quantum level dynamics like two separate treatment sessions. The enzyme turnover reaction is completed so fast relative to protein folding or translation that it is almost analogous to waiting a million years for your next birthday after one blows out your birthday candle.

As an example, there is a power density or irradiance of 147 W/cm$^2$ if the settings are at 200 microns spot size, 50 mW, at 500 Hz repetition with a Goldman 3 mirror contact lens of 1.08× effective magnification at the retinal surface. If using an envelope duration of 100 msec, at 5% micropulse, this would provide 0.74 J/cm$^2$ fluence per envelope, and if at 15% micropulse, this would provide 2.21 J/cm$^2$ fluence per envelope. However, the optimal dose-response relationship can be non-linear and may be dependent on multiple factors such the variable laser parameters such as wavelength/frequency (single or multiple) mode (micropulse, nanosecond pulse, continuous wave), delivery device (slit lamp/contact lens magnification, indirect ophthalmoscope), power, irradiance, fluence, micropulse duration, micropulse intervals, envelope duration, envelope "off" interval, micropulse frequency, repetition frequency of micropulse trains, spot size, number of applications, dosing frequency, frequency of treatment, treatment interval, retinal pigmentation, blood flow rate, focusing/defocusing, "painting" technique, presence of circulating photosensitive dyes, the severity of the underlying condition (s), as well as on the cell and tissue type. In methods contemplated by this disclosure, the laser parameters and methodologies can be adjusted to accommodate subthreshold fluences in such a way as to increase or decrease various biological effects while still not creating scarring. To reduce fluence, for example, the changes may involve numerous adjustments such as increasing the spot size, decreasing the short pulse duration, increasing the short pulse interval, decreasing the frequency of pulse envelopes, and the like. In one example, an envelope (milliseconds) of laser energy is divided into a train of short micropulses (microseconds) with sufficient "off" periods between micropulses to allow for cooling between micropulses to prevent any significant rise in temperature and/or damage to surrounding cells or tissue, which prevents scarring when performed in a true subthreshold manner.

The micromanipulator control can be used to "paint" the laser beam across a vessel. The pulsed electromagnetic energy may be applied to the ocular blood vessels at a given interval over a given period of time. For example, the pulsed electromagnetic energy may be applied to the ocular blood vessels for one treatment session of at least two spaced-apart one-minute to one-hour treatment session periods, which may be spaced apart by a period of from about one hour to about 120 days or more.

In one aspect of the disclosure, a method for ameliorating a non-ocular disease/disorder in a subject includes (i) selecting a patient based on a diagnosis for a non-ocular disease/disorder; and (ii) responding to the diagnosis for non-ocular disease/disorder by delivering pulsed electromagnetic energy to at least one ocular blood vessel of the patient to ameliorate at least one symptom or one sign of the non-ocular disease/disorder. In certain embodiments, the pulsed electromagnetic energy comprises electromagnetic energy having a frequency of from $10^0$ to $10^{18}$ Hz. In other embodiments, the pulsed electromagnetic energy comprises electromagnetic energy selected from infrared radiation, near infrared radiation, visible radiation and combinations thereof. In still other embodiments, the pulsed electromagnetic energy comprises ultraviolet radiation.

In certain embodiments, the at least one ocular blood vessel comprises a member selected from the group consisting of a retinal blood vessel, a choroidal blood vessel and combinations thereof. In certain embodiments, the retinal or choroidal blood vessel comprises a choroidal feeding vessel, a choroidal draining vessel, a choroidal arteriole, a choroidal venule, a retinal arteriole or a retinal venule. In other embodiments, the electromagnetic radiation irradiates a cell overlying the blood vessel, such as a retinal pigment epithelium cell or a neuroretinal cell (e.g. a photoreceptor cell), irradiates a molecule or an atom or an ion positioned within a cell or its extracellular matrix, and combinations thereof In various embodiments, the non-ocular disease/disorder is selected from the group consisting of cancers, such as, for example and without limitation, solid, soft tissue, and hematological malignancies (such as, for example and without limitation, multiple myeloma, breast, ovarian, colon, renal cell, thyroid cancers, head and neck cancer, squamous cell carcinoma and melanoma), breast cancer related lymphedema, heart disease, hypertension, metabolic/endocrine disorders, diabetes mellitus, diabetic foot ulcers, diabetic neuropathy, cerebrovascular disorders, spinal cord injuries, obesity, dyslipidemia, liver disease, renal disease, traumatic brain injury, dermatologic disorders (such as, for example and without limitation, acne vulgaris, alopecia and skin wrinkles), infections such as, for example and without limitation, fungal infections, onychomycosis, drug-resistant infections, microbiome related disorders, body system disorders (including, for example, and without limitation, immunity, metabolic, obesity, inflammatory, cardiovascular and neurodegenerative disorders), immune/complement system disorders, dental disorders, oral mucositis, memory disorders, psychiatric disorders, musculoskeletal disorders such as, for example, and without limitation, carpal tunnel syndrome, rheumatoid arthritis, osteoarthritis, tendinopathy, shoulder injuries, muscle spasms, myofascitis, chronic joint disorders and fibromyalgia, bone disorders, osteoporosis, neurodegenerative diseases, such as, for example and without limitation, multiple sclerosis, Parkinson's disease, Alzheimer's disease and amyotrophic lateral sclerosis, excess subcutaneous adiposity, wound healing, poor exercise performance issues, sperm motility and velocity issues, chronic pain, such as, for example and without limitation, chronic neck and lower back pain, tendonitis, chronic joint disorders, temporomandibular joint pain-dysfunction syndrome, trigeminal neuralgia, postherpetic neuralgia, and diabetic neuropathy, inflammatory disorders (e.g., arthritis, gingivitis), pulmonary disorders, e.g. COVID-19/acute respiratory distress syndrome (ARDS)/cytokine storm, other degenerative aging disease or other systemic disorders.

In certain embodiments, the pulsed electromagnetic energy comprises a pulsed low level laser/light therapy (LLLT) treatment. The pulsed LLLT treatment may have predetermined energy parameters selected from the group consisting of one infrared and/or near infrared and/or visible wavelength or multiple infrared and/or near infrared and/or visible wavelengths (delivered simultaneously or sequentially) having selected energy parameters, including wavelength, duty cycle, power, irradiance, energy density, titration profile, beam profile, spot size, short pulse and envelope on and off intervals, repeat intervals and frequencies, pulse train frequencies, micropulse envelope duration, number and interval of treatment sessions, contact lens types and magnification. In certain embodiments, the pulsed energy parameters are selected and applied to the ocular blood vessel to cause resonant interactions within biomolecules within and/or around the ocular blood vessel. In certain embodiments, the pulsed LLLT treatment comprises stimulating the ocular blood vessel with a sub-threshold laser.

In certain embodiments, the electromagnetic energy has a wavelength of from about 380 nm to about 10600 nm. In other embodiments, the electromagnetic energy has a wavelength of from about 700 nm to about 2900 nm. In still other embodiments, the electromagnetic energy comprises a first radiation component having a first wavelength of from about 380 nm to about 700 nm and a second radiation component have a second wavelength of from about 700 nm to about 1000 nm. In yet other embodiments, the first wavelength is from about 625 to about 700 nm and the second wavelength is from about 700 to about 900 nm. In still yet other embodiments, the first wavelength is about 650 nm and the second wavelength is about 810 nm. In yet other embodiments, additional wavelengths beyond the second can also vary in a similar fashion over different ranges from about 193 nm to about 1 mm.

In certain embodiments, the laser treatment comprises a duty cycle of from about 0.4% to about 50%, the laser treatment comprises a power of from about 0.5 mW to about 2000 mW, the laser treatment comprises an irradiance of from about 0.015 W/cm$^2$ to about 42,000 W/cm$^2$, the laser treatment comprises an energy density of from about 0.024 J/cm$^2$ to about 4,200 J/cm$^2$ per envelope pulse, spot size(s) of from about 50 microns to about 500 microns and/or the laser treatment comprises an envelope pulse duration of no greater than about 200 ms or a micropulse duration of no greater than about 1000 μsec.

The laser may be administered as a micropulse, such as, for example, a micropulse having a duration of from about 100 μsec to about 1000 μsec, as diagrammatically shown in FIG. 1. In other embodiments, the laser is administered as a nanopulse, such as, for example, a nanopulse having a duration of from about 1 nanosecond to about 100,000 nanoseconds. In other embodiments, the laser is administered as a picopulse, such as, for example, a picopulse having a duration of from about 1 picosecond to about 100,000 picoseconds. In other embodiments, the laser is administered as a femtopulse, such as, for example, a femtopulse having a duration of from about 1 femtosecond to about 100,000 femtoseconds.

In some embodiments, the method includes, before delivering the pulsed electromagnetic energy, injecting a dye intravenously into the subject. For example and without limitation, a dye or photoacceptor compound or substance may be selected from the group consisting of fluorescein, indocyanine green, verteporfin and derivatives thereof, or selected from the group consisting of other photoactive compounds, biologic compounds, cells (including stem cells), molecules, atoms and nanoparticles thereof.

In some embodiments of the method, the pulsed electromagnetic energy is delivered in a first session in which pulsed electromagnetic energy is delivered to a plurality of discreet ocular blood vessel sites. For example, the plurality of discreet ocular blood vessel sites can include at least 2, at least 3, at least 4, at least 5 or at least 6 discreet ocular blood vessel sites. In other embodiments, the method further includes one or more additional sessions after the first session, each of the first session and the one or more additional sessions separated from one another by a time period of from about 1 minute to about 120 days.

These and other embodiments, forms, features, and aspects of the disclosure will become more apparent through reference to the following description and the claims. This summary is not intended to identify key or essential features of the claimed subject matter, nor is it intended to be used to limit the scope of the claimed subject matter. Furthermore, it is to be understood that the features of the various embodiments described herein are not mutually exclusive and can exist in various combinations and permutations.

DETAILED DESCRIPTION

Figures 1, 2:
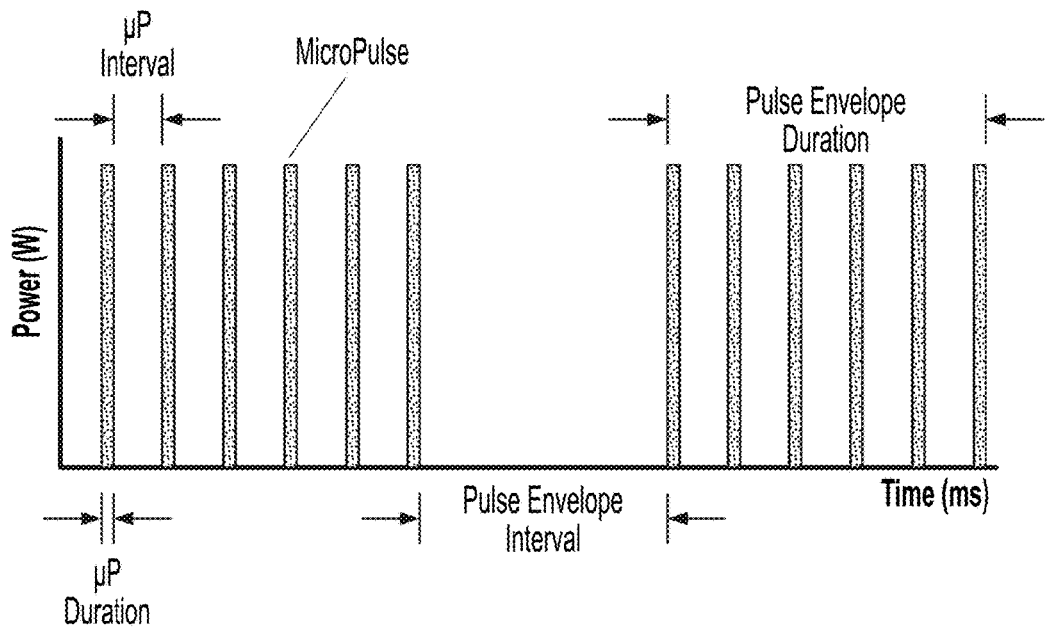
FIG. 1 is a diagram obtained from Oculight® SLx Operator Manual, Iridex Corporation, depicting how MicroPulse (μP) delivers laser energy in a burst of very short pulses and separating intervals. Both MicroPulse Duration and MicroPulse interval may be adjusted or selected from three present duty cycle values in the SLx instrument. Duty cycle refers to the percentage of time the treatment laser is activated during each pulse; duty cycle is calculated according to the formula shown in FIG. 1.
FIG. 2 is a diagram showing the orders of magnitude in timescales of multiple biological processes, represented as characteristic timescales extracted from the literature for exponentially growing E. coli and HeLa cells at 37° C. (see BioNumbers database). Numerical values should only serve as "rule of thumb" values. For example, the half-life of metabolites (turnover time of the metabolite pool) spans over 3 orders of magnitude. Some processes are shown only in one of the cell types yet are relevant to both. (Shamir M, Bar-On Y, Phillips R, Milo R. SnapShot: Timescales in Cell Biology. Cell 2016 March; 164(6):1302-1302.e1. DOI: 10.1016/j.cell.2016.02.058. PMID: 26967295.).

In general, this disclosure involves processes and systems that provide preventative, protective and therapeutic treatment for biological tissues or fluids having a non-ocular disease/disorder or at a risk of having a non-ocular disease/disorder. More particularly, the present disclosure is directed to systems and methods for the treatment of subjects having a non-ocular disease/disorder, such as cancers, such as, for example and without limitation, solid, soft tissue, and hematological malignancies (such as, for example and without limitation, multiple myeloma, breast, ovarian, colon, renal cell, thyroid cancers, head and neck cancer, squamous cell carcinoma and melanoma), breast cancer related lymphedema, heart disease, hypertension, metabolic/endocrine disorders, diabetes mellitus, diabetic foot ulcers, diabetic neuropathy, cerebrovascular disorders, spinal cord injuries, obesity, dyslipidemia, liver disease, renal disease, traumatic brain injury, dermatologic disorders (such as, for example and without limitation, acne vulgaris, alopecia and skin wrinkles), infections such as, for example and without limitation, fungal infections, onychomycosis, drug-resistant infections, microbiome related disorders, body system disorders (including, for example, and without limitation, immunity, metabolic, obesity, inflammatory, cardiovascular and neurodegenerative disorders), immune/complement system disorders, dental disorders, oral mucositis, memory disorders, psychiatric disorders, musculoskeletal disorders such as, for example, and without limitation, carpal tunnel syndrome, rheumatoid arthritis, osteoarthritis, tendinopathy, shoulder injuries, muscle spasms, myofascitis, chronic joint disorders and fibromyalgia, bone disorders, osteoporosis, neurodegenerative diseases, such as, for example and without limitation, multiple sclerosis, Parkinson's disease, Alzheimer's disease and amyotrophic lateral sclerosis, excess subcutaneous adiposity, wound healing, poor exercise performance issues, sperm motility and velocity issues, chronic pain, such as, for example and without limitation, chronic neck and lower back pain, tendonitis, chronic joint disorders, temporomandibular joint pain-dysfunction syndrome, trigeminal neuralgia, postherpetic neuralgia, and diabetic neuropathy, inflammatory disorders (e.g., arthritis, gingivitis), pulmonary disorders, e.g. COVID-19/acute respiratory distress syndrome (ARDS)/cytokine storm, other degenerative aging disease, other systemic disorders and other non-ocular diseases/disorders.

Although the concepts of the present disclosure are susceptible to various modifications and alternative forms, specific embodiments are shown by way of example and described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims. References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should be further appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible subranges as well as all individual numerical values within that range unless the context clearly dictates otherwise. For example, description of a range such as from 1 to 6 should be considered to have specifically disclosed subranges such as from 1 to 3, from 1.5 to 4, from 1 to 5.23, from 2 to 4, from 2.7 to 6, from 3.65 to 6 etc., as well as individual values within that range, for example, 1.1, 2, 2.3, 4.62, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes", "comprises", "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C).

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Definitions

By "ameliorate" is meant decrease, suppress, attenuate, diminish, arrest, or stabilize the development or progression of a disease or decrease, suppress, attenuate, diminish or arrest one or more symptoms of a disease.

By "hematopoietic stem cell" is meant a bone marrow derived cell, mesenchymal stem cell, umbilical cord derived stem cell or other potential types of stem cells such as an iPS (induced pluripotent stem cell) capable of giving rise to one or more differentiated cells of the hematopoietic lineage.

By "hematopoietic stem cell mobilization" is meant increasing the number of bone marrow derived stem cells, mesenchymal stem cells, umbilical cord derived stem cells or other potential types of stem cells such as iPS (induced pluripotent stem cells) available for recruitment to an organ or tissue in need thereof.

By "non-ocular disease/disorder" is meant a pathology effecting the normal function of a cell, tissue or organ other than those of the eyeball itself.

By "ocular disease or disorder" is meant a pathology effecting the normal function of the eyeball.

By "recruit" is meant attract for incorporation into a tissue.

By "reduces" or "increases" is meant a negative or positive alteration, respectively, of at least 1%, 5%, 10%, 25%, 50%, 75%, 100% or (in the case of an increase)$^{200}$%.

By "regenerating" a cell, tissue or organ is meant increasing the number, survival, or proliferation of cells, including cells in a tissue or organ.

By "repairing" is meant ameliorating injury or damage to a cell, tissue or organ, including injury or damage caused by cell death.

By "stem cell" is meant a progenitor cell capable of giving rise to one or more differentiated cell types.

By "subject" is meant a mammal, including, but not limited to, a human or non-human mammal, such as a bovine, equine, canine, ovine, or feline.

By "subthreshold laser" is meant a laser therapy that does not induce a lesion that is detectable in the retina during or following treatment, even by color photographs or fluorescein angiography or fundus autofluorescence or optical coherence tomography ("OCT"). A lesion is "undetectable" where little or no intraoperative visible tissue reaction is present or where little or no cell death (e.g., less than 10%, 5%, 2.5%, 1% of cells in treated tissue die or undergo apoptosis) due to laser treatment.

As used herein, the terms "treat," "treating," "treatment," and the like refer to reducing or ameliorating a disorder and/or symptoms associated therewith and may include prevention of progression. It will be appreciated that, although not precluded, treating a disorder or condition does not require that the disorder, condition or symptoms 'associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The present inventor, David Pon (referred to herein as "Dr. Pon"), previously developed ground-breaking and cutting-edge procedures for diagnosing and treating age-related macular degeneration (AMD) during the course of treating thousands of patients as a licensed board-certified fellowship-trained ophthalmologist/retinal specialist. While such procedures produced substantial positive results, they were not immediately accepted by the medical community. More recently, however, further research by others has continued to elucidate these significant advances and now a substantial body of literature includes data that confirms the benefits and principles of those ground-breaking procedures, which are described briefly below.

Background to Dr. Pon's Early Discoveries

The eye is a very functionally sensitive organ. There are a number of diseases that affect the retina that share underlying etiologic mechanisms and pathways that have been identified in many other chronic progressive diseases. In the developed world, age-related macular degeneration (AMD) is the leading cause of central blindness. "The projected number of people with age-related macular degeneration in 2020 is 196 million . . . increasing to 288 million in 2040 . . . " (Wong W L, Su X, Li X, et al. Global prevalence of age-related macular degeneration and disease burden projection for 2020 and 2040: a systematic review and meta-analysis. Lancet Glob Health. 2014; 2(2):e106-e116.). Despite a spectrum of overlapping phenotypic expressions, AMD has classically been divided into two major phenotypic subtypes referred to commonly as wet or neovascular AMD and dry AMD. "There are two types of AMD: dry (atrophic) and wet (neovascular or exudative). Most AMD starts as the dry type and in 10-20% of individuals, it progresses to the wet type. Age-related macular degeneration is always bilateral . . . " (Mogk L G, Duffy M A. Age Related Macular Degeneration. VisionAware.org. https://visonaware.org/your-eye-condition/age-related-macular-degeneration-amd/wet-and-dry-amd/. Accessed Jan. 24, 2022.). These conditions are at opposing ends of the spectrum of phenotypic AMD expression and both can progress to advanced late forms (central geographic atrophy in dry AMD and neovascularization with scarring in wet AMD) that can lead to the same result of permanent central vision loss. All AMD first begins as dry and most people have this slowly progressive dry phenotypic expression of AMD that can, for unclear reasons, convert into the less common but more rapidly progressive late neovascular phenotype. The AMD dry/wet spectrum has these two main forms but "Any stage of dry AMD can turn into wet AMD . . . " (NEI [National Eye Institute], NIH [National Institutes of Health]. "Age-Related macular Degeneration (AMD). Jun. 22, 2021. https://www.nei.nih.gov/learn-about-eye-health/eye-conditions-and-diseases/age-related-macular-degeneraion. Accessed Jul. 31, 2022.). "Neovascular age-related macular degeneration (exudative or wet AMD) is . . . characterized by neovascularization . . . " (Pugazhendhi, A.; Hubbell, M.; Jairam, P.; Ambati, B. Neovascular Macular Degeneration: A Review of Etiology, Risk Factors, and Recent Advances in Research and Therapy. *Int. J. Mol. Sci.* 2021, 22, 1170.). Neovascular AMD (nAMD) accounts for the great majority (80-90%) of permanent visual loss from AMD. Neovascular AMD usually causes faster vision loss by damage to the macula, the central part of the retina that controls good, sharp straight-ahead and reading vision. Neovascular AMD occurs when abnormal, leaky blood vessels develop in the back of the eye, a process variously referred to as "choroidal neovascularization" ("CMV"), subretinal neovascularization ("SRNVM") or macular neovascularization ("MNV"), and cause damage to the macula. This CNV or MNV is responsible for significant loss of central vision. In abnormal choroidal neovascularization, new vessels grow from the choroid into the subretinal space. Retinas at higher risk for choroidal neovascularization may have the presence of multiple or large soft drusen and/or pigmentary changes and/or genetic abnormalities. Vascular endothelial growth factor (VEGF), a hypoxia-regulated protein, plays a major role in the mechanisms leading to choroidal neovascularization.

Many Cases of Clinically Diagnosed "Dry" AMD are Actually Misdiagnosed "Wet" AMD.

The great importance of early diagnosis and treatment was underscored by the past research documenting that over half of eyes with wet AMD were clinically misdiagnosed as dry AMD, as shown by post-mortem histopathology (Heiferman, Michael J. and Fawzi, Amani A. Progression of subclinical choroidal neovascularization in age-related macular degeneration. PLoS ONE 2019:14(6): e0217805.) (Green W R and Key S N. Senile Macular Degeneration: A Histopathologic Study. *Tr. Am. Ophthal. Soc.* 1977:77:180-254. "Over half of the [post-mortem AMD] eyes (97 of 172, 56.3%) had neovascularization . . . ") (Sarks S H, "New vessel formation beneath the retinal pigment epithelium in senile eyes," *Brit J Ophthal*, 1973, 57: 951-965, 951, 963, 965. Clinically unsuspected MNV occurred in post-mortem eyes with a clinical misdiagnosis of dry AMD in 56.7%.). Recent post-mortem studies scientifically confirm that even early "dry" AMD at stage 1-2 (of nine-step AREDS) or the equivalent stage 2A (of 5-step CARMS) AMD classification, can have "subclinical" histopathologic choroidal neovascularization (CNV) with neovascular buds classically "extending through a break in Bruch's membrane." (Seddon J M, McLeod D S, Bhutto I A, et al. Histopathological Insights Into Choroidal Vascular Loss in Clinically Documented Cases of Age-Related Macular Degeneration. *JAMA Ophthalmol.* 2016; 134(11):1272-1280. doi:10.1001/jamaophthalmol.2016.3519. PMID: 27657855; PMCID: PMC6014730.) (Lutty G A, McLeod D S, Bhutto I A, Edwards M M, Seddon J M. Choriocapillaris dropout in early age-related macular degeneration. Exp Eye Res. 2020 March; 192:107939. doi: 10.1016/j.exer.2020.107939. Epub 2020 Jan. 24. PMID: 31987759; PMCID: PMC7216757.). "[E]arly choroidal neovascularization formations" have been histopathologically identified associated with areas of submacular choriocapillaris loss in early "dry" AMD (stage 2A, CARMS) (Lutty et al, 2020). "The onset of nAMD may be subtle and evident to neither patient nor physician . . . . While the affected area in some eyes was quite extensive histologically, these changes may not be detectable clinically using standard in vivo imaging." (Lutty et al, 2020) (emphasis added).

Clinically unsuspected choroidal neovascularization CNV occurred in post-mortem eyes clinically misdiagnosed as dry AMD in 56.7% (Sarks, 1973). "Over half of the [post-mortem AMD] eyes (97 of 172, 56.3%) had neovascularization . . . " (Green and Key, 1977). This scientific histopathologic evidence showed that wet AMD was underdiagnosed even when fluorescein angiography was available and that "Histopathologic specimens of eyes with clinically diagnosed dry AMD have shown newly-formed blood vessels invading into the subretinal space . . . [hence] subclinical choroidal neovascularization . . . ICG [indocyanine green][studies] further supported this . . . [and] eyes with these ICG findings are at higher risk of . . . late AMD." (Heiferman and Fawzi, 2019) (Green and Key, 1977) (Sarks, 1973). " . . . [T]he fundus details corresponding to clinically unsuspected subretinal neovascularization have not been fully described . . . . Small new vessels may remain clinically unsuspected . . . 67 percent of initially avascular lesions contained new vessels after an average follow-up period of 10 months . . . Subretinal neovascularization is a relatively common accompaniment of various manifestations of senile macular degeneration . . . " (Sarks, 1973). Further evidence is seen in "histopathologic studies of autopsy eyes with presumed nonexudative AMD [that] have identified subclinical fibrovascular tissue [from CNV] beneath the RPE in these eyes . . . " (Green W R, McDonnell P J, Yeo J H. Pathologic features of senile macular degeneration. *Ophthalmology.* 1985 May; 92(5):615-27. PMID: 2409504.) (Spraul C W, Grossniklaus H E. Characteristics of Drusen and Bruch's membrane in postmortem eyes with age-related macular degeneration. *Arch Ophthalmol.* 1997 February; 115(2):267-73. doi: 10.1001/archopht.1997.01100150269022. PMID: 9046265.). (Roisman L, Zhang Q, Wang R K, Gregori G, Zhang A, Chen C L, Durbin M K, An L, Stetson P F, Robbins G, Miller A, Zheng F, Rosenfeld P J. Optical Coherence Tomography Angiography of Asymptomatic Neovascularization in Intermediate Age-Related Macular Degeneration. *Ophthalmology.* 2016 June; 123(6):1309-19, 1311, 1314-5 doi: 10.1016/j.ophtha.2016.01.044. Epub 2016 Feb. 12. PMID:26876696; PMCID: PMC5120960.) The pathologic findings demonstrate nAMD may be much more prevalent than commonly thought. Furthermore, the development of "subclinical" MNV can be interpreted to "identif[y] as a positive conversion" endpoint in research for prophylactic clinical trials for neovascular AMD (Mendonca L S M, Levine E S, Waheed N K. Can the Onset of Neovascular Age-Related Macular Degeneration Be an Acceptable Endpoint for Prophylactic Clinical Trials?Ophthalmologica. 2021; 244(5):379-386. doi: 10.1159/000513083. Epub 2020 Nov. 16. PMID: 33197919.). Therefore, previous commonly utilized diagnostic techniques for nAMD were unable to identify a multitude of cases in which early intervention could be potentially sight-saving and more beneficial in improving vision.

New Technology Identifies a "Whole New Category" Of"Subclinical" Neovascular AMD.

The newer technology of optical coherence tomography-angiography ("OCT-A", FDA cleared late 2016) has now enabled the identification of a "whole new category" of AMD termed as "subclinical" neovascular AMD, which was previously undetectable except by time- and labor-intensive ICG angiography. Conventional examination, fluorescein angiography ("FA"), OCT, and color fundus photography ("CFP") were not able to detect this "new category" of neovascular AMD. The capabilities of the newer OCT-A technology or the seldom utilized and expensive indocyanine green ("ICG") technology are required to identify this transitional "subclinical" phase of the AMD spectrum between "dry" and "wet" AMD.

Furthermore, "Early detection of CNV and early management of exudative AMD have been shown to be associated with better visual acuity outcomes in patients who convert to clinically significant exudative AMD (Ho A C, Albini T A, Brown D M, Boyer D S, Regillo C D, Heier J S. The Potential Importance of Detection of Neovascular Age-Related Macular Degeneration When Visual Acuity Is Relatively Good. JAMA Ophthalmol. 2017 Mar. 1; 135(3):268-273. doi: 10.1001/jamaophthalmol.2016.5314. PMID: 28114653.). "It is now well accepted that baseline VA is one of the strongest predictors of long-term vision outcomes . . . delaying treatment is a predictor of worse VA outcomes . . . " (Ho A C, Kleinman D M, Lum F C, Heier J S, Lindstrom R L, Orr S C, Chang G C, Smith E L, Pollack J S. Baseline Visual Acuity at Wet AMD Diagnosis Predicts Long-Term Vision Outcomes: An Analysis of the IRIS Registry. Ophthalmic Surg Lasers Imaging Retina. 2020 Nov. 1; 51(11):633-639. doi: 10.3928/23258160-20201104-05. PMID: 33231696.). Indocyanine green angiography ("ICGA") is deemed the gold standard when assessing for the presence of type 1 neovascularization . . . Studies using ICG videography on patients with non-exudative AMD demonstrated that subclinical neovascularization could occur . . . However, it is still not clear at which point the MNVs arise in the evolution of drusen and pigment epithelial detachments . . . neovascularization may be present as early as in drusen . . . OCT alone is insufficient for its detection. Furthermore, vascularized drusen could not be detected using FA or CFP . . . [but] these lesions may be visible on ICG [angiography](Querques G, Souied E H. Vascularized Drusen: Slowly Progressive Type 1 Neovascularization Mimicking Drusenoid Retinal Pigment Epithelium Elevation. Retina. 2015 December; 35(12):2433-9. doi: 10.1097/IAE.0000000000000761. PMID: 26418449.) . . . In all instances, FA failed to identify the presence of the neovascularization." (Or C, Heier J S, Boyer D, Brown D, Shah S, Alibhai A Y, Fujimoto J G, Waheed N. Vascularized drusen: a cross-sectional study. Int J Retina Vitreous. 2019 Aug. 20; 5:36-41, 36.37, 39, 40. doi: 10.1186/s40942-019-0187-6. PMID: 31452938; PMCID: PMC6702713.). This new technology of "OCT-A . . . gives you the ability to see subclinical neovascular complexes . . . which couldn't previously be visualized . . . " (quoting Rosenfeld P J in Stuart A. Retina Clinical Update. OCT-A: A Path to Earlier Diagnosis of Dry AMD. EyeNet. April 2018: 33-35, 33.). " . . . 8 of the 10 eyes with non-exudative CNV developed exudation . . . given the high rate of exudation . . . early treatment may prevent vision loss . . . " (Bailey S T, Thaware O, Wang J, et al. Detection of Non-exudative Choroidal Neovascularization and Progression to Exudative Choroidal Neovascularization Using Optical Coherence Tomography Angiography. Ophthalmol Retina 2019: 3(8):629-636.).

"[E]arly detection and treatment of pathological neovascularization is thought to be important in preserving as much vision as possible in these patients who convert to late neovascular AMD . . . [D]etection of subclinical MNV require[s] the use of ICGA" which "is expensive, time consuming, resource intensive . . . [and] would have remained unnoted [with FA and conventional OCT] . . . " (Roisman L, Zhang Q, Wang R K, Gregori G, Zhang A, Chen C L, Durbin M K, An L, Stetson P F, Robbins G, Miller A, Zheng F, Rosenfeld P J. Optical Coherence Tomography Angiography of Asymptomatic Neovascularization in Intermediate Age-Related Macular Degeneration. Ophthalmology. 2016 June; 123(6):1309-19, 1311, 1314-5 doi: 10.1016/j.ophtha.2016.01.044. Epub 2016 Feb. 12. PMID: 26876696; PMCID: PMC5120960.). However, with the new OCT-A technology, the undetectable "subclinical" nAMD or "moist" transitional conversion phase AMD could now be identified. Commonly used FA or standard OCT failed to detect it. (Id.) "[M]any studies have reported that indocyanine green angiography (ICGA) can improve the ability to detect CNV in patients with neovascular AMD compared to FA alone . . . OCT angiography provides a unique opportunity to directly visualize and study neovascular membranes and their microvascular details in both type 1 and type 2 AMD complexes, which are otherwise only visible with ICGA . . . (Eandi C M, Ciardella A, Parravano M, Missiroli F, Alovisi C, Veronese C, Morara M C, Grossi M, Virgili G, Ricci F. Indocyanine Green Angiography and Optical Coherence Tomography Angiography of Choroidal Neovascularization in Age-Related Macular Degeneration. Invest Ophthalmol Vis Sci. 2017 Jul. 1; 58(9):3690-3696. doi: 10.1167/iovs.17-21941. PMID: 28738134.).

Early diagnosis is critical for good visual results. "Early treatment [i]s critical for obtaining optimal vision . . . " (Brown G C, Brown M M, Rapuano S, Boyer D. Cost-Utility Analysis of VEGF Inhibitors for Treating Neovascular Age-Related Macular Degeneration. Am J Ophthal 2020; 218: 225-241.). "The ability to stabilize or improve vision with these treatments is a major step . . . Many studies have demonstrated that the better the visual acuity (VA) is at the time of treatment initiation, the higher the likelihood that VA will be better during at least the following 2 years; as such, detection of nvAMD when VA is relatively good is important. Data . . . at the time of nvAMD diagnosis suggest that patients are typically losing an average of 3 to 5 lines of vision and possibly more . . . [before] the diagnosis of nvAMD is made. The average patient may have nvAMD for 6 to 12 months before diagnosis and treatment initiation . . . Additional tools or other efforts to identify patients with nvAMD before substantial vision loss has occurred may reduce the amount of visual loss sustained . . . and have the potential to improve VA outcomes substantially." (Ho et al, 2017). Earlier diagnosis and earlier intervention by earlier identification of the transitional conversion phase or "moist" nAMD which tracks this new category of "subclinical" nAMD (before complete conversion and progression into late nAMD) can be the key to successful visual outcomes. The line between dry and wet is becoming more blurred with better technology and diagnostic techniques.

Prior to Dr. Pon's early discoveries, diagnoses of nAMD were typically made only after a patient's AMD had progressed to later in the course of nAMD and the patient became quite symptomatic with noticing loss or blurring of vision caused by the leakage of fluids from the abnormal blood vessels (i.e., conversion had already occurred with symptomatic progression). In those earlier days, nAMD was treated by "cauterizing" the abnormal blood vessels directly, which always left a blinding scar near or even in the center of vision by traditional scar-causing conventional laser coagulation (CLP). This was performed by delivering high levels of visible green or red laser energy to the abnormal vessels, raising the temperature of the abnormal blood vessels to a point at which the blood vessels and surrounding tissues were damaged, leading to visible scarring, which stopped the flow of blood into the abnormal leaking vessels. A significant consequence of this treatment, however, was that the scarring and other damage also resulted in permanent loss of vision to the lasered area and other negative consequences.

To solve these issues, a revolutionary non-scarring non-blinding laser technique was pioneered and referred to as laser for feeding vessels (FV) that supplied the leaking abnormal blood vessels to prevent the leakage of fluid and/or blood. By using low energy laser that was gradually increased stepwise and applied to the typically non-central FV identified by ICG angiography (ICGA), the FV blood flow could be stopped or decreased enough to "close" the CNV itself but not necessarily the FV itself. This could be performed without leaving a scar because of the gradual step-wise increase in laser energy "preconditioning" the target FV area. Furthermore, a 50% reduction in choroidal FV flow can eliminate CNV blood flow (which is the greater objective) and thus using higher laser energies for complete FV closure is not absolutely necessary (Flower R W, von Kerczek C, Zhu L, Ernest A, Eggleton C, and Topoleski L D T, Theoretical investigation of the role of choriocapillaris blood flow in treatment of subfoveal choroidal neovascularization associated with age-related macular degeneration. *American Journal of Ophthalmology* 2001: 132 (1): 85-93, 85.). "[B]oth partial and complete occlusion of either Sattler arteriole or venous vessels in the vicinity of the capillary-like vessels connecting a choroidal neovascularization to the underlying choriocapillaris results in significant choroidal neovascularization blood flowreduction." (Id.) "Clinical observations indicate that partial—as well as complete—photocoagulation of the (presumed Sattler's layer) FV adjacent to a CNV's penetrating vessel(s) is an effective means of decreasing the blood flow in the CNV (B M Glaser, R P Murphy, G Staurenghi, personal communications, 1999) . . . [E]ven 50% closure of a blood vessel entering the posterior aspect of the CC [choriocapillaris] in the vicinity of a capillary-like vessel leading to a CNV can be effective in reducing or possibly stopping CNV blood flow, regardless of whether that vessel is a feeding arteriole or a draining venule . . . [R]ather than total obliteration of a CNV (which frequently results in recurrence), the end point of laser photocoagulation treatment can be reduction of CNV blood flow to the extent that undesirable manifestations of the CNV—most notably retinal edema—are halted or reversed and (ii) that CNV blood flow reduction can be mediated by reduction of blood flow through the underlying CC . . . " (Lim J I. Age-Related Macular Degeneration. Third Edition. Boca Raton (FL): CRC Press; 2013. p. 295.). Experience with FV laser confirms complete FV closure is not required for C)NV (recently also referred to as MNV closure (confirmed by personal experience and by personal communication with Giovanni Staurenghi, M D, 2014).

The cessation of CNV blood flow is noted with only a 50% reduction in FV blood flow. (Flower et al, AJO, July 2001, 132(1): 85-93.) According to fluid mechanics for flow through a cylinder, using Poiseuille's equation for the flow rate, only about a 15% reduction in the diameter of the FV is needed to reduce flow by 50%, as the blood flow is directly proportional to the fourth power of the diameter. Poiseuille's equation is:

$$Q = -[\pi D^4/128\eta](dp/dxl)$$

for steady flow through a (horizontal) cylindrical pipe of length 1, uniform diameter D where Q=rate of discharge, $\eta$ is shear, and p is pressure. (McHenry, Robert and Pang, Alex Soojung-Kim, eds, *The New Encyclopaedia Britannica Macropaedia*, 15th ed, "Mechanics: Fluid Mechanics," 1998; 23: 702-773, 755-761.). The cessation or reduction of blood flow to the FV which can halt CNV progression can be affected at least in part by the photomechanical mechanism of localized tissue swelling constricting the affected blood vessels which could readily result in a 7.5% reduction in width at each opposing vessel wall as would be seen from two dimensions. Intracellular and intercellular edema or swelling can occur within an hour after the laser (Brinkmann R, Roider J, Birngruber R. Selective retina therapy (SRT): a review on methods, techniques, preclinical and first clinical results. *Bull Soc Belge Ophtalmol*. 2006; (302):51-69. PMID: 17265790.). Intracellular microbubble formation in response to short pulsation laser that results in cellular swelling and destruction has been reported under certain laser parameters.

The photomechanical effect of reducing this choroidal blood flow attenuates flow turbulence and may eliminate CNV formation and its proliferation. One of the mechanisms in the pathogenesis of neovascular AMD and its variants such as polypoidal choroidal vasculopathy (PCV) may involve the choroidal blood flow being overly rapid, turbulent, and out of a delicate balance such that nutrients and/or waste products are not adequately exchanged, leading to increased inflammation with abnormally higher reactive oxygen species (ROS) and flow abnormalities may additionally exacerbate this. In PCV, the resultant perturbations, vascular wall turbulence, shear forces, vortices, and eddies within the vascular anomalies and saccular outpouchings (which can be visualized on histopathology and by ICG angiography) can be identified clinically even before frank exudative changes (Ueta T, Iriyama A, Francis J, Takahashi H, Adachi T, Obata R, Inoue Y, Tamaki Y, Yanagi Y. Development of typical age-related macular degeneration and polypoidal choroidal vasculopathy in fellow eyes of Japanese patients with exudative age-related macular degeneration. *Am J Ophthalmol*. 2008 July; 146(1):96-101. doi: 10.1016/j.ajo.2008.03.002. Epub 2008 Apr. 24. PMID: 18439567.).

Another ocular disease involving neovascularization is proliferative diabetic retinopathy, which is associated with both Type I and Type 2 diabetes mellitus. Chronic exposure to the diabetic milieu typically leads to pre-proliferative retinopathy, which is associated with focal areas of ischemia. It is widely accepted that neovascularization is associated with increased expression of pro-angiogenic factors such as vascular endothelial growth factor (VEGF), along with reduced expression of anti-angiogenic factors, such as endostatin and pigment epithelial derived factor, PEDF. The change in the balance between pro-angiogenic and anti-angiogenic factors in the microenvironment may elicit neovascularization and induce capillary leakage. After several years, patients having pre-proliferative retinopathy experience retinal pathology characterized by the extensive loss of retinal capillaries and cotton wool spots, followed by the development of new vessels that grow from the retina into the normally avascular vitreous. The fragile new vessels are prone to leakage, causing macular edema and blurred vision. Susceptible to breakage, rupture of these abnormal vessels can result in immediate vision loss fromhemorrhage.

If permitted to grow, the neovascularization can form blinding fibrovascular membranes and cause the retina to detach. Under prior treatment protocols, proliferative diabetic retinopathy was treated at the proliferative stage of the condition by placing a grid of laser burns over the retina. This destructive treatment results in substantial vision loss. After a 20-year duration of diabetes, about 33% of young adults have received such laser treatments, with an associated decrease in visual acuity and visual angle.

The mainstream use of laser eye treatments had significantly dropped after the advent of a new approach for blocking the development of leaking blood vessels in the eye, namely, anti-VEGF agents, i.e., drugs that inhibit the function of vascular endothelial growth factor (VEGF). Anti-VEGF agents, however, also have their own serious problems, however. Every eye has VEGF (unless blocked by anti-VEGF agents) which normally functions to helps encourage the growth of new blood vessels, and likely also has other biological functions, including potential neurotropic effects. By complete VEGF blockade, normal physiological functions are defeated and adverse effects result from this unbalanced altered state. Effective anti-VEGF treatment requires burdensome repeated intravitreal injections and follow-up as often as monthly over a period of years. The more serious documented adverse effects include hospitalizations as high as 24.1% after anti-VEGF treatments (NEI [National Eye Institute], NIH [National Institutes of Health] Study: Ranibizumab [Lucentis] and Bevacizumab [Avastin] for Neovascular Age-Related Macular Degeneration, The CATT Research Group. *N Engl J Med.* 2011 May 19; 364(20): 1897-1908. " . . . serious systemic adverse events (primarily hospitalizations) was higher with bevacizumab [Avastin] than with ranibizumab [Lucentis] (24.1% vs. 19.0% . . . (p<0.04)."). Other serious adverse effects include ocular complications resulting in documented blindness (e.g., endophthalmitis, sterile intraocular inflammation, retinal detachment), ocular surface abnormalities with meibomian gland loss (Polat O A, Çetinkaya Z, Evereklioğlu C, Karaca Ç, Erkiliç K. Effect of Repeated Topical Povidone-Iodine and Antibiotic Applications on Meibomian Glands and Ocular Surface Parameters in Patients With Repeated Intravitreal Injections. *Eye Contact Lens.* 2021 Sep. 23. doi: 10.1097/ICL.0000000000000828. Epub ahead of print. PMID: 34570021.), cognitive decline, heart attack, stroke, thromboembolic events, and even death. Intravitreal use of Anti-VEGF agents, despite its small injection quantity, is documented to have increased mortality (>2-fold increase) after prior MI or stroke (Chen Y Y, et al. Increased mortality after intravitreal injections [IVI] of anti-VEGF for neovascular AMD [nAMD] among patients with prior stroke or acute myocardial infarction [AMI]. *Eye (Lond).* 2021 Mar. 2. doi: 10.1038/s41433-021-01416-1. Online ahead of print. "We found an increased mortality risk [HR 2.37] associated with IVI of anti-VEGF in nAMD patients with prior stroke/AMI compared to the mortality risk of nAMD patients with prior stroke/AMD but without exposure to anti-VEGF."), nephrotoxicity by prompting decreased protective inhibitory complement factor H (Keir L S, Firth R, Aponik L, et al, VEGF regulates local inhibitory complement proteins in the eye and kidney. *J Clin Invest.* 2017; 127(1):199-214; Hanna R M, Barsoum M, Arman F, Selamet U, Hasnain H, Kurtz I. Nephrotoxicity Induced by Intravitreal Vascular Endothelial Growth Factor Inhibitors: Emerging Evidence. *Kidney Int.* 2019: 96: 572-580; Shye M, Hanna R M, Patel S S, Tram-Tran N, Hou J, Mccannel C, Khalid M, Hanna, M, Abdelnour L, Kurtz I. Worsening Proteinuria and Renal Function after Intravitreal Vascular Endothelial Growth Factor Blockade for Diabetic Proliferative Retinopathy. *Clin. Kidney J.* 2020:13: 969-980), as well as possible increased cognitive impairment (Krader C G. Study results link frequent anti-VEGF injections, risk of cognitive impairment. Digital Edition, *Ophthalmology Times*: Nov. 1, 2020, Volume 45, Issue 18, Dec. 11, 2020. ("The findings from the first 143 patients with age-related macular degeneration (AMD) enrolled in the Brain Health Assessment in Macular Degeneration (BHAM) study were presented by Subhransu K. Ray, MD, PhD, at the virtual meeting of the American Society of Retina Specialists. He reported that patients who received higher cumulative anti-VEGF injections performed significantly worse on a test of cognition.")).

Dr. Pon's Early Discoveries and Procedures

Against the background of the shortcoming of high intensity laser treatments and anti-VEGF agents discussed above, Dr. Pon began intensive investigations into the causes of and potential treatments for AMD, which investigations led to multiple significant discoveries, including: (i) the discovery that rather than being two different conditions, dry AMD and wet AMD were simply different phenotypic stages of the same disease that all begin as dry AMD and that can be characterized, dependent on the technology and methods of detection, as exudative/non-exudative, neovascular/non-neovascular, clinical/subclinical, and by the detectable degree of neovascularization, (ii) the discovery that many of the cases that had previously been diagnosed as simply dry AMD were actually earlier stages of wet or neovascular AMD in which the neovascularization and/or fluid leakage had not yet progressed to a level whereby it was readily detectable using conventional diagnostic methods/systems, (iii) the discovery that a transitional "moist" phase of the disease (as dry phenotype converts to the wet phenotype) formerly lumped into the category of dry AMD, but with newer technology is placed into a "new" category of "subclinical" neovascular AMD, (iv) this "moist" or "subclinical" phenotype of wet or neovascular AMD could be treated early in symptomatic cases to delay or prevent its progression into the classically defined wet phenotype or clinical neovascular AMD, (v) the discovery that progression of the disease could be delayed or prevented by delivering pulsed, low level visible, red, infrared and/or near infrared electromagnetic energy to the choroidal blood vessels at subthreshold levels that did not produce any detectable scarring by biomicroscopy, fundus autofluorescence, fundus photography, fluorescein angiography (FA), or OCT, (vi) the discovery that partial narrowing of choroidal feeding vessel(s) only by about 15% in diameter was sufficient to prevent the progression of choroidal neovascularization (CNV) in "subclinical" or clinical neovascular AMD (which is now often referred to as macular neovascularization (MNV)) with remarkably improved vision as outcomes, (vii) retreatment was needed for frequent recurrences with periodic FA and ICG (indocyanine green) angiography monitoring until sufficient stabilization, (viii) the need for adjunctive anti-VEGF intravitreal injections was significantly reduced or even eliminated after the laser methodology, and (ix) the importance of performing a thorough history and review of the patient's past medical records which might reveal concurrent systemic or other ocular conditions by asking probing thoughtful questions regarding possible hidden visual symptoms of "subclinical" neovascularization which may not be obvious at first inspection.

The importance of a good thorough medical history cannot be underestimated. Clinical correlation should be always interpreted in conjunction with a careful comprehensive history including the past medical records. This includes: blurred vision, metamorphopsia, scotomas, color vision/facial recognition difficulties, misdirected saccades (Shanidze N M, Lively Z, Lee R, Verghese P. Saccadic contributions to smooth pursuit in macular degeneration. Vision Res. 2022 November; 200:108102. doi: 10.1016/j.visres.2022.108102. Epub 2022 Jul. 20. PMID: 35870286.) fixation instability (Nuthmann A, Thibaut M, Tran T H C, Boucart M. Impact of neovascular age-related macular degeneration on eye-movement control during scene viewing: Viewing biases and guidance by visual salience. Vision Res. 2022 Sep. 6; 201:108105. doi: 10.1016/j.visres.2022.108105. Epub ahead of print. PMID: 36081228.), nyctalopia, with factors decreasing AMD risk such as increased education, Japanese/Black/Latino ethnicity, diabetes (in 50%, can be protective), increased intake of vitamin E/vitamin C/zinc, as well as factors that increase AMD risk such as wet AMD or geographic atrophy in fellow eye, large or soft drusen, pigmentary changes, worse baseline visual acuity, UV/blue light/radiation exposure, age (over 65), female sex, white/Chinese/Pakistani ethnicity/race, light-colored irises, prior cataract surgery, hyperopia, family history, smoking, lack of exercise, diet high in fat, diet low in omega 3 and 6, vitamins, carotenoids and minerals. Also important in the history are higher risk categories of obesity (BMI>30 in ~33%), ischemic heart disease or heart failure (in >50%), hypertension (in ~75%), hyperlipidemia (in ~75%) (higher HDL increases risk; lower LDL, lower TG (triglycerides) decrease risk or have no effect (Wang Y, Wang M, Zhang X, Zhang Q, Nie J, Zhang M, Liu X, Ma L. The Association between the Lipids Levels in Blood and Risk of Age-Related Macular Degeneration. Nutrients. 2016 Oct. 22; 8(10):663. doi: 10.3390/nu8100663. PMID: 27782072; PMCID: PMC5084049.)). Other important information to include in a thorough medical records are details of: any prior medical or surgical treatments for non-ocular as well as ocular conditions, when these treatments occurred, and the subjective and objective responses, vision tests for best corrected visual acuities, distortions, retinal sensitivity (e.g., Snellen eye chart/Amsler grid/Fore-See home testing/microperimetry), the objective and subjective results before and after any treatments and whether any positive or negative symptomatic responses were life-altering or had changed daily activities, the interval before any positive or negative responses and the durability of such responses. All such factors in the complete history need to be carefully considered in order to achieve important early and optimal diagnosis and treatment for ocular disorders.

Over several years of clinical experience in a large number of patients, Dr. Pon discovered and confirmed that pulsed electromagnetic radiation in the form of pulsed low level (subthreshold) laser/light therapy (LLLT) treatment is effective to treat, prevent, slow, reverse or stop the progression of AMD and other chronic or progressive diseases of the retina, without causing any visible scarring or any other negative side effects. These include age-related, genetic, metabolic disorders and diseases of unknown etiology of widely varying genotypes and phenotypes.

Pon's LLLT experience is that although every individual case is different, many cases can stop progressing, even reverse, and remain stable after the regenerative 810 nm micropulse laser methodology without injections for years. Horsman also noted this in about 70% of his subthreshold micropulse series. (Horsman, B. Laser therapy for retinal pathologies. *Ophthalmology Management*, July 2018; 22: 34-35, 54-55.). This injection-free good vision durability after subthreshold micropulse LLLT treatments has also been observed with the anti-VEGF injection methodology as: "Johns Hopkins Medicine researchers report that as many as a third of those with the blinding retinal disease may someday be able to safely stop eye injection therapy without further vision loss . . . Across the board, the patients who could enter a treatment pause did the best even though they were receiving no anti-VEGF drugs. They had better visual acuity, better gain of vision and less fluid in their retina . . . " (Johns Hopkins Medicine. Study Finds Up to 30% of Patients with Wet Macular Degeneration Can Safely Stop Eye Injections. 1/18/2022. Hopkinsmedicine.org. https://www.hopkinsmedicine.org/news/newsroom/news-releases/study-finds-up-to-30-of-patients-with-wet-macular-degeneration-can-safely-stop-eye-injections. Accessed 2/19/22.) (Qin Y, Dinabandhu A, Cao X, Sanchez J C, Jee K, Rodrigues M, Guo C, Zhang J, Vancel J, Menon D, Khan N S, Ma T, Tzeng S Y, Daoud Y J, Green J J, Semenza G L, Montaner S, Sodhi A. ANGPTL4 influences the therapeutic response of neovascular age-related macular degeneration patients by promoting choroidal neovascularization. JCI Insight. 2022 Jun. 2:e157896. doi: 10.1172/jci.insight.157896. Epub ahead of print. PMID: 35653189.) (Cao X, Sanchez J C, Dinabandhu A, Guo C, Patel T P, Yang Z, Hu M W, Chen L, Wang Y, Malik D, Jee K, Daoud Y J, Handa J T, Zhang H, Qian J, Montaner S, Sodhi A. Aqueous proteins help predict the response of patients with neovascular age-related macular degeneration to anti-VEGF therapy. *J Clin Invest*. 2022 Jan. 18; 132(2):e144469. doi: 10.1172/JCI144469. PMID: 34874918; PMCID: PMC8759792.). Despite the unforgiving sensitivities of ocular tissue to scarring, LLLT can nevertheless deliver these remarkable healing effects for ocular disorders without any known adverse effects due to an experienced surgeon's skill in utilizing this PULSAR methodology with the appropriate selection of operating parameters for the pulsed LLLT that take into account the history, symptoms, and a live in vivo examination with ECLIPSE. Moreover, LLLT treatment can be performed very safely to provide optimal patient benefits. (Horsman, B. Laser therapy for retinal pathologies. *Ophthalmology Management*, July 2018; 22: 34-35, 54-55.).

Dr. Pon's Early Diagnostic Method

Dr. Pon's research elucidated the existence of a "whole new category" of neovascular AMD not previously detected by conventional methods of fluorescein angiography (FA) or standard optical coherence tomography (OCT). This new category of "subclinical neovascular macular degeneration" tracked the "moist" AMD as "dry" AMD converts to "wet" AMD. The diagnostic use of ICG angiography also enabled the detection of polypoidal choroidal vasculopathy (PCV), a subtype of wet AMD relatively common in Asians (as well as in some Caucasians) that may have the distinguishing feature of the absence of drusen, a typical hallmark of AMD. PCV "is rarely associated with drusen" and "is common in Asians," (Chen S J, Cheng C Y, Peng K L et al. Prevalence and Associated Risk Factors of Age-Related Macular Degeneration in an Elderly Chinese Population in Taiwan:

The Shihpai Eye Study. *Investigative Ophthalmology & Visual Science* 2008; 49 (7); 3126-3133. Polypoidal choroidal vasculopathy (PCV) [a subtype of WMD] "is rarely associated with drusen" and "is common in Asians."). This "new" category of "subclinical" neovascular AMD has been subsequently confirmed by published research: "Histopathologic specimens of eyes with clinically diagnosed dry AMD have shown newly-formed blood vessels [i.e., CNV] . . . " (Heiferman, Michael J. and Fawzi, Amani A. Progression of subclinical choroidal neovascularization in age-related macular degeneration. *PLoS ONE* 2019:14(6): e0217805. "Histopathologic specimens of eyes with clinically diagnosed dry AMD have shown newly-formed blood vessels invading into the subretinal space . . . [hence] subclinical choroidal neovascularization . . . ICG [studies] further supported this . . . [and] eyes with these ICG findings are at higher risk of . . . late AMD.") and "This choroidal phase of CNV may be common and unrecognized . . . Choroidal new vessels, often clinically unsuspected, are found commonly on histological examination of post-mortem eyes suffering from age-related maculopathy (ARM) . . . Attention is drawn to the initial choroidal phase of CNV and to the difficulty in its clinical recognition . . . CNVM . . . was found on pathological examination but had not been noted clinically (Sarks J P, Sarks S H, and Killingsworth M C. Morphology of Early Choroidal Neovascularization in Age-Related Macular Degeneration: Correlation with Activity. Eye 1997; 11; 515-522, 515, 516.), and this "clinically unsuspected subretinal neovascularization" occurred in clinically diagnosed dry AMD in post-mortem histopathology in as much as 56.7% (Sarks S H, "New vessel formation beneath the retinal pigment epithelium in senile eyes," Brit J Ophthal, 1973, 57: 951-965, 951, 963, 965 "[T]he fundus details corresponding to clinically unsuspected subretinal neovascularization have not been fully described . . . Small new vessels may remain clinically unsuspected . . . " Clinically unsuspected CNV occurred in post-mortem eyes in 56.7% and "67 percent of initially avascular lesions contained new vessels after an average follow-up period of 10 months . . . Subretinal neovascularization is a relatively common accompaniment of various manifestations of senile macular degeneration . . . ").

In ethnic African and Asian patients, the prevalence of PCV can be as high as 50+% (China, Japan, India), 77% (Thailand) (Kumar M, Moptom S E, Sen P, Khetan V, Bhende M, Sivaprasad S, et al. (2020) Prevalence of polypoidal choroidal vasculopathy in Indian population: Risk factors, clinical and imaging characteristics. *PLoS ONE* 15(4): e0231901.). "In a largely white [74%] patient population [in the United Kingdom], a high proportion [85%] of patients with haemorrhagic and exudative PEDs (pigment epithelial detachments, a finding in WMD) has evidence of polypoidal lesions on ICG angiography . . . PCV is much more common than we had appreciated . . . [and] may respond well to laser . . . " (Ahuja, Richard M., Stanga, Paulo E, Vingerlling, Joannes R. et al. Polypoidal choroidal vasculopathy in exudative and haemorrhagic pigment epithelial detachments *Br J Oph.* 2000; 84:479-484.). Research is demonstrating that "[PCV] is not a rare subtype of exudative AMD in whites . . . " (Lorentzen, Thomas D. et al. Prevalence of Polypoidal Choroidal Vasculopathy in White Patients with Exudative Age-Related Macular Degeneration. Systematic Review and Meta-Analysis. *Retina* 2018: 38:2363-2371.). Therefore, when there is a mixture of predominantly African-descent and Asian-descent as well as Caucasian patients as in Dr. Pon's patients, the use of diagnostic ICG angiography ((ICGA) and the alternative of laser treatment when indicated is reasonable and supported by the scientific literature.

When diagnosing patients who presented with symptoms of AMD, Dr. Pon employed multimodal imaging with ICGA, fluorescein angiography (FA), infrared (IR) imaging (sensitive for subretinal pathology), and utilized an extended contact lens increased-sensitivity photoluminescence stereoscopic examination (ECLIPSE) procedure. While the bilateral ICGA and ECLIPSE (which may have consumed 30 minutes or even more for full dark adaptation) and the ICGA/FA/IR/ECLIPSE diagnostic procedures presented time-consuming and practical challenges (which were not always feasible or cost-effective in a busy practice), it enabled Dr. Pon to definitively diagnose and characterize MNV in patients for whom MNV could not be diagnosed with conventional (FA, OCT, noncontact lens) techniques. In particular, since early PCV can develop without drusen and before frank exudative changes occur, ICGA (which is the gold standard for PCV diagnosis) would be necessary to detect earlier PCV lesions. "Accurate diagnoses of AMD subtypes are important for appropriate patient management. PCV constitutes a high percentage of patients with exudative AMD in Asian populations." (Chan, Wai-Man. Age-related Macular Degeneration in Asia. *Retina Today.* September 2009: 30-34.).

Research has demonstrated both that serum levels of indocyanine green (ICG) and ICG fluorescence can be detected for at least 120 minutes after IV injection and that ICG blood clearance is biphasic, with the ICG fluorescence peak shifting from 826 nm to 835 nm at 120 minutes with possible "fixation" of ICG to the CNV vessel walls. (Mordon S; Devoisselle J M; Soulie-Begu S and Desmettre T. Indocyanine Green: Physicochemical Factors Affecting Its Fluorescence in Vivo. *Microvascular Research* 1998; 55, 146-152. "Between 0 and 120 min, four [ICG] phases can be distinguished in which a wavelength shift from 826 to 835 nm is observed . . . The amphiphilic properties of ICG are consistent with fixation of some ICG molecules on sites other than plasmatic proteins after injection . . . a more or less selective fixation of ICG on the vessel wall of CNV (choroidal neovascularization) compared to normal choroidal vessels) . . . ") Thus, Dr. Pon's diagnostic technique was capable of identifying ICG fluorescence and subsequent phosphorescence in a patient's choroidal blood vessels under direct visualization allowing some 10,000-fold to 1,000,000-fold greater retinal sensitivity under dark adaptation (maximal after 30 minutes) with the ECLIPSE contact lens in place. This was possible even up to at least 2 hours or even longer after IV injection of the ICG. Moreover, ICG is believed to bind to vascular tissues at the endothelium or cellular level, and thus fixation of ICG to the choroidal feeding vessel (FV) supplying macular neovascularization (MNV) associated with ICG enables direct observation of the FV and choroidal neovascularization (CNV) in a patient's eye via the two photon absorption mechanism for infrared as " . . . humans can detect IR [infrared] at wavelengths longer than 1,000 nm" up to 1355 nm (Palczewska G et al. Human infrared vision is triggered by two-photon chromophore isomerization. *PNAS* Dec. 16, 2014: 111: (50). E5445-E5454; first published Dec. 1, 2014.). In some patients with occult CNV, intraretinal ICG dye leakage can be observed 20 minutes (range 11-34 minutes) after injection (Ho A C, Yannuzzi L A, Guyer D R, Slakter J S, Sorenson J A, Orlock D A. Intraretinal leakage of indocyanine green dye. *Ophthalmology.* 1994 March; 101(3):534-41. doi: 10.1016/s0161-6420(94)31323-6.

PMID: 7510380.) Therefore, subthreshold CW laser phase II ICG dye-enhanced local effects or micropulse laser phase I and III ICG-mediated systemic photonic effects may be more effective after the initial 20-30 minutes after injection as may be the practical situation in a busy practice.

By virtue of the ICGA/ECLIPSE diagnosis employed, Dr. Pon discovered that, despite the common clinical perception that wet AMD comprises only a fraction, e.g., 10%-15%, of all AMD, this may be a gross underestimate of AMD patients that actually have neovascularization, especially early neovascularization. as our diagnostic capabilities and technologies improve over time. This underestimation is consistent with that which has been confirmed by post-mortem histopathologic series, which have demonstrated a significant proportion (as much as 56.7%) of neovascular AMD was "unsuspected" and clinically misdiagnosed as "dry" AMD. In fact, post-mortem histopathology may be still underestimating the degree of actual neovascular AMD because it may be very difficult to make slides for histopathologic examination dissecting through every possible cross section that may contain tiny cellular elements of early neovascular budding. Therefore, these cases were clinically misdiagnosed as dry AMD but were actually wet AMD using the accepted pathologic definition. The most obvious reason for this large diagnostic discrepancy was that mainstream clinicians were not using the latest diagnostic methodologies such as ICG, IR photography, or even standard contact lens biomicroscopy. Standard OCT, FA and non-contact lens biomicroscopy can miss this key diagnosis of the presence of MNV and thus wet AMD. Therefore, early MNV was previously undetectable and thus "invisible" or"subclinical" without this additional testing by multi-modal advanced and resource-intensive ICG angiography, IR imaging, and 3-dimensional ECLIPSE. Dr. Pon's diagnostic methods scientifically demonstrated that conditions thought to be dry AMD in many cases were actually an early stage of wet AMD in which the transitional cellular/subcellular/molecular conversion process toward overt neovascularization with exudation had just begun, but had not yet evolved to a point of frank clinically obvious exudation. This can be the ideal phase to begin LLLT without known side effects when conditions may still have a degree of reversibility, to prevent progression, and to preserve vision. This early stage condition can be referred to as "subclinical neovascular AMD" or "moist AMD" and is known to carry a very high risk (at 15.2-fold higher (de Oliveira Dias J R, Zhang Q, Garcia J M B, Zheng F, Motulsky E H, Roisman L, Miller A, Chen C L, Kubach S, de Sisternes L, Durbin M K, Feuer W, Wang R K, Gregori G, Rosenfeld P J. Natural History of Subclinical Neovascularization in Nonexudative Age-Related Macular Degeneration Using Swept-Source OCT Angiography. *Ophthalmology.* 2018 February; 125(2): 255-266.) to 18.1-fold higher (Bailey et al, 2020) of progressing further to advanced neovascular AMD that may result in blinding complications.

As technology has further advanced, the actual classical distinction between dry and wet AMD became more blurred as this previously undetectable stage of neovascular AMD was identified. A more accurate characterization of disease progression is that all of AMD is actually the same disease that presents at different stages and phenotypic forms; however, all AMD begins the same way as dry AMD. Histopathology has demonstrated the same findings in both dry and wet AMD before the development of MNV. The basic premise of Dr. Pon's diagnostic methodology was to diagnose AMD early enough to prevent and to treat the disease before the "irreversible" later stages occur, after which it is very difficult if not virtually impossible to help or to improve the various aspects of vision that had already been lost, e.g., after the onset of relative scotomas (blind spots) and/or loss of visual acuity, reading vision and/or the ability to distinguish faces.

More recently, an imaging technology has emerged that also can be used in the performance of the diagnostic methods described above to detect the previously undetected subclinical neovascular AMD. It was reported that optical coherence tomography angiography (OCT-A) had identified a whole new category of AMD with previously undetectable "subclinical" neovascularization, mirroring the "moist" phase undetected by traditional methods in common use at that time. This "discovery" that was made using the new OCT-A technology merely confirmed the early diagnostic work that Dr. Pon had developed and was working to advance and to refine.

Dr. Pon's Early Treatment Method

Dr. Pon's early discoveries involving subclinical neovascular AMD, and early detection/diagnosis of neovascular AMD, enabled treatment of this condition before the disease progressed to a late exudative stage, i.e. before it reached the stage commonly known at that time as frank wet AMD. Ophthalmologists have for many years attempted to diagnose and treat AMD at the time of the unpredictable conversion event of dry to wet AMD. Delay in diagnosis and treatment is a prime factor in the majority of devastating losses of vision from AMD. Most wet AMD eyes already present with loss of functional reading and/or driving vision at baseline presentation and this demonstrates the delay or lack of early diagnosis and treatment (Ho et al, 2020) (assuming these patients did not previously have loss of reading vision early in life).

The methodology that Dr. Pon developed, the pulsed laser subthreshold anti-inflammatory regeneration (PULSAR™) treatment, is able to address this common issue among many others. It has been also referred to most commonly as low level laser/light therapy (LLLT), or photobiomodulation (PBM), or subthreshold micropulse laser treatment as well as by numerous other acronyms, variations and names in the scientific literature: subthreshold diode micropulse laser photocoagulation, MIP (minimal intensity photocoagulation)/PBMT (Photobiomodulation therapy)/LLLI (low level laser irradiation)/LLI (low-power laser irradiation)/LLL (low level laser)/PBT (photobiomodulation therapy)/FR/ NIR (far red/near infrared)/SDM (subthreshold diode micropulse)/LPLI (low-powerlaser irradiation)/LPLT (low-power laser therapy)/SRPT (subthreshold retinal phototherapy)/ SLT (subthreshold micropulse laser therapy)/SML (subthreshold micropulse laser)/R/NIR-IT (red/near-infrared irradiation therapy)/ST (subthreshold) laser/SMPLT (subthreshold micropulse lasertreatment)/MIRE (monochromatic infrared light energy)/LIPS (low intensity photostimulation)/MLRT (micropulse laser retinal therapy)/MPL (micropulse laser)/SNL (subthreshold nanosecond laser) . . . All of these treatments involve the delivery of non-scarring subthreshold levels of visible, red or near-infrared light to stimulate healing andregeneration for ocular tissues.

The PULSAR™ (or LLLT) treatment that Dr. Pon was developing uniquely focused the pulsed laser beam on choroidal feeding vessels with the intent of reducing blood flow rate and volume in the feeding vessels for the original target disease of AMD. Dr. Pon delivered low level laser/ light electromagnetic radiation of multiple wavelengths in the red and/or near infrared spectra coaxially in laser beams to choroidal tissues of one or both (sequentially) of a patient's eyes, more particularly, focusing the laser beams on one or more visible choroidal blood vessels of one or more of the patient's eyes. Moreover, the persistence of visible ICG dye in the patient's bloodstream, which Dr. Pon initially used for diagnostic purposes, as described above, can be "fixated" to the FV and CNV blood vessels in the patient's eyes, enabling precise delivery of the coherent photonic energy to the patient's choroidal blood vessels. In some embodiments, utilizing the visualization of the FV and the CNV (which was possible due to the ICG already present from the diagnostic technologies, human infrared two photon detection, and processes discussed above), the LLLT treatment focused the pulsed laser beam on a FV for a period of time sufficient to restrict blood flow in the FV to the CNV. Moreover, Dr. Pon discovered that reduction of blood flow by decreasing the vessel diameter by only about 15% at the time of treatment was sufficient to achieve remarkably good results.

In Dr. Pon's treatment method, an infrared (810 nm) laser was used in micropulse mode for the treatment of AMD and a low energy 650 nm visible red aiming beam was used to assist with aiming the 810 nm infrared laser beam on the desired ocular location. In the treatment methods employed by Dr. Pon, the aiming beam is used on a continuous wave mode during phase II of the treatment sessions for "moist" or wet AMD or its subtypes such as PCV. The 650 nm red diode laser aiming beam can itself provide up to 1 mW of LLLT power (i.e., its power can be varied from zero to 1 mW) and it can be turned on or off, as desired. Methods of delivering photonic energy using a sub-threshold laser included, for example, administering 810 nm-laser spots with a diameter of 50 μm, 75 μm, 125 μm, 200 μm, 300 μm or 500 μm directly to choroidal blood vessels. The power and delivery modalities were varied to reduce or avoid photothermal damage. Various parameters were evaluated, as discussed further below, to achieve true subthreshold effective treatment, including providing sufficient power to produce effective treatment but not too high to create tissue damage or destruction. It was found that the initial fluence of the 810 nm laser beam may vary widely between 0.059 Joules/cm$^2$ to 4,200 Joules/cm$^2$ depending upon the parameters and the contact lens magnification. The laser parameters derived from years of experience for any specific disease or situation would be adjusted to be in a window of being effective yet safe.

As one example of a treatment method developed by Dr. Pon, a topical anesthetic was first applied to the patient's eye to be treated and a stereoscopic 3 mirror Goldmann-type fundus contact lens with methylcellulose was placed on the eye. Other types of contact lenses could be used as long as their magnifications would be accounted for in the laser parameters. Examples of suitable topical anesthetics include, for example, one drop of Tetracaine 0.5% or Proparacaine. The patient is treated on the same day as soon as possible (usually within 30 minutes but up to 60 minutes) after the ICG dye (e.g. Akorn, Buffalo Grove, USA; 25-mg vial; Pulsion Medical Systems, Munich, Germany; 25- and 50-mg vials) injection (1.25-40 mg IV push in 0.5 to 2.0 ml, followed by a 5.0 ml saline flush) while there is still some FA and ICG dye still in the eye and in the circulation.

Laser treatment was performed using an Iridex Oculight SLx 810 nm micropulse capable diode laser with a biomicroscopic delivery system slit lamp adapter (Iridex Corp., Mountain View, California, USA) mounted to a Haag Streit slit lamp with converging optics. The instrument was initially set on low magnification for orientation and adjusted for higher magnification as needed.

In an initial pre-conditioning phase of treatment (referred to herein as "Phase I"), the laser parameters were initially set at very low fluence (e.g., between 0.059 J/cm$^2$ to 4,200 J/cm$^2$ of fluence per train of micropulses at 500 Hz if the power is at the minimum setting of 50 mW) and in micropulse mode to avoid any inadvertent retinal burns. Without being limited to any theory, it was believed that this low intensity pre-conditioning of ocular tissues in Phase I helped to prevent scarring and the inhibitory effects of scarring on cell/tissue regeneration following higher intensity laser treatment in subsequent phases.

The laser delivery instrument was set up to deliver electromagnetic energy at a wavelength of 810 nm (infrared) along with a nominal red aiming beam set at a wavelength of 650 nm. An optional (depending on the surgeon's level of experience and the level of ocular pigmentation) test spot in the peripheral retina can be performed with CW pulses beginning at 50 mW and adjusted upward (stepwise in 50 to 200 mW steps depending on the underlying degree of pigmentation) until the slightest visible reaction is observed to have an idea for a power ceiling (the micropulse power settings can be calculated based this ceiling number) beyond which not to exceed.

For the first phase (referred to herein as Phase I), the LLLT laser treatment is begun with the spot size set at 200 μm and in the micropulse mode with the micropulse duty setting at 5% and is adjusted incrementally during the course of Phase I treatment from 5% to 15%. The duty cycle and interval can be adjusted lower or higher as desired to change the repetition frequency (initially at 500 Hz) so long as it is not increased to a level that causes any visible tissue reaction. During Phase I of the treatment, the laser settings are gradually increased to achieve LLLT effects without scarring by gradually increasing the power or adjusting other parameters such as duty cycle or micropulse duration or micropulse interval or decreasing the spot size to 125 μm or 75 μm while still not causing any scarring. Parameters of the laser delivery instrument that were also adjusted incrementally during the course of Phase I treatment include, for example, the power of the beam, which was initially set at a power of 50 mW, exposure duration, which was initially set at 100 ms, exposure interval, which was initially set at manual repeat, and envelope duration, which was initially set at 2000 μs. During the course of Phase I, which lasted from about 1 minute to about 15 minutes, these parameters also were adjusted stepwise incrementally in 10 mW to 200 mW steps up to a maximum power of about 2000 mW (but usually no higher than 1000 mW) with exposure duration set at 100 ms, exposure interval set at manual repeat or 500 to 1000 ms, envelope duration of 2000 μs. It is to be understood that these adjustments are within the discretion of the operator and can be balanced to achieve pulsed delivery of photons to the target ocular tissue so long as no parameter is increased to a level that causes visible tissue reaction. Should the operator observe any visible tissue reaction, the parameters should be immediately adjusted to reduce the fluence to a level that avoids any further tissue reaction. This can be done, for example, by increasing the spot size if appropriate. Moreover, Dr. Pon discovered that continued pulsed treatment of the affected tissue with lower fluence following observation of a visible tissue reaction is effective to prevent scarring of such tissue and promotes healing and regeneration of the tissue following treatment.

The effects of LLLT may not be total dose dependent but instead "may depend on the rate at which light is delivered i.e. the power density . . . " Research has demonstrated that " . . . the biological effects of PBM depended on the power density of the light (mW/cm$^2$), and not on the total dose (J/cm$^2$) . . . (Vasilenko T, Slezák M, Kovác I, Bottková Z, Jakubco J, Kostelniková M, Tomori Z, Gál P. The effect of equal daily dose achieved by different power densities of low-level laser therapy at 635 and 670 nm on wound tensile strength in rats: a short report. Photomed Laser Surg. 2010 April; 28(2):281-3. doi: 10.1089/pho.2009.2489. PMID: 19743962.), (Oron U, Yaakobi T, Oron A, Hayam G, Gepstein L, Rubin O, Wolf T, Ben Haim S. Attenuation of infarct size in rats and dogs after myocardial infarction by low-energy laser irradiation. Lasers Surg Med. 2001; 28(3):204-11. doi: 10.1002/lsm.1039. PMID: 11295753.), (Lanzafame R J, Stadler I, Kurtz A F, Connelly R, Peter T A Sr, Brondon P, Olson D. Reciprocity of exposure time and irradiance on energy density during photoradiation on wound healing in a murine pressure ulcer model. Lasers Surg Med. 2007 July; 39(6):534-42. doi: 10.1002/lsm.20519. Erratum in: Lasers Surg Med. 2007 December; 39(10):808. Timothy, Peter A Sr [corrected to Peter, Timothy A Sr]. PMID: 17659591.), (Hamblin M R. Mechanisms and Mitochondrial Redox Signaling in Photobiomodulation. Photochem Photobiol. 2018 March; 94(2):199-212. doi: 10.1111/php.12864. Epub 2018 Jan. 19. PMID: 29164625; PMCID: PMC5844808.). Lanzafame et al. has shown that "the outcome of LLLT can be influenced by varying the irradiance and exposure time, despite keeping the energy density constant . . . a unique dose frequency regime may exist for tissues and cell lines . . . use of other treatment regimes resulted in bioinhibition, . . . [e.g.] two treatments per day were more effective than once daily therapy in some cases. Variation of exposure time and irradiance may account for conflicting results in the literature . . . multiple treatments per day is more effective than the traditional strategy of delivering a single treatment per day." (Lanzafame et al., 2007).

In certain embodiments, this property of dosage frequency per day being more effective can be advantageously utilized in a practical manner in the office by increasing the "off" or rest interval between micropulses or envelopes or CW durations and between phases 1, II, and III, which increases the length of the treatment session but does not require a patient to return multiple times on the same day. In certain embodiments, the power density or irradiance may be more important than the total dosage or energy density provided or the total number of spots since some biological effects appear to be mediated or influenced more by the rate of photonic delivery than the total number of photons delivered. This may be influenced by the ultrashort molecular time scales of quantum reactions and quantum entanglement compared to the many orders of magnitude longer time scales required for certain biologic processes to occur.

Now with micropulse, nanopulse, and even femtosecond pulses available with newer laser technology, the optimal frequencies or combination of frequencies can be more finely tuned into the ultra-short time scales of molecular and atomic dynamics and resonance harmonics. This is analogous to tuning a radio to the correct frequency for the best reception.

The individual uber-short micropulses from the Iridex Oculight SLx are on the order of magnitude in microseconds ($10^{-6}$ seconds) which is along the same magnitude as the fastest enzyme turnover time and faster than most other important biological processes including electron transfer by cytochrome c, neuronal coincidence detection, action potential duration, ATP synthase rotation, average enzyme turnover time, protein folding, protein translation, gene splicing, and so on as depicted in FIG. 2.

Thus, each pulse can take effect on this timescale and influence these other critical biological processes downstream which take place in orders of magnitude longer on a biological time scale. The importance to the fluence may therefore be quantum scale dependent to the individual fluence of ultra-short pulses: micropulse/nanosecond pulse/picosecond pulse/femtosecond pulse, each of which has yet another three orders of magnitude difference and dependent on the individual laser specifications) as the accompanying ultra-short laser off-interval may allow enough recovery time relative to the quantum timescale of molecular/sub-molecular/atomic/subatomic events. This may create a quantum time field in which the fluence or irradiance of single or multiple trains of ultra-short pulses to be less relevant than the fluence or irradiance of a single ultra-short pulse because of the relaxation time in between individual ultra-short pulses may be adequate on a quantum time scale for sub-molecular or subatomic vibronic, polaritonic, or harmonic oscillatory resonance effects.

Ultrashort femtosecond ($10^{-15}$ sec.) pulses are used in LASIK and cataract surgery. These pulses are on the same order of time magnitude as the elementary processes of bond breaking and bond formation which are femtosecond to picosecond processes. (El Hage K, Brickel S, Hermelin S, et al. Implications of short time scale dynamics on long time processes. Structural Dynamics (Melville, N.Y.). 2017 November; 4(6):061507. DOI: 10.1063/1.4996448. PMID: 29308419; PMCID: PMC5741438.). Lasers with femtosecond to picosecond pulse capability can be adapted for direct ocular delivery through the optically transparent cornea, lens, and retina (including the retinal pigment epithelium with longer red to infrared wavelengths) to the rapidly circulating choroidal vasculature. This allows for direct penetration to the human vasculature with efficient and wide dissemination of photonic vibrionic pulse and energy transfer to bring tissues and cells into a healthier homeostasis. This photonic delivery system can be superior to requiring penetration through optically opaque skin, bone, muscle, soft tissue, or cranium. This may be further enhanced by preinjected circulating photosensitive ICG dye, leukocytes (which when stimulated secrete circulating cytokines and growth factors) as well as by other naturally circulating chromophores such as hemoglobin molecules with its light sensitive protoporphyrin IX ring (and not via mitochondrial interaction since circulating red blood cells lack both mitochondria and nuclei) and hemoproteins such as catalases, heme peroxidase, cytochromes, endothelial nitric oxide synthase, or myoglobin. All molecules and atoms vibrate. The transfer of photonic energy in this fashion may be able adjust the polaritonic, molecular, atomic, and subatomic vibratory levels and vibronic coupling to more optimal harmonic frequencies. It may also take effect as quickly as a form of administration as an intravenous infusion which is consistent by the observation of almost immediate patient results.

The fluence or energy density is heavily influenced by the spot size and this relationship is nonlinear and quadratic in relation to spot sizes. However, its clinical effect appears to vary more linearly. For example, for spot sizes of 75 microns for even 50 milliwatts power would produce the irradiance or power density at 1,048 mW/cm$^2$ and a 750 micron or 0.75 mm spot size at 50 mW produces only 5.9 mW/cm$^2$. A 10-fold change in spot size diameter produces a 178-fold change in irradiance but the clinical effect does not approach a 178-fold difference.

The Iridex line of slit lamp adapters (SLA) delivery systems have spot sizes on certain models that can be easily changed. The spot sizes may be varied from 75 μm to 125

µm or 200 µm or 300 µm or 500 µm or 600 µm or 1000 µm or 1800 µm or 3000 µm or to 5000 µm in order to adjust and lower the irradiance and can be changed up or down as needed. All other laser parameters can also be adjusted to change the irradiance and thereby also changing the fluence to be delivered as needed. For example, if there appears to be more prominent pigmentation in the immediate area being treated one would simply flip the spot size to a larger spot size to lower the irradiance or one may lower the micropulse duration or the power or increase the "off" intervals or lower the frequency or number of pulses. All the laser parameters are variable during the course of the treatment and are dependent on a number of factors such as, for example, the diameter of the feeding vessel being treated, the amount of localized pigmentation in the target tissue, direct stereoscopic visualization of the localization of the area of increased outer retinal thickness (ORL, which is highly correlated with specific areas of exudation in neovascular AMD), the precise instantaneous reaction to treatment, as well as patient cooperation and other variables.

After treating a FV as described above, the surgeon can move directly to Phase II (as discussed further below) or can direct Phase I treatments to other feeding vessels or to other locations on the same feeding vessel before proceeding to Phase II. When selecting specific points of a FV for treatment, it is preferred to target a FV site along its course outside the foveal avascular zone (FAZ), if possible, to prevent any inadvertent tissue damage and/or scarring that may result in central scotoma that can eventually enlarge as much as 300%. The combined HS-ICG/FA image is utilized for this targeting by the placement of the cursor on the HS-ICG portion of the ICG/FA image which corresponds virtually pixel to pixel to a companion cursor on the FA portion of the HS-(high speed)-ICG/FA image. The retinal vessels act as an essential map with distinct landmarks to precisely localize the FV targeted since the choroidal vasculature is not as easily visualized clinically. The laser is applied to the FV in the very high flow choroid directly without causing any scarring by using this technique. The dosage or number of spots is variable and depends on a number of factors including importantly the type of tissue and the severity of the underlying condition to be treated.

After completion of Phase I of a LLLT treatment, the objective of Phase II is to completely or partially (e.g., by about 15%) close the choroidal feeding vessel(s) if treating neovascular AMD or its subtypes or variants such as PCV (polypoidal choroidal vasculopathy). For Phase II, the laser is switched from micropulse to continuous wave (CW) mode. While in CW mode, the laser then is manually pulsed in trains of pulses starting again at the lowest possible power setting at 50 mW and then again gradually increasing the power stepwise in 10-100 mW steps, typically not much higher than 900 mW, taking great care as to avoid any reaction in the surrounding tissues. The interval between pulses may vary between 1 to 120 seconds to allow for complete thermal relaxation. As with Phase I, in the Phase II CW mode, the technique parameters can vary widely with each patient depending on cooperation as well as individual and intraretinal pigmentation differences over short distances of less than 75 microns and pigmentation can vary by a factor of 2 or more. The challenge for effective feeding vessel clot formation to occur is to incite enough cellular damage to FV(s) to cause injury to the endothelial cells to induce tissue factor (TF) and clot formation without completely destroying the cells. This process can be facilitated by the presence of ICG still in circulation after the initial injection for diagnostic purposes. At this time, well within usually 2 hours of injection, ICG dye can be detected and in circulation. The 810 nm laser (with as little as 0.6 to 1.8 $J/cm^2$ fluence) can then be utilized as ICG dye-enhanced photodynamic therapy to stimulate the ICG to cause localized damage to the vessel walls. It has been proposed that there is "selective fixation of ICG on the vessel wall of CNV (choroidal neovascularization) compared to normal choroidal vessels . . . " (Mordon et al, 1998). This allows for very low fluences (well within the range of LLLT) to be effective in closing or reducing the blood flow through the FV. The 650 nm aiming laser beam (with a maximum output of 1 mW) also has potential use for its regenerative properties and thus "off" intervals and the power is usually set just enough to be visible and rarely at maximum). After Phase I, there is a rest interval, and then the Phase II treatment segment is begun and may last between 1-15 minutes. For example, between 294 to 2940 Joules total energy would be delivered for a total of 20 to 200 pulses at an irradiance of 14.7 $J/cm^2$ per 100 msec pulse if the power setting was unchanged at 50 mW and spot size of 200 microns. The technique however involves slowly/gradually increasing the irradiance stepwise with the power settings and adjusting the other laser parameters as needed so the total energy delivered may be much greater yet not leave any scar because of the preconditioning with LLLT of phase I and later of phase III and intermittently during phase II as needed. This would be applied during a single treatment session using the photonic energy of the 810 nm laser beam for the condition of neovascular AMD. The actual total duration (as much as 45 minutes and perhaps up to 60 minutes on occasion) of the total Phase I, Phase II and Phase III treatment segments (which involve both the 810 nm infrared and the aiming beam 650 nm red diode wavelengths) thus may have an even more overriding positive effect on the results than other laser parameters since this enables a very gradual increase in enzymatic causes of cell death for tens of minutes in a controlled fashion maintaining a careful balance in not creating a scar and without completely destroying endothelial cells that secrete TF that is needed for maintenance of a thrombotic effect for continued FV closure. During all treatments, the aiming beam and slit lamp beam (from a Haag-Streit or a Zeiss slit lamp or comparable models) are minimized to the lowest levels necessary to achieve the desired treatment and turned off whenever the laser is not in active use such as during "off" treatment intervals.

To maximize flexibility for obtaining the best outcomes, the laser can be easily switched back and forth between Phase II and Phase I during the Phase II treatment segment by the touch of a button on the laser console front panel by the surgeon to allow more mid-phase conditioning or "rest" between series of continuous wave laser pulses. This allows for additional adjustments to achieve optimal results especially without causing any scarring. The endpoint of Phase II is reached when the slightest reaction is noted in the vessel wall indicating that the feeding vessel is partially closing by the 15% reduction of diameter enough to reduce total flow by 50% to close the MNV (macular neovascularization).

After completion of Phase II, the laser mode is switched back to micropulse at the low fluence settings to treat the same area in the third and final phase of the pulsed LLLT treatment to maximize recovery/regeneration of the treated ocular tissues (referred to herein as "Phase III"). Phase III is applied directly to the vessel after the high energy is used in Phase II to "post-condition" the treated ocular tissue and to aid in the healing of any tissue that may show subtle signs of a laser burn being formed in or bordering the targeted area (in particular with regard to more pigmented areas). The Phase III treatment is performed in the same manner as Phase 1 and helps to ensure further against any scarring and also to improve retinal function, and to facilitate retinal healing after any inadvertent laser photocoagulation. Phase I and Phase III can also be performed focally to microvascular abnormalities as well as in a wider grid or confluent grid pattern depending on the conditions to be treated. Research has shown that LLLT performed before, during, or even after treatment with higher energy (which has higher scarring potential) protects against the initial laser scarring. It may also improve retinal function and healing and improve visual cortical function.

The length of the laser procedure itself is highly variable but may next take as long as 45 minutes or even up to 60 minutes or more in certain cases depending on the number of FVs as well as the individual response to each pulse and the cumulative length of "off" intervals and on patient cooperation. Adequate time for "rest" between laser pulses and trains of laser pulses (micropulse, nanopulse and so forth) needs to be provided to allow for "rebalancing" molecular homeostasis and vibratory equilibrium. Increasing "off" laser intervals and time between phases I, II, and III allow for an increased same day dosing frequency (tracking separate doses on the same day which may be beneficial) based on the ultrafast time scales of molecular events. Nevertheless, even with this caveat, experience is still required for optimal results and there may be a considerably steep learning curve. During the LLLT treatment, when at low temperature and in micropulse mode, the controlled slow elevation in temperature can be continued as needed and kept in proximity to the absorbing chromophores. Thus, one would not see blanching because you do not have enough thermal conduction to affect the retina's transparency.

At the conclusion of the procedure if long, a drop of ketorolac tromethamine 0.4% (Acular® LS, Allergan, Inc, Irvine, CA, USA) may be placed in the treated eye if needed to address any discomfort; however, there is usually little to no discomfort after the procedure when ketorolac is not used. Rarely, an epithelial defect may arise after using the contact lens even with methylcellulose gel applied, especially if the procedure is lengthy, and in this case, a bandage contact lens or patch may be placed overnight.

The example treatment described above using an 810 nanometer laser with a 650 nm aiming beam caused no visible damage to the neurosensory retina. The subvisible laser application in Dr. Pon's methods is believed to have mobilized hematopoietic stem cells and recruited them to the RPE layer, where they had a healing and regenerative effect on the ocular tissues (by attracting hematopoietic stem cells via elevation of SDF-1 to regenerate RPE). By using repetitive, brief pulses of laser during a single exposure, the amount of heat conduction was limited and subsequent RPE damage was avoided. The laser treatment was controlled to reduce or eliminate intraoperative visible tissue reaction leading to necrosis and/or to programmed cellular death (apoptosis).

Subthreshold short and ultrashort pulse LLLT treatments as described herein can be performed at various wavelengths, such as within a range of about 400 nm to about 2900 nm. Use of single or multiple, simultaneous or sequential, differing wavelengths can have differing biological effects. The selection of laser wavelengths is easier if the laser is tunable, and this can impact the available laser properties and parameters such as the beam profile, spot sizes, frequencies, short pulse durations and intervals, power output, exposure envelope duration. In order that the retinal tissue is not damaged and yet the therapeutic effect is achieved, the appropriate laser parameters must be selected from those available. Typically, the individual micropulse laser light pulse is less than a millisecond in duration, and typically between 100 microseconds to 300 microseconds in duration. Nanosecond pulses, picosecond pulses, femtosecond pulses are orders of magnitude shorter and may be more useful for stimulation or inhibition of specific biological processes in various other conditions. Just as different medications and different dosages of the same medication will have differing effects on different patients with the same disease, the same applies to the laser wavelengths and multiple laser parameters.

Another parameter that Dr. Pon evaluated when developing the LLLT treatment methods was the duty cycle, or the frequency of the train of micropulses, including the length of the thermal relaxation time in between consecutive pulses. He determined that, if the laser procedure is performed properly, the use of a 5% to 15% duty cycle provides adequate healing effects without a significant thermal rise that would cause scarring or lethal cell injury. In general, the lower the duty cycle, the longer the exposure envelope duration can be. For example, if the duty cycle is less than 5%, the exposure envelope duration in some instances can exceed 500 milliseconds.

Using the foregoing parameters, non-scarring and otherwise harmless yet therapeutically effective subthreshold LLLT treatment produced benefits of halting the progression of AMD, and actually reversing AMD by regenerative healing of ocular tissues, but avoided drawbacks and complications of conventional phototherapy, including scarring and tissue damage. Adverse treatment effects were essentially eliminated and functional retina preserved rather than sacrificed.

In alternative embodiments of the method, the subthreshold laser can be provided on an outpatient or inpatient basis using local anesthesia with single and/or multiple wavelengths locally by one treatment or serial treatments spaced out over time. In embodiments in which multiple wavelengths are used, the wavelengths can be in the visible light spectrum, in the near infrared spectrum or in the infrared spectrum. Also, a variety of laser/light systems can be employed as alternatives to a diode laser system. For example, an alternative suitable system is an emerald laser, which exhibits a wide fluorescence spectra capable of laser action for all wavelengths from 670 to 850 nm. Another example of a suitable laser delivery devices is a titanium:sapphire laser. It is not intended, however, that this disclosure be limited to any particular laser delivery device, it being understood that other laser/light devices can be used to practice the principles of this disclosure.

Figure 3:
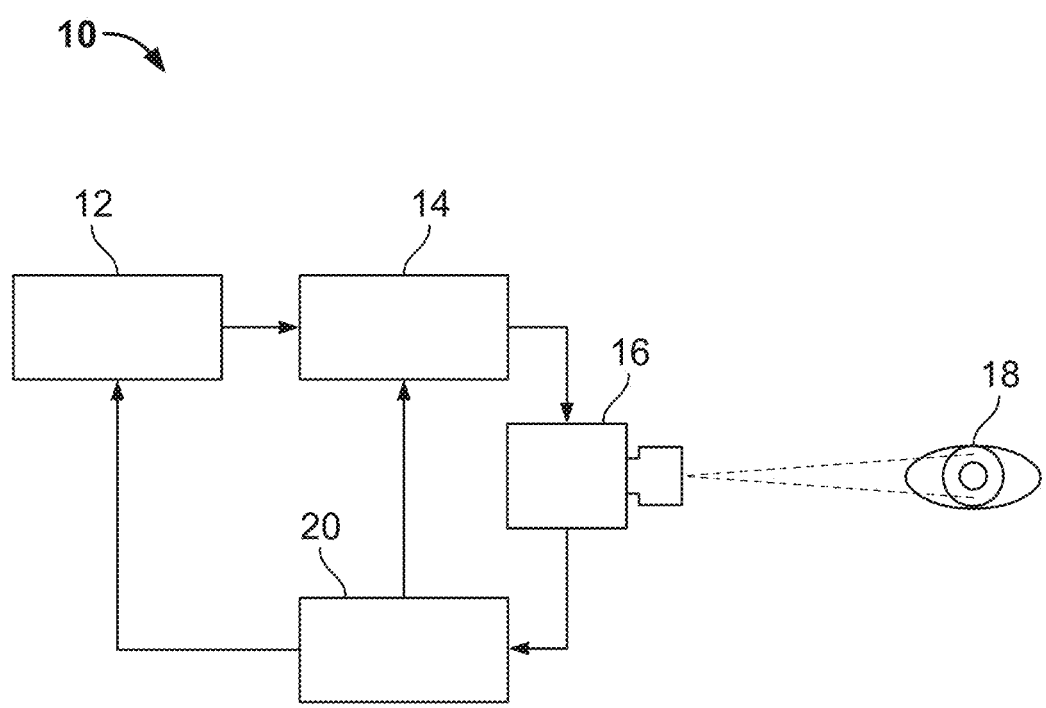
FIG. 3 is a schematic diagram of a system embodiment for realizing various process embodiments of the present disclosure.

With reference now to FIG. 3, a schematic diagram is shown of a system embodiment for realizing various process embodiments of the present disclosure. The system, generally referred to by the reference number 10, includes a laser console 12, such as for example a console of an 810 nm near infrared micropulsed diode laser. The laser generates a laser light beam which is passed through optics, such as an optical lens or mask, or a plurality of optical lenses and/or masks 14 as needed. The laser projector optics 14 pass the laser beam to a coaxial wide-field non-contact digital optical viewing system/camera 16 for projecting the laser beam onto the eye 18 of the patient. The laser is preferably focused on one or more ocular blood vessels, such as choroidal feeding vessels. It will be understood that the box labeled 16 can represent both the laser beam projector as well as a viewing system/camera, which might in reality comprise two different components in use. The viewing system/camera 16 provides feedback to a display monitor 20, which may also include the necessary computerized hardware, data input and controls, etc. for manipulating the laser 12, the optics 14, and/or the projection/viewing components 16.

This cutting-edge technological innovation developed by Dr. Pon intentionally leaves no scarring or permanent blind spots (which is a major breakthrough advantage), delivers virtually immediate as well as long-term improved vision, has no significant adverse effects, and can treat a wide range of AMD and other eye diseases including occult CNV (now also termed MNV or macular neovascularization) in AMD.

The photodynamic treatment using low fluences, coupled with the use of ICG dye not only is effective in restricting the blood flow to FV(s), which benefits AMD patients, but it also was found to have healing, rejuvenating and even stem cell regenerative effects on ocular/retinal tissues outside the targeted treated area. For example, in treating the "subclinical" form of wet (neovascular) AMD, this can be virtually simultaneously initiated at one treatment session, where the different phases of laser treatment after ICG dye injection would have different therapeutic effects.

In subsequent research, LLLT's effectiveness in wet AMD was clearly demonstrated by significant visual acuity improvement in 93.9% (P<0.001) as well as improvements, or even reversal, of metamorphopsia, scotoma, edema and bleeding in LLLT-treated patients in a controlled randomized clinical trial of LLLT for all stages of AMD with 5 years of follow-up. (Koev, K., Avramov, L., Borissova, E. Five-year follow-up of low-level laser therapy (LLLT) in patients with age-related macular degeneration (AMD). *J. Phys.: Conf Ser.* 992 012061, 2018.). This study used laser energies that were as low or lower than that used in Dr. Pon's subthreshold laser methodology. Additional recent studies have confirmed the utmost importance and desirability of early diagnosis and treatment of neovascular AMD for improved patient outcomes. (See, e.g., Ho A C, Kleinman D M, Lum F C, et al, Baseline Visual Acuity at Wet AMD Diagnosis Predicts Long-Term Vision Outcomes: An Analysis of the IRIS Registry. Ophthalmic Surg Lasers Imaging Retina. 2020 Nov. 1; 51(11):633-639; Ho A C, Albini T A, Brown D M, et al.. The Potential Importance of Detection of Neovascular Age-Related Macular Degeneration When Visual Acuity Is Relatively Good. JAMA Ophthalmol. 2017 Mar. 1; 135(3):268-273; and Bailey S T, Thaware O, Wang J, et al. Detection of Non-exudative Choroidal Neovascularization and Progression to Exudative Choroidal Neovascularization Using Optical Coherence Tomography Angiography. *Ophthalmol Retina* 2019: 3(8):629-636.

In addition to using the methods developed by Dr. Pon to treat wet AMD, the method is also effective for the treatment of other ocular diseases, including pre-proliferative retinopathy, diabetic retinopathy, choroidal neovascularization, glaucoma, retinitis pigmentosa, corneal dystrophies, retinoschisis, Stargardt's disease, autosomal dominant drusen, and Best's macular dystrophy. This cutting-edge technological innovation intentionally leaves no scarring or permanent blind spots (which is a major breakthrough advantage), delivers virtually immediate as well as long-term improved vision, has no significant adverse effects, and can treat a wide range of AMD and other eye diseases including occult CNV (now termed MNV or macular neovascularization) in AMD.

Possible Modes of Action

Bone marrow-derived hematopoietic stem cells (HSCs) are able to repair damaged tissues, including heart, liver, brain, muscle and kidney. Without wishing to be bound by theory, it is believed that hematopoietic stem cells may have had a significant role in the successes achieved by Dr. Pon and that Dr. Pon's pulsed sub-threshold anti-inflammatory and regenerative (PULSAR™) laser stimulation of the choroidal blood vessels induced recruitment of HSCs that subsequently transdifferentiated into RPE-like cells.

There can be an induction stimulatory phase which recruits HSCs to replace and regenerate RPE (retinal pigment epithelium, the reputed primary defective cell in AMD), to offer neuroretinal protection as well as to disseminate systemic photonic effects. HSCs are bone marrow-derived cells that represent an endogenous source known for their reparative potential as well as for their plasticity. HSCs recruited to areas of injury to effect the repair of the injured tissue. Without wishing to be bound by theory, it is believed that hematopoietic stem cells may have had a significant role in the successes achieved by Dr. Pon and that Dr. Pon's sub-threshold LLLT or PULSAR™ treatment of the choroidal blood vessels induced recruitment of HSCs that subsequently differentiated into RPE-like cells.

If desired, the number of hematopoietic stem cells present in the circulation of a subject may be increased prior to, during, or following delivery of laser stimulation. In one embodiment, this increase in hematopoietic stem cell number is accomplished by mobilizing hematopoietic stem cells present in the bone marrow of the subject by administering any one or more of SDF-I (stromal derived factor), transforming growth factor-$\beta$ (TGF-$\beta$), an early acting hematopoietic factor, described, for example in WO 91/05795, stem cell factor (SCF), thrombopoietin (Tpo), granulocyte-macrophage colony stimulating factor (G-CSF), NIP-I$\alpha$, stem cell factor (SCF), interleukin-1 (IL-I), interleukin-3 (IL-3), interleukin-6 (IL-6), interleukin-7 (IL-7), interleukin-8 (IL-8), interleukin-11 (IL-I1), interleukin-12 (IL-12), fims-liketyrosine kinase-3 (flt-3), Oncostatin M, FLK-2 ligand, MCSF, FLT-2 ligand, and Epo. SDF-I is a potent cytokine that induces the recruitment of stem cells. SDF-I is expressed by RPE cells during stress. Administration of G-CSF and/or SDF-I will increase the number of HSC in the peripheral blood and will likely enhance subsequent HSC recruitment to the retina and RPE layer.

In Dr. Pon's method for the treatment of AMD, the induction stimulatory/preconditioning phase discussed above (Phase I) was followed by a photodynamic destructive phase localized to the late ICG bound to the FV endothelium supplying the MNV (Phase II). The laser delivered in Phase II was to be just enough to reduce vessel diameter by about 15% to reduce blood flow by about 50%, thereby allowing destruction by highly localized vascular closure of any viable neovascular lesions (CNV). It was discovered that complete FV closure was not necessary. Nevertheless, this phase II methodology can still achieve a complete FV closure after ICG injection with "as little as 0.6 to 1.8 J of energy to the fundus, producing no visible change in the fundus." (Flower R W. Optimizing treatment of choroidal neovascularization feeder vessels with age-related macular degeneration. *Am J Ophthalmol* 2002; 134(2):228-39.).

Following the photodynamic destructive phase (Phase II) was a regenerative healing/post-conditioning phase (Phase III) that promotes cellular activity locally (one of which is to prevent local scarring which can be inhibitory of regeneration). This entire process can be very dependent on the specific laser parameters of the multiple wavelengths chosen (including the 810 nm infrared beam and the low energy 650 nm red aiming beam in the representative procedure described above). Subsequently, research demonstrated red light to improve mitochondrial and photoreceptor performance, color contrast sensitivity and rod thresholds for patients older than 40 years.

Without intending to be limited to any theory by which the present disclosure achieves its beneficial results, it is also believed that the infrared and near infrared wavelengths utilized in the PULSAR™ or LLLT treatment developed by Dr. Pon produced beneficial biological effects on biomolecules in the patient's choroidal and/or retinal tissue through quantum harmonic resonance with biomolecules.

Researchers have reported that the retina has the greatest energy demand in the body because of the high metabolic rate of photoreceptors, which are rich in mitochondria, and 670 nm light delivered to the retina of aged animals has been shown to improve mitochondrial respiration, increasing their membrane potentials and improve ATP production. Application of 670 nm light also has been shown to increase expression of cytochrome c oxidase (COX) and reduced expression of acrolein. (Gkotsi D, Begum R, Salt T, Lascaratos G, Hogg C, Chau K Y, Schapira A H, Jeffery G. Recharging mitochondrial batteries in old eyes. Near infrared increases ATP. *Exp. Eye Res.* 2014: 122, 50-53). Acrolein, an oxidative stress marker is increased in retinal degeneration and in Alzheimer's disease. Gkotsi et al. also demonstrated that there was a than 3-fold greater concentration of ATP in the retina compared with the brain. Through these mechanisms it is possible to reverse important changes occurring in AMD before it takes root, becomes irreversible and causes serious damage to cells and biological functions such as high ATP energy-consuming vision.

Complex polyatomic biological molecules may have numerous eccentric dipoles arising from multiple heteronuclear bonds. The arrangement of dipoles and their charge separations may be complex, but nevertheless, the red/infrared laser pulses are believed to align the various dipoles via repetitive resonating pulses into a new quantum harmonic vibrational state and conformational pattern facilitating the reactions that activate or facilitate the various beneficial biological processes that are actually observed.

The infrared laser energy can be transformed into vibrational and rotational states of the bonds between atoms.

The LLLT treatment described herein delivers photons to photoexcite molecules into quantized excited singlet and triplet states, which lead to downstream effects. Molecules in singlet and triplet states react chemically in different manners. It is possible to affect chemical reactions by the transfer of electronic energy from one molecule to another in the reacting system. A photochemical reaction necessarily begins with the absorption of a quantum of electromagnetic energy. Molecules also undergo transitions between rotational and vibrational states. Such transitions either can be spontaneous or can be induced by the application of appropriate external electromagnetic fields at the resonant frequencies. The LLLT treatment is believed to provide these appropriate conditions to induce molecular transitions that result in the downstream cascade of beneficial effects that are observed empirically.

The molecular transitions may also duplicate effects that drug ligands produce. Hemoglobin has a porphyrin ring chemical structure (consisting of four pyrrole rings) that is virtually the same as the porphyrin ring structure of chlorophyll (noting the magnesium metallic substitution for iron) and thus may act similarly as with chlorophyll by being a chromophore that can be photo-activated preferentially as evidenced by absorption peaks at specific wavelengths of electromagnetic energy carrying quantized energy as photons. It may also function as an energy transfer molecule.

Other human chromophores or biochromes that may also transfer or accept energy with downstream biological effects include myoglobin, riboflavin, cytochrome c, retinoids, protoporphyrin-IX heme (which has a binding domain on the N terminus of soluble guanylate cyclase and thus may modulate the messaging of cyclic GMP and related compounds), vitamin D, vitamin B12 (which also has a porphyrin ring structure), and the pyrrole ring system that is present in the amino acids proline and hydroxyproline.

These mechanisms may explain how the quantum harmonics of molecular dipoles affect the health and functioning of a cell. The end result can be the phosphorylation/dephosphorylation of various biomolecules in multiple molecular pathways and cascades such as members of the PI3K/Akt/mTOR [phosphatidylinositol-3 kinase/A stock k strain thymoma/transforming (or protein kinase B)/mammalian target of rapamycin] or MAPK/ERK [mitogen activated protein kinase/extracellular signal-regulated kinase] pathways, which can lead to cellular proliferation and regeneration. Quantum physics explains photons as having a dual particle and wave nature. The quantum mechanical molecular orbital theory explains that a molecular orbital is a wave function that describes the distribution of an electron all over the nuclei of a molecule. Molecular orbital theory is widely used to describe spectroscopic properties of molecules, in which electromagnetic energy can excite an electron from one molecular orbital to another and all the atoms contribute to the shift in electron density that accompanies the excitation. The principles of quantum physics that are now well accepted and observed experimentally should also apply to chemistry and biology. The laws of nature should apply universally and thus quantum principles should also apply to the control of biochemical reactions are affected by the specific resonances, vibrations, and frequencies in photon-phonon interactions, light-matter couplings or polaritonic nature of photonic interactions with the biomolecules in the microenvironments essential for life processes. This suggests that the photonic energies of LLLT can be efficiently translated or transferred (via properties such as "quantum tunneling" at below activation energy levels or "quantum entanglement" from a distance, or follow a "quantum walk" to a molecular reaction center) to the biochemical or life processes essential for effecting beneficial downstream biological effects such as phosphorylation of specific biomolecules (e.g., phosphorylation of IKKα/β to activate NF-kB or phosphorylation of PI3K to activate Akt). These subatomic and submolecular changes which may lead to stimulation or inhibition of various biochemical pathways may be influenced by a delicate balance involving the quantum physics phenomena of quantum entanglement/quantum tunneling/quantum walk from photonic energy exchanges via the laser methodology.

LLLT, when delivered to the choroidal and retinal tissues of a patient's eyes may be essential for its regenerative properties. These nonscarring properties are critical for regeneration of diseased or defective cells. It has been demonstrated that the red He—He 632.8 nm laser can inhibit scarring. "Repeated irradiation with 180 J/cm² He—Ne laser can inhibit scar fibroblasts growth in culture. It may be that He—Ne laser irradiation causes cell stagnation in $G^0/G^1$ phase and apoptosis." (Shu B, Wu Z, Hao L, et al. Experimental study on He—Ne laser irradiation to inhibit scar fibroblast growth in culture. *Chinese Journal of Traumatology=Zhonghua Chuang Shangza zhi.* 2002 August; 5(4):246-249). "[R]epeated irradiation with a He—Ne laser at certain power densities inhibits fibroblast proliferation and collagen synthesis, thereby inhibits the growth of hypertrophic scars." (Shu B, Ni G X, Zhang L Y, et al. High-power helium-neon laser irradiation inhibits the growth of traumatic scars in vitro and in vivo. *Lasers in Medical Science*. 2013 May; 28(3):693-700). The LLLT methodology developed by Dr. Pon utilized a 630 nm-650 nm diode aiming beam along with the 810 nm infrared pulsed laser. The aiming beam is believed to have had an anti-scarring effect as part of a multi-wavelength multi-faceted approach to treatment of wet AMD and other ocular diseases without scarring.

Recent research shows that, instead of regenerating lost or injured body parts, mammals typically form a scar at the site of an injury. The scar creates a physical barrier to regeneration. As stated by Debuque et al.:

> Our research shows that humans have untapped potential for regeneration . . . . If we can solve the problem of scar formation, we may be able to unlock our latent regenerative potential. Axolotls [Mexican salamanders] don't scar, which is what allows regeneration to take place. But once a scar has formed, it's game over in terms of regeneration. If we could prevent scarring in humans, we could enhance quality of life for so many people . . . While most salamanders have some regenerative capacity, the axolotl can regenerate almost any body part, including brain, heart, jaws, limbs, lungs, ovaries, spinal cord, skin, tail and more. Since mammalian embryos and juveniles have the ability to regenerate—for instance, human infants can regenerate heart tissue and children can regenerate fingertips—it's likely that adult mammals retain the genetic code for regeneration . . . macrophages are critical to regeneration: when they are depleted, the axolotl forms a scar instead of regenerating, just like mammals . . . the signaling response of a class of proteins called toll-like receptors (TLRs), which allow macrophages to recognize a threat such an infection or a tissue injury and induce a pro-inflammatory response, were "unexpectedly divergent" in response to injury in the axolotl and the mouse . . . [modifying] TLR signaling pathways that regulate the unique immune environment enable[s] axolotl regeneration and scar-free repair.
>
> Co-exposure of macrophages to DAMPs/PAMPs [damage associated molecular pattern/pathogen associated molecular pattern] suppressed MAPK [mitogen activated protein kinase] signaling in mammals, but not salamanders, which activate sustained MAPK stimulation in the presence of endogenous DAMPS . . . These results reveal an alternative signal transduction network compatible with regeneration.

(Debuque R J, Nowoshilow S, Chan K E, Rosenthal N A, and Godwin J W. Distinct toll-like receptor signaling in the salamander response to tissue damage *Developmental Dynamics/Early View* First published: 1 Apr. 2021). Furthermore, other groups have reported that phototherapy induce[s] mitogen-activated protein kinase/extracellular signal-regulated protein kinase (MAPK/ERK) phosphorylation in these cells, probably by specific receptor phosphorylation. (Oron U. Photoengineering of tissue repair in skeletal and cardiac muscles. *Photomed Laser Surg*. 2006 April; 24(2): 111-20). The LLLT treatment developed by Dr. Pon is not only nonscarring thus permissive for regeneration but also is known to be anti-inflammatory and may also help to modify TLR signaling to allow for regeneration possibly via stimulation of the MAPK pathway signaling for regeneration, which is suppressed in mammals but not in highly regenerative Axolotls in response to DAMPs/PAMPs. The MAPK pathway is also proposed as the mechanism by which the LLLT treatment enhances immune competence.

Additionally, LLLT via differential effects on gene expression, may modify the ratio or concentrations of various soluble growth factors or cytokines important for prevention of scarring. For example, LLLT can increase TGFβ3 (transforming growth factor-beta-3), which homes mesenchymal stem cells (MSCs). (Deng M, Mei T, Hou T, et al. TGFβ3 recruits endogenous mesenchymal stem cells to initiate bone regeneration. Stem Cell Research & Therapy. 2017 November; 8(1):258). As reported by Ferguson et al., "Skin wounds on early mammalian embryos heal perfectly with no scars whereas wounds to adult mammals scar . . . [E]mbryonic wounds that heal without a scar have low levels of TGFβ1 and TGFβ2, low levels of platelet-derived growth factor and high levels of TGFβ3. We have experimentally manipulated healing adult wounds in mice, rats and pigs to mimic the scar-free embryonic profile, e.g. neutralizing PDGF, neutralizing TGFβ1 and TGFβ2 or adding exogenous TGFβ3. These experiments result in scar-free wound healing in the adult . . . [B]oth repair with scarring and regeneration can occur within the same animal, including man, and indeed within the same tissue . . . by subtly altering the ratio of growth factors present during adult wound healing, we can induce adult wounds to heal perfectly with no scars, with accelerated healing and with no adverse effects . . . " (Ferguson M W J and O'Kane S. Scar-free healing: from embryonic mechanisms to adult therapeutic intervention. *Phil. Trans. R. Soc. Lond*. B (2004) 359, 839-850).

Therefore, the complexities of LLLT effects may involve the upregulation of TGFβ3 and TGFβ1 by red light (650 nm Iridex Oculight Slx aiming beam) while the increased TGFβ1 effects were being contemporaneously offset or reversed by the infrared (810 nm) laser (offset is maximal at the lowest energy density), resulting in a net increase in TGFβ3 to TGFβ1 ratio. In turn, this new elevated TGFβ3 [which homes MSCs for regeneration] on balance, allows non-scarring healing to occur. The lack of scarring then is permissive for regeneration with its observed benefits.

Advantages of LLLT Treatment for AMD Compared to Alternative Treatments.

One significant manner in which the LLLT treatment for AMD developed by Dr. Pon was superior to the prior art use of anti-VEGF agents was that the non-scarring LLLT had no serious side effects. In contrast, known side effects associated with the use of anti-VEGF agents include increased rates of heart attack, stroke, infection, cognitive decline, nephrotoxicity, and death. Every eye has VEGF (unless blocked by anti-VEGF agents) which normally serves some physiologic purpose in the normal state such as neurotropic effects. By complete VEGF blockade, normal physiological functions are defeated and adverse effects may result from this unbalanced altered state. Effective anti-VEGF treatment requires burdensome repeated intravitreal injections and follow-up as often as monthly intervals over a period of many years (10-year studies of long term ongoing anti-VEGF treatments have been reported). The more serious documented adverse effects include hospitalizations as high as 24.1%. "[S]erious systemic adverse events (primarily hospitalizations) was higher with bevacizumab [Avastin] than with ranibizumab [Lucentis]" (24.1% vs. 19.0% . . . (p<0.04), although a direct causal link is unclear. (National Eye Institute: CATT Research Group, 2011). Other serious adverse effects include ocular complications resulting in documented blindness (e.g., endophthalmitis, sterile intraocular inflammation, retinal detachment), cognitive decline, heart attack, stroke, thromboembolic events, and even death. Intravitreal use of Anti-VEGF agents despite its small injection quantity is documented to have increased mortality (>2-fold increase) after prior MI or stroke (Chen Y Y, et al. Increased mortality after intravitreal injections [IVI] of anti-VEGF for neovascular AMD [nAMD] among patients with prior stroke or acute myocardial infarction [AMI]. *Eye* (*Lond*). 2021 Mar. 2), nephrotoxicity by prompting decreased protective inhibitory complement factor H (Keir L S, Firth R, Aponik L, et al, VEGF regulates local inhibitory complement proteins in the eye and kidney. *J Clin Invest.* 2017; 127(1):199-214; Hanna R M, Barsoum M, Arman F, Selamet U, Hasnain H, Kurtz I. Nephrotoxicity Induced by Intravitreal Vascular Endothelial Growth Factor Inhibitors: Emerging Evidence. *Kidney Int.* 2019: 96: 572-580; Shye M, Hanna R M, Patel S S, Tram-Tran N, Hou J, Mccannel C, Khalid M, Hanna, M, Abdelnour L, Kurtz I. Worsening Proteinuria and Renal Function after Intravitreal Vascular Endothelial Growth FactorBlockade forDiabetic Proliferative Retinopathy. *Clin. Kidney J.* 2020:13: 969-980), as well as possible increased cognitive impairment (Krader C G. Study results link frequent anti-VEGF injections, risk of cognitive impairment. *Digital Edition, Ophthalmology Times*: Nov. 1, 2020, Volume 45, Issue 18, Dec. 11, 2020).

In contrast, LLLT for AMD does not have any serious adverse effects. In addition to improved contrast sensitivity, subsequent research has confirmed that visual acuity, color vision, and central scotoma improve with the use of LLLT, that it can be used both curatively and preventively to preserve eyesight," and repeated as frequently as needed. (Ivandic T. Low-Level Laser Therapy. *Dtsch Arztebl Int* February 2021; 118: 69). The systemic effects of anti-VEGF drugs have been well documented in the scientific literature as well as on the FDA package insert when even a small dose of Avastin (e.g. 1.25 mg) is used intravitreally. (A 1.25 mg Avastin intravitreal dose is 200-fold less dosage than the 5 mg/kg Avastin intravenous dose for a 50 kg patient).

Another advantage of LLLT treatment for AMD relative to other known treatments is that it a substantially less expensive alternative. The pulsed subthreshold laser treatments were not only effective, restorative, non-scarring, safe, without any significant side effects, and longer lasting, but also cost-saving over the alternative of bearing the treatment burden of indefinitely recurring frequent (monthly to bimonthly) drug injections injected directly into the eye. Newly Discovered Advancements.

While the work toward development of AMD diagnosis and AMD treatment protocols and techniques as discussed above was directed to the reversal of the progression of AMD and other ocular diseases, including restoration of improved eyesight and healing/regeneration of ocular tissues, Dr. Pon has also made the surprising discovery that the healing/regenerative effects of the pulsed LLLT treatment applied to ocular tissues are not limited to the tissues actually irradiated with the electromagnetic energy or immediately adjacent tissues, and are not limited to healing/regeneration of ocular tissues. Rather, he has discovered that administration of electromagnetic energy to ocular blood vessels by way of a laser or LED or other photon-emitting device, and in particular pulsed LLLT treatment administered to blood vessels in a patient's eye, has beneficial remote effects in other parts of the patient's body. As used herein, the term "remote" is intended to refer to biological tissues and cells outside the patient's eye, that is, "non-ocular tissues." In accordance with this new discovery LLLT applied into a patient's eye has beneficial and even "curative" effects for many non-ocular conditions. Without intending to be limited by any theory, it is believed that these remote beneficial effects are achieved via hematogenous, immunologic and/or optoneuroendocrine dissemination. The non-ocular conditions or disorders that are treated in accordance with this disclosure include, but are not limited to cancers, such as, for example and without limitation, solid, soft tissue, and hematological malignancies (such as, for example and without limitation, multiple myeloma, breast, ovarian, colon, renal cell, thyroid cancers, head and neck cancer, squamous cell carcinoma and melanoma), breast cancer related lymphedema, heart disease, hypertension, metabolic/endocrine disorders, diabetes mellitus, diabetic foot ulcers, diabetic neuropathy, cerebrovascular disorders, spinal cord injuries, obesity, dyslipidemia, liver disease, renal disease, traumatic brain injury, dermatologic disorders (such as, for example and without limitation, acne vulgaris, alopecia and skin wrinkles), infections such as, for example and without limitation, fungal infections, drug-resistant infections, microbiome related disorders, body system disorders (including, for example, and without limitation, immunity, metabolic, obesity, inflammatory, cardiovascular and neurodegenerative disorders), immune/complement system disorders, dental disorders, oral mucositis, memory disorders, psychiatric disorders, musculoskeletal disorders such as, for example, and without limitation, carpal tunnel syndrome, rheumatoid arthritis, osteoarthritis, tendinopathy, shoulder injuries, muscle spasms, myofascitis, chronic joint disorders and fibromyalgia, bone disorders, osteoporosis, neurodegenerative diseases, such as, for example and without limitation, multiple sclerosis, Parkinson's disease, Alzheimer's disease and amyotrophic lateral sclerosis, excess subcutaneous adiposity, wound healing, poor exercise performance issues, sperm motility and velocity issues, chronic pain, such as, for example and without limitation, chronic neck and lower back pain, tendonitis, chronic joint disorders, temporomandibular joint pain-dysfunction syndrome, trigeminal neuralgia, postherpetic neuralgia, and diabetic neuropathy, inflammatory disorders (e.g., arthritis, gingivitis), pulmonary disorders, e.g. COVID-19/acute respiratory distress syndrome (ARDS)/cytokine storm, other degenerative aging disease and other systemic disorders or such disorder(s) one may be at increased risk of developing. As discussed further below, this disclosure also contemplates use of the disclosed methods to enhance health even in the absence of a specific disorder or disease, such as, for example, by improving or enhancing hair regrowth, subcutaneous adipose tissue reduction, exercise performance and homeostasis, and by reducing the effects of aging. For optimal effectiveness, LLLT may be delivered as combination therapy with other modalities and may be provided alongside, or even replace traditional medical treatments.

Without intending to be limited to any theory by which the disclosed systems and methods achieve their beneficial results, it is believed that, LLLT treatments as described herein, applied to the ocular tissues of the eye, which are highly vascularized, and in particular when the photonic energy is delivered to ocular blood vessels such as choroidal feeding vessels, other choroidal blood vessels and retinal blood vessels, whether delivered from a focal laser beam or a grid laser delivery that delivers photons into contact with ocular blood vessels, deliver energy that stimulate cells or biomolecules within the patient's eye and/or within the patient's bloodstream to undergo conformational, functional or energy state changes. When these cells or biomolecules, or other products are activated, energized, or produced by such cells or by changes to such biomolecules, are conveyed to other tissues in the patient's body, i.e., remote tissues or non-ocular tissues, including those that are affected by disease, through the patient's circulatory system via the choroidal vasculature, they impart a beneficial effect, such as a healing or regenerative effect, on such remote tissues.

The direct photonic energy delivery to the ocular vasculature through the clear media of the eye (cornea, aqueous, lens, vitreous, retina) for treatment of non-ocular systemic disease in accordance with this disclosure is possible because blood vessels in the eye are the only blood vessels that can be directly visualized and irradiated noninvasively. The method utilizes delivery through the optically clear and transparent media of the ocular tissues through the transparent retina directly into the vasculature with less reflection, refraction, scattering, or absorption by tissues. Blood vessels can take different forms throughout different tissues in the body. However, only via the transparent tissues of the eye can light penetrate directly into the vasculature and into the highly efficient circulation of the choroid noninvasively. The choroidal thickness in the subfoveal region is greatest and varies between 250 to 330 microns but thinner with certain diseases (e.g. AMD) and with age and increased axial length and thicker (pachychoroid) in other conditions. (Chhablani and Ruiz-Medrano, 2017). The choroidal circulation which supplies the choriocapillaris-RPE complex and outer retina can be directly visualized with ICG angiography. Since the retina is transparent, it can be directly targeted by laser which only needs to penetrate a single cell layer of pigmented cells (RPE) which is ~10-20 microns thick but which would absorb some pulsed low level laser energy which may itself result in some beneficial biological response as has been noted in multiple retinal diseases such as in LLLT/PBM for dry and wet AMD, central serous chorioretinopathy, diabetic macular edema, branch or central vein occlusive macular edema. Once the laser penetrates the transparent retina and the RPE, it reaches the relatively large-caliber capillaries (10-40 microns diameter) in the choriocapillaris (10-12 microns thick at the macula, 6-7 peripherally) which are lined by fenestrated (toward the retina) endothelium. The choriocapillaris density may decrease by as much as 54% with age. Then the laser would reach the larger choroidal vessels which may be feeding an area of incipient neovascularization via penetrating vessels (Flower et al, 2001) and then the Sattler layer and the Haller layer of choroidal vessels. The choroidal circulation is the most rapid in the body per unit weight and thus the photonic energy can be rapidly transmitted locally as well as systemically. In the brain, the primary photoacceptor for infrared light is the hemoglobin in the circulation.

The discoveries leading to this invention were made based on actual observations of non-ocular effects in patients treated with the pulsed LLLT treatment described herein, as further described in the Examples below. More specifically, the present inventor has made the surprising discovery that multiple patients who were treated for AMD, retinopathy or other eye disease using pulsed LLLT as described herein not only experienced improvements to their eyesight, regression of their eye disease and regeneration of ocular tissues, but they also experienced other indicia of improved health beyond the eye, including reduced effects of other, non-ocular, diseases for which such patients were being treated under the care of other physicians, or other health improvements. Further research has revealed that this pioneering pulsed LLLT treatment method is effective to treat and reduce myriad remote and/or systemic disorders, and decrease, reverse, or even eliminate aging changes such as decreased ATP production, shortening of telomeres, or cellular senescence, as well as rejuvenate and improve the immune system and regenerate diseased cells and tissues.

LLLT takes advantage of the optical transparency in the ocular system allowing photons direct access without scatter to the highest blood flow vasculature per tissue weight in the body. Then the photonic energies are transferred hematogenously via endogenous (e.g., soluble protein mediators, erythrocytes, leukocytes) or even exogenous (e.g., photosensitive dyes or pharmaceuticals) chromophores. Soluble chromophores may operate as mediators to mobilize quantized energy to target tissues via single-, two- or multi-photon absorption and transfer for local and/or systemic dissemination. While the treatments described herein do not damage ocular tissues and do not induced scarring that has a negative impact on a patient's vision, to avoid inadvertent injury to ocular tissues that can occur by accident or unanticipated effects, the electromagnetic energy is preferably aimed to an ocular tissue that is outside the macula and preferably peripheral to the equator, such as a non-central choroidal blood vessel that lies outside the normal field of vision.

While it is not intended that this disclosure be limited by any theory whereby it achieves its advantageous results, it is believed that the effect is achieved via one or more biological mechanisms that are stimulated by the pulsed, non-scarring, subthreshold LLLT and then transmitted systemically to other biological tissues in the patient's bloodstream, for example, such as via a mechanism of transmission of photonic effects by SPMs [soluble protein mediators] released from the immune system. While not intending to be bound by an theory whereby the present disclosure achieves its beneficial results, it is believed that the non-ocular effects of the methodology may be mediated via one or more mechanism including but not limited to hematogenous mediators, immunologic mediators, cytokine mediators, soluble protein mediators, extracellular and/or intracellular biophotonic energy transfer, mitochondrial stimulation, increased ATP production, increased mitochondrial membrane potential (MMP), opto-neuroendocrine via melatonin, protein conformational modification, extracellular nanoparticle or vesicular transfer of mRNA, microRNA, proliferating cell nuclear antigen ("PCNA"), molecular cascades including mitochondrial respiratory chain molecules, reactive oxygen species, nitric oxide, enhanced DNA repair gene expression, genomic stabilization, PI3K/AKT/mTOR, MAPK/ERK, heat shock proteins, insulin sensitivity, local redox microenvironment, Dok1/ERK/PPARγ, Dok-1/PD-L1, DOK1/activin receptors/Smad/MAP kinase/Bcl-XL/ apoptosis and ICG green dye mediation. With regard to mitochondrial stimulation, increased ATP production and MMP, it is generally understood that the retina has the greatest energy demand in the body because of the high metabolic rate of photoreceptors, which are rich in mitochondria. Thus, delivery of photonic energy to the choroidal and retinal tissues as described herein is believed to improve mitochondrial respiration, increasing their membrane potentials and improve ATP production. With regard to systemic effects of LLLT involving the immune system, modulation of inflammation and SPMs such as cytokines, it is understood that the main cellular components of the immune system are lymphocytes and macrophages. Photons can be absorbed by immune cells in transit through the superficially located blood and lymph capillaries and phototherapy can have a direct effect on the secretion of SPMs by these cells. The effectiveness of LLLT to treat inflammation may result from attenuating production of reactive oxygen species (ROS) by neutrophils.

Serious adverse effects after LLLT have not been reported even after 5 decades of clinical LLLT use. After treatment, Dr. Pon's patients were helped well beyond their expectations, not only by improvement of vision and reversal of eye disease, but also by improving and reversing concurrent non-ocular disorders. Moreover, it is believed that the higher intensity laser treatment in Phase II of the treatment protocol for AMD described above is not required in order to achieve the advantageous results described herein in the treatment of non-ocular diseases/disorders. Therefore, the present disclosure contemplates that the treatment protocol for a non-ocular disease/disorder includes only pulsed LLLT treatment that does not cause any adverse reaction to the ocular tissues being treated.

Accordingly, an aspect of the present disclosure is a method for ameliorating a non-ocular disease/disorder in a subject that includes (i) selecting a patient based on a diagnosis for a non-ocular disease/disorder; and (ii) responding to the diagnosis by delivering pulsed electromagnetic energy to at least one ocular blood vessel of the patient to ameliorate at least one symptom of the non-ocular disease/disorder. The pulsed electromagnetic energy in certain embodiments comprises visible laser/light including visible light radiation, redlight radiation, infrared radiation, near infrared radiation or a combination of wavelengths in the visible, infrared and/or near infrared spectrum, and can also comprise other forms of laser or LED treatment, all of which are referred to herein as "pulsed LLLT treatment" herein. The electromagnetic energy is preferably aimed toward an ocular blood vessel selected from a retinal blood vessel and a choroidal blood vessel. In certain preferred embodiments, the electromagnetic energy is aimed toward a choroidal blood vessel, such as a choroidal feeding vessel, preferably one that lies outside the patient's normal field of vision. In the course of a treatment session, electromagnetic energy can be delivered to multiple ocular sites, such as multiple sites along a single ocular blood vessel and/or to sites on multiple different blood vessels. For example, a single session may include delivery of electromagnetic energy to from about 1 to about 10 ocular sites, or in a case in which a grid pattern is employed, a single session may include delivery of electromagnetic energy up to 500 or more ocular sites. In preferred embodiments, the sites are selected to avoid the fovea and the disc.

With regard to parameters used for the pulsed LLLT treatment, in certain embodiments, the laser parameters are initially set at very low fluence in micropulse mode. For example, in some embodiments, the laser parameters are initially set at between 0.059 $J/cm^2$ to 4,200 $J/cm^2$ of fluence per train of micropulses at 500 Hz with the power set at from about 25 mW to about 100 mW.

The laser delivery instrument may be set up to deliver electromagnetic energy at a wavelength of 810 nm (infrared) along with a nominal red aiming beam set at a wavelength of 650 nm or may in other embodiments be set up to deliver electromagnetic energy and one or more other wavelengths. In still other embodiments, the LLLT treatment can be delivered from any other type of laser or LED or other photon-emitting device. In one embodiment, a LLLT laser treatment is begun in the micropulse mode with the micropulse duty setting at about 5% and may be adjusted incrementally between about 5% and about 15% over a period of time from about 1 minute to about 15 minutes. The duty cycle, or micropulse duration, or micropulse interval can be adjusted lower or higher as appropriate to adjust the repetition frequency so long as it is not increased to a level that causes any visible tissue reaction. In some embodiments, the laser settings are gradually adjusted to achieve LLLT effects without scarring by gradually increasing the power or adjusting other parameters in stepwise increments such as duty cycle or micropulse duration or micropulse interval, or spot size, or exposure duration, or exposure interval, or 650 nm red aiming beam intensity, while still not causing any tissue damage or scarring. Parameters of the laser delivery instrument that can be adjusted incrementally during the course of the treatment include, for example, when in micropulse mode, the power of the beam, which can for example initially be set at a power of 50 mW, exposure interval, which can for example initially be set at single pulse or no repeat, micropulse duration, which can for example be set at 0.1 ms, micropulse interval 1.9 ms. During the course of the treatment, which can last, for example, for about 1 minute to about 15 minutes per phase, these parameters can also be adjusted incrementally stepwise up to, for example a power of about 2000 mW with micropulse duration set at about 0.3 ms, and exposure interval set at about 1.7 ms. It is to be understood that these adjustments are within the discretion of the operator and can be balanced to achieve pulsed delivery of photons to the target ocular tissue so long as no parameter is increased to a level that causes visible tissue reaction. Should the operator observe any visible tissue reaction, the parameters should be adjusted to reduce the irradiance to a level that avoids any further tissue reaction. Moreover, if a visible tissue reaction is observed, pulsed treatment can be applied to the affected tissue with lower irradiance to prevent scarring of such tissue and to promote healing and regeneration of the tissue following conclusion of the treatment.

The slit lamp adapter (SLA) delivery spot size can be changed to from 75 microns to 125 microns or to 200 microns or higher up to, for example, 5000 microns, and the micropulse duration adjusted down toward 0.1 msec or the micropulse interval increased toward 10.0 ms to lower the irradiance even further especially if there appears to be more prominent pigmentation in the immediate area being treated. All the laser parameters are variable during the course of the treatment and are dependent on a number of factors such as, for example, the diameter of the feeding vessel being treated, the amount of localized pigmentation in the target tissue, localization of the area of increased retinal thickness (ORL), the precise instantaneous reaction to treatment, as well as patient cooperation and other variables.

The LLLT procedure itself may next take as long as 50 minutes or even 60 minutes in certain cases depending on the degree of ocular pigmentation, number of ocular blood vessels treated as well as the individual response to each pulse and to patient cooperation. Adequate time for "rest" between laser pulses and trains of laser pulses (micropulse, nanopulse) needs to be provided to allow for "rebalancing" molecular homeostasis and vibratory equilibrium. With this caveat, which takes experience along a steep learning curve, during the LLLT treatment, when at low temperature and in micropulse mode, the controlled elevation in temperature can be continued as needed and in proximity to the absorbing chromophores. Thus, one would not see blanching because the irradiated tissues do not have enough thermal conduction to affect the retina's transparency.

At the conclusion of the procedure, if desired, such, as, for example if the treatment session was relatively long, a drop of ketorolac tromethamine 0.4% (Acular® LS, Allergan, Inc, Irvine, CA, USA) may be placed in the treated eye on an as-needed basis to address any discomfort; however, there is usually little to no discomfort after the procedure when ketorolac is not used. Rarely, an epithelial defect may arise after using the contact lens even with methylcellulose gel applied especially if the procedure is lengthy, and in this case, a bandage contact lens or patch may be placed overnight.

While significant benefits can be achieved in a single PULSAR™ (LLLT) treatment as described above, the present disclosure also contemplates treatment of a patent in multiple such sessions spaced out over time, and a regular series of treatments provides ongoing, and perhaps additive, beneficial effects. For example, depending on various circumstances, a patient can be treated once per month, once every two months, once every three months, or the like, or on different schedules spaced apart by lesser or greater periods of time. Because the PULSAR™ (LLLT) treatment does not cause physical injury to the patient's ocular tissues and does not cause scarring, subsequent treatments can be performed as often as desired. Moreover, subsequent treatments can deliver electromagnetic energy to the same ocular sites as a prior treatment, to different sites or both.

As discussed above, it is believed that pulsed LLLT achieve its beneficial effects on remote (i.e., non-ocular) tissues via one or more of several biological pathways/mechanisms. For example, one such pathway is the stimulatory effect that LLLT has on mitochondria, the powerhouse organelles within cells (especially found in photoreceptors) to produce ATP (adenosine triphosphate), which is known as "the energy molecule." The complex process of oxidative metabolism takes places via the electron transport chain (ETC) in which cytochrome c oxidase in thought to be the primary acceptor of the photonic energy along the mitochondrial inner membrane where ATP is produced. This mechanism is accompanied by the production of reactive oxygen species (ROS). ROS levels are thought to be hormetic in which there can a delicate balance of beneficial biostimulatory effects at lower levels and inhibitory biologic effects at higher levels. The optimal laser parameters are reached within the range obtained by the stepwise increments of the PULSAR™ laser methodology.

Another such pathway is the enhancement of phosphorylation of PI3K (phosphatidylinositol-3-kinase), Akt (protein kinase B), and mTOR (mammalian target of rapamycin) by LLLT. In a recent study by Yue Li, et al., the inhibitor for the PI3K/Akt axis was used to verify the involvement of PI3K/Akt signaling pathway. The obtained results suggested that the inhibition of the PI3K/Akt signaling pathway attenuated the effects of LLLT on proliferation, migration, and angiogenesis of human umbilical vascular endothelial cells (HUVEC), demonstrating that LLLT promotes the proliferation, migration, and angiogenesis of HUVECs via activation of the PI3K/Akt signaling pathway. (Li Y, Xu Q, Shi M, Gan P, Huang Q, Wang A, Tan G, Fang Y, Liao H. Low-level laser therapy induces human umbilical vascular endothelial cell proliferation, migration and tube formation through activating the PI3K/Akt signaling pathway. *Microvasc Res.* 2020: 129:103959)

Another such mechanism is stimulation of telomerase activity. Telomerase is an enzymatic ribonucleoprotein complex that acts as a reverse transcriptase in the elongation of telomeres. Somatic cells without telomerase activity exhibit a limited replicative capacity and after a finite number of cell divisions reach a state known as replicative senescence that can be abrogated by ectopic telomerase expression. Telomere maintenance is required for the complete replication of DNA and protection of chromosomes from nuclease degradation, end-to-end fusion, and cellular senescence. Shortening of telomeres (DNA protective endcaps) during normal cell division is counteracted by the cellular enzyme telomerase. In human beings, telomere shortening is a potential prognostic marker for disease risk and progression and for premature death, and it has been reported that cellular aging conferred by diminished telomere maintenance seems to be a precursor to the development of many types of cancer, increased risk of prostate cancer recurrence after radical prostatectomy, increased risk of coronary heart disease (shortened survival) and increased risk of infectious diseases. Short telomere length in peripheral blood mononuclear cells (PBMCs) has been reported to be associated with aging and aging related diseases, such as cancer, stroke, vascular dementia, cardiovascular disease, obesity, osteoporosis, and diabetes.

Relatedly, in prior studies, telomerase-deficient mice did not show any noticeable defects during the early generations of intercross between deficient mice; however, late-generation animals show phenotypes, including short telomere length (TL), reduced ability for stress response, progressive tissue atrophy, shortened lifespan, and notably, spontaneous malignancies. Cells that are unable to produce telomerase approach cellular senescence earlier and exhibit a significantly higher rate of malignant transformation than control cells. Recent research by Sun, et al., demonstrated that telomerase has a protective role in buffering senescence stresses due to short, dysfunctional telomeres, thereby preventing malignant transformation. (Sun L, Chiang J Y, Choi J Y, Xiong Z M, Mao X J, Collins F S, Hodes R J, and Cao K. Transient induction of telomerase expression mediates senescence and reduces tumorigenesis in primary fibroblasts. *PNAS* 2019:116(38):18983-18993). Other groups have documented that LLLT increases telomerase (Raafat B M, Aziz S W, Latif N A and Hanafy A M. Human Telomerase Reverse Transcriptase (hTERT) Gene Expression in Rheumatoid Arthritis (R A) Patients after Usage of Low Level Laser Therapy (LLLT) *Australian Journal of Basic and Applied Sciences* 2011 5(10): 1-8) decreases telomere shortening and maintains telomeres (da Silva Neto Trajano L A, da Silva Sergio L P, de Oliveira D S L, et al. Low-power infrared laser modulates telomere length in heart tissue from an experimental model of acute lung injury. *Photochemical & Photobiological Sciences*: Official Journal of the European Photochemistry Association and the European Society for Photobiology. 2021 May; 20(5):653-661) and delays senescence (Huang L, Wu Z, Mo H. [Experimental study of effect of low power laser on telomere length of cells]. Sheng wu yi xue Gong Cheng xue za zhi=*Journal of Biomedical Engineering*=Shengwu Yixue Gongchengxue Zazhi. 2013 June; 30(3):592-596) and thus may inhibit the development of malignancy. Thus, the non-local beneficial effects observed from the pulsed LLLT treatment described herein may be related to stimulation of telomerase activity.

Arabadjiev et al. recently reported that photobiomodulation "with appropriate parameters can delay the attrition of the telomeres and the entry of cells into senescence, suggesting a potential involvement of telomerase reactivation." (Arabadjiev B, Pankov R, Vassileva I, Petrov L S, and Buchvarov I. Photobiomodulation with 590 nm Wavelength Delays the Telomere Shortening and Replicative Senescence of Human Dermal Fibroblasts In Vitro. *Photobiomodul Photomed Laser Surg.* 2020 November; 38(11):656-660). Similarly, Odinokow and Hamblin recently reported that "New therapeutic approaches such as photobiomodulation (PBM) may reduce or reverse these ["programmed aging"] changes. PBM (also known as low-level laser therapy or LLLT) involves the delivery of non-thermal levels of red or near-infrared light that are absorbed by mitochondrial chromophores, in order to prevent tissue death and stimulate healing and regeneration . . . PBM may reverse or prevent thymic involution [a sign of aging] due to its ability to induce extrapineal melatonin biosynthesis via cyclic AMP [adenosine monophosphate] or NF-kB [nuclear factor-kappa light chain enhancer of activated B cells] activation, or alternatively by stimulating bone marrow stem cells that can regenerate the thymus . . . PBM can alter thymic involution, improve immune functioning in aged people." (Odinokov D and Hamblin M R. Aging of lymphoid organs: Can photobiomodulation reverse age-associated thymic involution via stimulation of extrapineal melatonin synthesis and bone marrow stem cells? *J Biophotonics.* 2018:11(8)).

Another possible mechanism of action for the LLLT treatment described herein is melatonin stimulation. The stimulation of melatonin by LLLT has many potential benefits. As stated by Acuña-Castroviejo et al., "The circadian production of melatonin by the pineal gland explains its chronobiotic influence . . . including the endocrine and non-endocrine rhythms. Other functions of melatonin, including its antioxidant [and pro-oxidant properties for injured and cancerous cells] and anti-inflammatory properties, its genomic effects, and its capacity to modulate mitochondrial homeostasis, are linked to the redox status of cells and tissues . . . the presence of melatonin has been detected in multiple extrapineal tissue including the brain, retina, lens, cochlea, Harderian gland, airway epithelium, skin, gastrointestinal tract, liver, kidney, thyroid, pancreas, thymus, spleen, immune system cells, carotid body, reproductive tract, and endothelial cells . . . Melatonin is present in essentially all biological fluids including cerebrospinal fluid, saliva, bile, synovial fluid, amniotic fluid, and breast milk." (Acuña-Castroviejo D, Escames G, Venegas C, Díaz-Casado M E, Lima-Cabello E, López LC, Rosales-Corral S, Tan D X, Reiter R J. Extrapineal melatonin: sources, regulation, and potential functions. *Cell. Mol. Life Sci.* 2014 DOI 10). Via this opto-neuroendocrine/immune-pineal axis/pathway, the stimulation of extra-pineal melatonin (e.g., in the retina or lens) by LLLT are believed to have remote and/or systemic beneficial effects from thymic regulation, and hematogenous or extracellular vesicular dissemination, of cytokines, growth factors, antioxidant and anti-inflammatory mediators and molecules and also have pro-oxidant effects on cancer cells.

Diabetes Mellitus

As reported in Example 1 herein, after treating a patient suffering from diabetic retinopathy with the LLLT treatment described herein, Dr. Pon learned that (i) prior to the LLLT treatment, the patient had been required to receive daily injections of 300 units of insulin due to the severity of her diabetes mellitus, and had been receiving insulin injections for many decades, and (ii) that, following the LLLT treatment, the diabetes mellitus had inexplicably resolved to the point that no further insulin injections were prescribed, with documented new onset of endogenous insulin production. Diabetes mellitus is a worldwide major health problem. The only plausible explanation for this surprising result is that the subthreshold pulsed LLLT treatment of the patient's diabetic retinopathy, including ocular vascular anomalies (specifically microaneurysms) also produced the beneficial result of restoring the patient's systemic glucose control.

Therefore, one important aspect of this disclosure is a method for ameliorating diabetes mellitus in a subject that includes (i) selecting a patient based on a diagnosis for diabetes mellitus or risk of developing diabetes mellitus; and (ii) responding to the diagnosis by delivering pulsed electromagnetic energy to at least one ocular blood vessel of the patient to ameliorate at least one symptom of diabetes mellitus. In certain embodiments, the pulsed electromagnetic energy comprises electromagnetic energy selected from infrared radiation, near infrared radiation and combinations thereof. The treatment can be, for example, any of the pulsed LLLT treatment embodiments described herein.

Insulin resistance is a hallmark of the metabolic syndrome and type 2 diabetes. Increased plasma FFA level is an important cause of obesity-associated insulin resistance. Over-activated ERK is closely related with FFA release from adipose tissues in patients with type 2 diabetes. Research has shown that low power laser irradiation in an experimental model suppresses excessive lipolysis of insulin-resistant adipocytes by activating tyrosine kinases-1(Dok1)/ERK/PPARγ pathway, that LPLI (LLLT) inhibits ERK phosphorylation through the activation of Dok1, resulting in decreased phospho-PPARγ level, and that non-phosphorylated PPARγ remains in the nucleus to increase the expression of adipogenic genes, thereby reversing excessive lipolysis in insulin-resistant adipocytes. (Jiang X, Huang L, Xing D. Photoactivation of Dok1/ERK/PPARγ signaling axis inhibits excessive lipolysis in insulin-resistant adipocytes. *Cell Signal.* 2015 July; 27(7):1265-75).

Another team demonstrated in a murine model that "PBMT reduced blood glucose and insulin resistance, and reversed metabolic abnormalities in skeletal muscle . . . accelerated adenosine triphosphate (ATP) and reactive oxygen species (ROS) generation by elevating cytochrome c oxidase (CcO) activity. ROS-induced activation of phosphatase and tensin homolog (PTEN)/protein kinase B (AKT) signaling after PBMT promoted glucose transporter GLUT4 translocation and glycogen synthase (GS) activation, accelerating glucose uptake and glycogen synthesis in skeletal muscle . . . PBMT is also widely applied to ameliorating and curing diabetic complications, such as diabetic foot [2], diabetic periodontitis [3], and diabetic retinopathy [4]. Recent studies indicate that PBMT improves insulin sensitivity in high-fat diet (HFD)-induced mice [5, 6], reveal that PBMT ameliorates glucose and lipid metabolism disorders . . . using He—Ne laser (632.8 nm . . . [I]nsulin resistance of skeletal muscle was the earliest step in the pathogenesis of metabolic syndrome and type 2 diabetes . . . . PBMT may improve insulin sensitivity of skeletal muscle through AMP/ATP[ratio]-induced AMPK activation or ROS-induced PTEN/AKT activation in type 2 diabetes . . . " (Gong L, Zou Z, Liu L, Guo S, Xing D. Photobiomodulation therapy ameliorates hyperglycemia and insulin resistance by activating cytochrome c oxidase-mediated protein kinase B in muscle. *Aging* 2021; 13(7):10015-10033).

Research models also showed PBMT controlled systemic glucose levels: "PBMT can play a very important role in the control of blood glucose levels, and its possible mechanism of action is the induction of greater muscle glycogen synthesis independently of physical exercise." (Castro K M R, de Paiva Carvalho R L, Junior G M R, et al. Can photobiomodulation therapy (PBMT) control blood glucose levels and alter muscle glycogen synthesis? *Journal of Photochemistry and photobiology. B, Biology.* 2020 June; 207:111877).

Cancer

LLLT has been shown to have a beneficial effect on cancer treatments. As reported in Examples 4-5 herein, after treating patients suffering from AMD and/or retinopathy with the LLLT treatment described herein, Dr. Pon learned that (i) prior to the LLLT treatment, the patients were also being treated simultaneously by other medical providers for cancer, and (ii) that, following the LLLT treatment, the cancer had inexplicably resolved to the point that no further treatments were necessary and without recurrence of the cancer.

The only plausible explanation for this surprising result is that the subthreshold pulsed LLLT treatment of the patient's AMD and/or retinopathy also produced the beneficial result, alone or in combination with the cancer treatments, of resolving the patient's cancer.

Therefore, one important aspect of this disclosure is a method for treating cancer in a subject that includes (i) selecting a patient based on a diagnosis for cancer or risk of developing cancer; and (ii) responding to the diagnosis by delivering pulsed electromagnetic energy to at least one ocular blood vessel of the patient to treat the cancer. In certain embodiments, the pulsed electromagnetic energy comprises electromagnetic energy selected from visible radiation, infrared radiation, near infrared radiation and combinations thereof. The treatment can be, for example, any of the pulsed LLLT treatment embodiments described herein.

While not intending to be limited to any theory whereby this treatment achieves its beneficial result, it is believed that the effect may occur via a mechanism of transmission of photonic effects by soluble protein mediators ("SPMs") released from the immune system which are factors in the abscopal effect seen in regression of distant metastatic cancer after localized cancer radiotherapy.

Research has demonstrated that SPMs such as cytokines and growth factors released from peripheral immune cells in response to the direct action of photons can be transported to cells that have not been exposed to photons. Injuries other than those directly exposed to photons can be affected by them indirectly. Cells can therefore be affected indirectly by photons without the need to actually absorb the photons.

Researchers have shown that laser immunotherapy is a promising cancer treatment method that induces antitumor immunity. The success of any immunotherapy treatment depends on the balance between the local immunosuppressive forces induced by the tumor and the immune response of the host organism. Factors that influence this balance include heat-shock proteins (for example HSP70), transforming growth factor β (TGF-β), tumor necrosis factor α (TNF-α), interleukins, and more. Laser phototherapy applied directly to tumors, which is based on non-thermal photobiological processes, has been shown to modulate the body's own immune response, both locally and systemically, with a strong influence on, for example, cytokine production and heat-shock protein synthesis. As stated by Hode et al., "Laser phototherapy may therefore be an important component in the overall efficacy of laser immunotherapy, and may tip the balance between the immunosuppressive and immunostimulatory forces in favor of immunostimulation." (Hode T and Hode L. Possible role of laser phototherapy in laser immunotherapy. *Proc. SPIE* 7178, *Biophotonics and Immune Responses IV,* 2009: 71780B).

Combination laser therapy with external adjuvants can boost host defenses non-specifically. "It has long been established that exogenous immunostimulants can enhance the host defense system . . . when the non-specific immunological enhancement is combined with other direct intervention, the immune responses could be turned to be tumor-specific. Glycated chitosan (GC), a specially designed immunoadjuvant, has been used in combination with phototherapy for cancer treatment with promising outcomes in animal studies . . . When used by itself, GC was not toxic to normal cells as well as to tumor cells. When GC was incubated with macrophages, it could induce significant secretion of TNFα. Furthermore, when GC was used with laser irradiation, it has significantly enhanced tumor cell destruction and immune responses." (Chen W R, Sarker A, Liu H, Naylor M F, and Nordquist R E Effects of immunostimulants in phototherapy for cancer treatment. *Proc. SPIE Biophotonics and Immune Responses IV,* 2009: 7178: 71780A).

A possible mechanism of action of pulsed LLLT treatment in the treatment of cancer is by activation of Dok1 (docking protein-1). Research has shown that Dok1 "displays tumor suppressor effects" (Siouda M, Yue J, Shukla R, et al. Transcriptional Regulation of the Human Tumor Suppressor DOK1 by E2F1. *Molecular and Cellular Biology* 2012; 32(23):4877-4890) and "can be up-regulated by ligands for nuclear "hormone" receptors, including PPARγ-agonists. (e.g., rosiglitazone [Avandia], [high-fat diet], retinoic acid . . . and dexamethasone . . . " (Li T, Li B, Sarab A et al, Docking protein-1 promotes inflammatory macrophage signaling in gastric cancer. *Oncoimmunology* 2019; 8 (11): e1649961). Dok1 also inhibits PD-L1 (programmed death-ligand-1), an immune checkpoint protein that blocks the immune system from destroying cells (including cancer cells). It is proposed that its activation may be useful as immunotherapy in the treatment of cancer. Thus, LLLT may activate a natural check point inhibitor (DoK1) to combat cancer analogous to the FDA approved check point inhibitor cancer immunotherapy (anti-PD-1, anti-PD-L1) drugs (e.g., Keytruda). It has also been noted that "DOK1 gene expression was repressed in a large proportion of head and neck cancer (HNC), lung, liver, and gastric cancers, and Burkitt's lymphoma as a result of aberrant hypermethylation of the DOK1 promoter region [and] DOK1 mediates activin-induced apoptosis via the activin receptors/Smad axis by suppressing MAP kinase activation and inhibiting Bcl-XL expression" (Siouda et al, 2012).

The increased PEDF caused by laser may also have anti-cancer properties. In multiple myeloma, the second most common hematologic cancer VEGF is not only angiogenic in the bone marrow, but also "directly stimulate[s] the proliferation and survival of multiple myeloma cells . . . [P]igment epithelium-derived factor (PEDF) has anti-angiogenic and anti-vasopermeability properties both in cell culture and animal models by counteracting the biological actions of VEGF . . . PEDF, a glutathione peroxidase mimetic, ebselen, or an inhibitor of NADPH oxidase, diphenylene iodonium significantly inhibited the VEGF-induced reactive oxygen species (ROS) generation, increase in anti-apoptotic and growth-promoting factor, myeloid cell leukemia 1 (Mcl-1) expression, and proliferation in U266 myeloma cells. VEGF blocked apoptosis of multiple myeloma cells isolated from patients, which was prevented by PEDF. PEDF also reduced p22phox levels in VEGF-exposed U266 cells . . . . PEDF could block the VEGF-induced proliferation and survival of multiple myeloma U266 cells through its anti-oxidative properties via suppression of p22phox, one of the membrane components ofNADPH oxidase. Suppression of VEGF signaling by PEDF may be a novel therapeutic target for multiple myeloma." (Seki at al, 2013). This mechanism can be very important because it has been demonstrated that laser (at LLLT levels) increases PEDF as much as 33-fold higher than control within 24 hours. (Ogata N, Tombran-Tink J, Jo N, Mrazek D, Matsumura M. Upregulation of pigment epithelium-derived factor after laser photocoagulation. Am J Ophthalmol. 2001 September; 132(3):427-9). Research has confirmed both suprathreshold and subthreshold laser's effect on increasing PEDF. For examples: "Suprathreshold laser treatment did not induce changes in angiogenic genes associated with neovascularization. Instead pigment epithelium-derived factor, an antiangiogenic factor, was upregulated" (Vessey K A, Ho T, Jobling A I, Mills S A, Tran M X, Brandli A, Lam J, Guymer R H, Fletcher E L. Nanosecond Laser Treatment for Age-Related Macular Degeneration Does Not Induce Focal Vision Loss or New Vessel Growth in the Retina. Invest Ophthalmol Vis Sci. 2018 Feb. 1; 59(2):731-745.), and "SDM [subthreshold diode micropulse laser, a LLLT] treatment of the RPE cells suppressed the expression of choroid neovasculization[sic]-promoting cytokines and up-regulated the angiogenic inhibitor, PEDF without damaging the cells." (Li Z, Song Y, Chen X, Chen Z, Ding Q. Biological Modulation of Mouse RPE Cells in Response to Subthreshold Diode Micropulse Laser Treatment. Cell Biochem Biophys. 2015 November; 73(2):545-552.).

Furthermore, "Reactive oxygen species (ROS) have been associated with prostate cancer development through increasing cell proliferation and metabolism [2,3]. Elevated levels of ROS are observed in breast cancer, ovarian cancer and colon cancer . . . There are many cellular systems generating ROS such as NADPH oxidase, mitochondrial electron chain and xanthine oxidase [7-11]. The NADPH oxidase (NOX) consists of a membrane-bound complex (subunit NOX isoform and p22phox) and four cytosolic subunits (p47phox, p67phox, p40phox and the small GTPase RAC) [12,13]. The transmembrane subunit p22phox forms a mutually stabilizing complex with NOX isoform . . . followed by the recruitment of cytosolic subunits to form an active complex." (Li Q et al, 2013) It was shown that, "The NADPH oxidase subunit NOX1 was also elevated in prostate cancer cells, and was involved in activation of AKT/ERK/HIF-1/VEGF pathway and regulation of cell proliferation. Knockdown of p22phox resulted in inhibition of tumor angiogenesis and tumor growth . . . A few studies showed that p22phox is overexpressed in renal cell carcinoma [22], anaplastic thyroid carcinoma [23] and melanoma [16]. In human melanoma, using targeted approaches against p22phox displayed reduced cell proliferation, supporting a role of p22phox in mitogenic signaling." (Id).

It has been demonstrated that LLLT can suppress NADPH oxidase activity. (Bathini M, Raghushaker C R, Mahato K K. The Molecular Mechanisms of Action of Photobiomodulation Against Neurodegenerative Diseases: A Systematic Review. Cell Mol Neurobiol. 2020 Dec. 10. doi: 10.1007/s10571-020-01016-9. Epub ahead of print. PMID: 33301129.). One mechanism for LLLT's anti-cancer properties may be that LLLT via elevation of PEDF counters the p22phox/NOX1 subunit of NADPH oxidase and thereby inhibits the proliferation of multiple cancers (multiple myeloma, breast, ovarian, colon, renal cell, thyroid cancers, and melanoma). "Tumor angiogenesis is required for tumor growth and metastasis since tumors cannot grow without nutrients and oxygen when their diameters are beyond 1-2 mm." (Id). VEGF which is increased by NADPH oxidase produced ROS has been shown to be required for tumor growth and vascularization in ovarian cancer, prostate cancer, and melanomas. (Id). There is also evidence for crosstalk between mitochondria and NADPH oxidase where "NOX-derived ROS increase mitochondrial ROS [13,19]; and mitochondrial ROS stimulate NOX activation [20]." (Fukai and Ushio-Fukai, 2020).

Multiple Sclerosis

As reported in Example 6 herein, after treating a patient suffering from retinal breaks in the retinal periphery with the pulsed LLLT treatment described herein, Dr. Pon learned that (i) the patient was also being treated simultaneously by other medical providers for multiple sclerosis ("MS") without success, and (ii) that, following the LLLT treatment, the multiple sclerosis symptoms had inexplicably disappeared within the same day of the pulsed LLLT treatment. While the MS symptoms slowly returned over time, the next treatment with pulsed LLLT produced the same results—complete elimination of all MS symptoms within the same date of the treatment. Multiple sclerosis is a worldwide major health problem. The only plausible explanation for this surprising result is that the subthreshold pulsed LLLT treatment applied to the patient's choroidal blood vessels also produced the beneficial result of resolving the patient's multiple sclerosis symptoms.

Therefore, one important aspect of this disclosure is a method for ameliorating the effects of multiple sclerosis in a subject that includes (i) selecting a patient based on a diagnosis for multiple sclerosis or risk of developing multiple sclerosis; and (ii) responding to the diagnosis by delivering pulsed electromagnetic energy to at least one ocular blood vessel of the patient to ameliorate at least one symptom of multiple sclerosis. In certain embodiments, the pulsed electromagnetic energy comprises electromagnetic energy selected from infrared radiation, near infrared radiation and combinations thereof. The treatment can be, for example, any of the pulsed LLLT treatment embodiments described herein.

Arthritis, Inflammatory Disease

Furthermore, research has " . . . confirmed that PBM could decrease phosphorylated levels of the phospholipase cPLA2 [Cytoplasmic[cystolic] phospholipase $A_2$] and the activity of NADPH oxidase, a major contributor to oxidative stress. cPLA2 can lead to ROS production and inflammation through the synthesis of arachidonic acid, which further paves the way for the production of leukotrienes and prostaglandins. Hence, decreased p-cPLA2 is a mechanism of the anti-oxidative and anti-inflammatory effects of PBM (Yang X, Askarova S, Sheng W, Chen J K, Sun A Y, Sun G Y, Yao G, Lee J C. Low energy laser light (632.8 nm) suppresses amyloid-β peptide-induced oxidative and inflammatory responses in astrocytes. Neuroscience. 2010 Dec. 15; 171(3):859-68. doi: 10.1016/j.neuroscience.2010.09.025. Epub 2010 Sep. 25. PMID: 20884337; PMCID: PMC2987533.) (Sun G Y, Chuang D Y, Zong Y, Jiang J, Lee J C, Gu Z, Simonyi A. Role of cytosolic phospholipase A2 in oxidative and inflammatory signaling pathways in different cell types in the central nervous system. Mol Neurobiol. 2014 August; 50(1):6-14. doi: 10.1007/s12035-014-8662-4. Epub 2014 Feb. 27. PMID: 24573693; PMCID: PMC4147031.). (Bathini et al, 2020).

Therefore, another aspect of this disclosure is a method for ameliorating the effects of an inflammatory disease, such as, for example and without limitation, arthritis, in a subject that includes (i) selecting a patient based on a diagnosis for an inflammatory disease or risk of developing an inflammatory disease; and (ii) responding to the diagnosis by delivering pulsed electromagnetic energy to at least one ocular blood vessel of the patient to ameliorate at least one symptom of inflammatory disease. In certain embodiments, the pulsed electromagnetic energy comprises electromagnetic energy selected from infrared radiation, near infrared radiation, visible radiation, or other shorter or longer wavelength radiation, and combinations thereof. The treatment can be, for example, any of the pulsed LLLT treatment embodiments described herein.

Neurodegenerative Disorders, Parkinson's Disease

LLLT utilizing near infrared light has been shown to provide neuroprotection in Parkinson's disease murine models. Researchers have demonstrated that " . . . near infrared ("NIr") light (670 nm, 4 $J/cm^2$) directed transcranially, mitigates the loss of dopaminergic cells in MPTP (1-methyl-4-phenyl-1,2,3,6-tetrahydro-pyridine)-treated mice, a model of parkinsonism. These findings complement others suggesting NIr treatment protects against damage from various insults. One puzzling feature of NIr treatment is that unilateral exposure can lead to a bilateral healing response, suggesting NIr may have 'indirect' protective effects. In addition, despite no direct irradiation of the damaged tissue, remote NIr treatment has been shown to produce a significant rescue of tyrosine hydroxylase-positive cells. Treatment of a remote tissue with NIr has also been shown to induce protection of the brain, reminiscent of the 'abscopal effect' sometimes observed in radiation treatment of metastatic cancer. "(Johnstone D M, el Massri N, Moro C, Spana S, Wang X S, Torres N, Chabrol C, De Jaeger X, Reinhart F, Purushothuman S, Benabid A L, Stone J, and Mitrofanis J. Indirect application of near infrared light induces neuroprotection in a mouse model of parkinsonism—An abscopal neuroprotective effect, Neuroscience 2014:274:93-101, 93, 94).

Neurodegenerative Disorders, Alzheimers's Disease

Through anti-inflammatory mechanisms, LLLT may also be valuable in the treatment of Alzheimer's Disease (AD). "Activation of NADPH oxidase in astrocytes and microglia results in increased production of superoxide anions, which are toxic to neighboring neurons in AD brains . . . Oxidative stress also triggers critical downstream pathways including activation of cPLA2, an enzyme responsible for membrane integrity . . . Aβ [Amyloid β] activates NADPH oxidase to induce ROS and activation of cPLA2 in primary rat astrocytes . . . Activated cPLA2, in turn, targets mitochondria, resulting in mitochondrial dysfunction and further overproduction of ROS (Zhu D, Lai Y, Shelat P B, Hu C, Sun G Y, Lee J C. Phospholipases A2 mediate amyloid-beta peptide-induced mitochondrial dysfunction. *J Neurosci.* 2006 Oct. 25; 26(43):11111-9. doi: 10.1523/JNEUROSCI.3505-06.2006. PMID: 17065451; PMCID: PMC6674660.). Yang's group demonstrated that "laser light at 632.8 nm suppressed Aβ-induced superoxide production, colocalization betweenNADPH oxidase gp91phox and p47phox subunits, phosphorylation of cPLA2, and the expressions of [pro-inflammatory factors] IL-1β [interleukin-1β] and iNOS [inducible nitric-oxide synthase] in primary astrocytes . . . 632.8 nm laser was capable of suppressing cellular pathways of oxidative stress and inflammatory responses critical in the pathogenesis in AD." (Yang et al., 2010).

Research has shown that by lowering G6PDH (glucose-6-phosphate dehydrogenase) which produces NADPH, LLLT acts with anti-oxidant activity making less NADPH oxidase (NOX) activity available to produce ROS. Investigators have found that Amyloid β, abnormally accumulated in Alzheimer's Disease, stimulates specific subunits of NOX to combine and produce ROS. LLLT inhibits this ROS production by preventing the assembly of these NOX subunits p47phox and gp91phox. (Yang et al. 2010) (Bathini et al, 2020).

Therefore, another aspect of this disclosure is a method for ameliorating the effects of a neurodegenerative disorder, such as, for example and without limitation, Parkinson's Disease or Alzheimers's Disease, in a subject that includes (i) selecting a patient based on a diagnosis for a neurodegenerative disorder or risk of developing a neurodegenerative disorder; and (ii) responding to the diagnosis by delivering pulsed electromagnetic energy to at least one ocular blood vessel of the patient to ameliorate at least one symptom of the neurodegenerative disorder. In certain embodiments, the pulsed electromagnetic energy comprises electromagnetic energy selected from infrared radiation, near infrared radiation, visible radiation, or other shorter or longer wavelength radiation, and combinations thereof. The treatment can be, for example, any of the pulsed LLLT treatment embodiments described herein.

Ischemic Heart Disease

Oron's research discovered that "Phototherapy also had beneficial effects on mouse, rat, dog and pig ischemic heart models. In these models, it was found that phototherapy markedly and significantly reduced (50-70%) the scar tissue formed after induction of myocardial infarction (MI). The phototherapeutic effect was associated with reduction of ventricular dilatation, preservation of mitochondria and elevation of HSP-70i and ATP in the infarcted zone. It is concluded that phototherapy using the correct parameters and timing has a markedly beneficial effect on repair processes after injury or ischemia in skeletal and heart muscles. This phenomenon may have clinical applications . . . LLLT to the BM (at about 20 minute's post-MI) caused a marked and significant decreased (79%) in infarct size 3 weeks post-MI. This extent of infarct size reduction was even more effective in reducing scarring than that of laser application directly to the infarcted heart . . . Even when laser was applied 4 hours post-MI to the BM of infarcted rats, a marked (52% and 42%) and significant (P<0.01) reduction in the infarcted area and in VD was observed in the laser-treated rats compared to control. We also found a significantly higher density of c-kit+ cells [MSC markers] in the myocardium of laser-treated rats relative to non-treated rats post MI. Moreover, it was demonstrated in this study that c-kit+ cells post-laser application to the BM of MI-induced rats, homed specifically in on the infarcted heart and not in on uninjured organs (i.e. liver, kidney) in the same rat. LLLT applied in the present study only to the infarcted heart did not cause a significant elevation in c-kit+ cell density in the entire LV area relative to the non-treated hearts." (Oron U. Photoengineering of tissue repair in skeletal and cardiac muscles. *Photomed Laser Surg.* 2006 April; 24(2):111-20. doi: 10.1089/pho.2006.24.111.).

In ischemic heart disease, LLLT has been experimentally documented to reduce cardiac scarring by 50-70% and infarct size by 79% (Oron, 2006) and up to 77% (Quirk B J, Sonowal P, Jazayeri M A, Baker J E, Whelan H T. Cardioprotection from ischemia-reperfusion injury by near-infrared light in rats. *Photomed Laser Surg.* 2014; 32(9):505-511. doi:10.1089/pho.2014.3743). In myocardial ischemia-reperfusioninjury, "Nicotinamide adenine dinucleotide phosphate (NADPH) oxidase, along with other elements of the mitochondrial electron transport chain (ETC), have been reported to be primary sources of ROS [reactive oxygen species] production in cardiac tissue." (Id) Excessive ROS can lead to major tissue damage, cell death, and via caspase-3 to apoptosis. (Id). The elevated PEDF (as much as 33-fold within 24 hours) with its anti-oxidant properties observed after laser may suppress the p22phox subunit of NADPH oxidase acutely and sufficiently (as noted in VEGF-exposed U266 myeloma cells, (Seki R, Yamagishi S, Matsui T, Yoshida T, Torimura T, Ueno T, Sata M, Okamura T. Pigment epithelium-derived factor (PEDF) inhibits survival and proliferation of VEGF-exposed multiple myeloma cells through its anti-oxidative properties. *Biochem Biophys Res Commun.* 2013 Feb. 22; 431(4):693-7. doi: 10.1016/j.bbrc.2013.01.057. Epub 2013 Jan. 31. PMID: 23375814.)) to result in less overall acute ROS production and thus less cardiac tissue damage. This may more than counterbalance the milder increase in ROS from cytochrome c oxidase stimulation by LLLT thus resulting in the significant decreases in infarct sizes after LLLT reported by investigators. It has also been shown that "[T]reatment of a remote tissue with NIr [near infrared] can induce systemic mechanisms that also provide 'indirect' protection of the brain . . . critical tissues such as the brain, heart and lung are protected from stress by remote ischemic preconditioning . . . " (Johnstone D M, el Massri N, Moro C, Spana S, Wang X S, Torres N, Chabrol C, De Jaeger X, Reinhart F, Purushothuman S, Benabid A L, Stone J, and Mitrofanis J. Indirect application of near infrared light induces neuroprotection in a mouse model of parkinsonism—An abscopal neuroprotective effect, *Neuroscience* 2014:274:93-101, 93, 94).).

Therefore, another aspect of this disclosure is a method for ameliorating ischemic heart disease in a subject that includes (i) selecting a patient based on a diagnosis for ischemic heart disease or risk of developing ischemic heart disease; and (ii) responding to the diagnosis by delivering pulsed electromagnetic energy to at least one ocular blood vessel of the patient to ameliorate at least one symptom of ischemic heart disease. In certain embodiments, the pulsed electromagnetic energy comprises electromagnetic energy selected from infrared radiation, near infrared radiation, visible radiation, or other shorter or longer wavelength radiation, and combinations thereof. The treatment can be, for example, any of the pulsed LLLT treatment embodiments described herein.

Liver Disease

LLLT by increasing PEDF may also be able to prevent liver fibrosis from various sources of continuing liver injury which would have led to liver failure. "Both PEDF and the 34-mer [antiangiogenic functional motif (amino acid positions Asp44-Asn77) down-regulated PDGF receptor-$\alpha/\beta$ expression and blocked the PDGF-induced phosphorylation of Akt and ERK . . . Investigation of this 34-mer peptide led to the identification of a signaling mechanism involving PPAR$\gamma$ induction, suppression of Wnt/$\beta$-catenin signaling and down-regulation of the PDGF receptor-$\alpha/\beta$ . . . " (Tsai T-H, Shih S-C, Ho T-C, Ma H-I, Liu M-Y, et al. (2014) Pigment Epithelium-Derived Factor 34-mer Peptide Prevents Liver Fibrosis and Hepatic Stellate Cell Activation through Down-Regulation of the PDGF Receptor. *PLoS ONE* 9(4): e95443. doi:10.1371/journal.pone.0095443) which inhibits myofibroblastic hepatic stellate cells leading to liver fibrosis and ultimately liver failure. "PEDF is expressed in hepatocytes, however, its level is reduced dramatically in the livers of cirrhotic patients." (Id). Furthermore, although LLLT at specific parameters under certain conditions may stimulate Akt and ERK phosphorylation with downstream proliferative effects, this may be modified by adjusting the laser parameters to creating more inhibition of PDGF blockage of this phosphorylation of Akt and ERK by increasing the relative balance of PEDF to create a net balanced effect of inhibition of liver fibrosis and liver failure.

The relative increase of PEDF balance down-regulates PDGF receptor-$\alpha/\beta$ expression, the impedes Akt and ERK phosphorylation that is induced by PDGF, increases PPAR$\gamma$, and suppresses Wnt/$\beta$-catenin signaling (Tsai et al, 2014) which can prevent liver fibrosis and liver failure. Furthermore, targeting the Wnt/$\beta$-catenin pathway has been proposed in cancer therapy as "cross talk between Wnt/$\beta$-catenin and PI3K-AKT pathway was confirmed to promote tumorigenesis and resistance to cancer therapy . . . The deregulation of Wnt/$\beta$-catenin signaling pathway is closely related to the initiation and progression of various types of cancers . . . " (Zhang Y, Wang X. Targeting the Wnt/$\beta$-catenin signaling pathway in cancer. J Hematol Oncol. 2020 Dec. 4; 13(1):165. doi: 10.1186/s13045-020-00990-3. PMID: 33276800; PMCID: PMC7716495.). Inhibitors of Wnt ligand/receptor interface and Wnt/FZD antagonists have anti-tumor effects. (Id.). Additionally, PEDF (which is increased by LLLT) is expressed in the heart and eye as well as in the liver may also reduce myocardial scarring after myocardial infarction (Oron, 2006) and help abrogate scarring in the retina after phase I and III of this subthreshold micropulse PULSAR™ laser methodology in AMD treatment.

Therefore, another aspect of this disclosure is a method for ameliorating liver disease in a subject that includes (i) selecting a patient based on a diagnosis for liver disease or risk of developing liver; and (ii) responding to the diagnosis by delivering pulsed electromagnetic energy to at least one ocular blood vessel of the patient to ameliorate at least one symptom of liver disease. In certain embodiments, the pulsed electromagnetic energy comprises electromagnetic energy selected from infrared radiation, near infrared radiation, visible radiation, or other shorter or longer wavelength radiation, and combinations thereof. The treatment can be, for example, any of the pulsed LLLT treatment embodiments described herein.

COVID-19

It has also been demonstrated that LLLT/PBM with low energy 810 nm laser phosphorylates IKK$\alpha/\beta$ (inhibitor of kappa B kinase-$\alpha/\beta$) and the transcription factor NF-kB, in addition to increasing ROS and ATP. The global pandemic COVID-19 is a contagious disease and its mortality rates ranging from 1% to 5% are likely due to acute respiratory distress syndrome (ARDS), and cytokine storm. Researchers worldwide are in search of anti-inflammatory medicines in the hope of finding a cure for COVID-19. "Low-level laser therapy (LLLT) has strong, anti-inflammatory effects confirmed by meta-analyses, and it may be therapeutic to ARDS. LLLT has been used for . . . [multiple] health conditions . . . for decades . . . Based on the clinical experience, peer-reviewed studies, and solid laboratory data . . . , LLLT attenuates cytokine storm at multiple levels and reduces the major inflammatory metabolites. LLLT is a safe, effective, low-cost modality without any side-effects that may be combined with conventional treatment of ARDS." (Mokmeli, Soheila and Vetrici, Mariana. Low level laser therapy as a modality to attenuate cytokine storm at multiple levels, enhance recovery, and reduce the use of ventilators in COVID-19. *Can J Respir Ther.* 2020; 56: 25-31, 25.)

Therefore, another important aspect of this disclosure is a method for ameliorating respiratory distress syndrome in a subject that includes (i) selecting a patient based on a diagnosis for COVID-19 or risk of developing respiratory distress syndrome; and (ii) responding to the diagnosis by delivering pulsed electromagnetic energy to at least one ocular blood vessel of the patient to ameliorate at least one symptom of respiratory distress syndrome or COVID-19. In certain embodiments, the pulsed electromagnetic energy comprises electromagnetic energy selected from visible light radiation, infrared radiation, near infrared radiation, visible radiation, or other shorter or longer wavelength radiation, and combinations thereof. The treatment can be, for example, any of the pulsed LLLT treatment embodiments described herein.

Bone Healing

Ates et al. reported in 2018 that, "Photobiomodulation (PBM) and photodynamic therapy (PDT) share similar mechanisms but have opposite aims. Increased levels of reactive oxygen species (ROS) in the target tissue in response to light combined photosensitizer (PS) application may lead to cell proliferation or oxidative damage depending on the ROS amount . . . A diode laser irradiating at 809 nm (10 W output power, 50 mW/cm$^2$ power density) was used at 0.5, 1, and 2 J/cm$^2$ energy densities (10, 20, and 40 s respectively) was applied following ICG incubation. No inhibitory effect was observed in cell viability and proliferation . . . ICG-mediated PBM did not alter cell viability but increased ALP [alkaline phosphatase] activity and enhanced mineralization of existing osteoblasts . . . PS can be combined to PBM not only to damage the malignant cells as aimed in PDT studies, but also to promote cellular activity . . . ICG-mediated PBM can have promising outcomes in bone healing and regeneration therapies in future." (Ates G B, Ak A, Garipcan B, Gilso M. Indocyanine green-mediated photobiomodulation on human osteoblast cells. *Lasers Med Sci.* 2018 September; 33(7):1591-1599).

Another aspect of this disclosure is a method for enhancing bone healing in a subject that includes (i) selecting a patient based on a need for bone healing; and (ii) responding to the diagnosis by delivering pulsed electromagnetic energy to at least one ocular blood vessel of the patient to enhance bone healing. In certain embodiments, the pulsed electromagnetic energy comprises electromagnetic energy selected from visible light radiation, infrared radiation, near infrared radiation, visible radiation, or other shorter or longer wavelength radiation, and combinations thereof. The treatment can be, for example, any of the pulsed LLLT treatment embodiments described herein.

Use of ICG Dye or Other Photon Absorption Enhancer with LLLT Treatment.

While the pulsed LLLT treatments described herein can be administered to a patient without any prior administration of agents to assist with or enhance absorption of electromagnetic energy, in some embodiments a photon absorption enhancer is delivered to a patient prior to administration of a pulsed LLLT treatment. Thus, in another aspect of this disclosure, a treatment method includes, before delivering the electromagnetic energy to the patient's eye tissues, administering a photon absorption enhancer to the patient. In one embodiment, the photon absorption enhancer is a photosensitive dye, such as, for example, and without limitation, indocyanine green dye (ICG) or fluorescein dye. In some preferred embodiments, referred to herein as "ICG-mediated LLLT treatment," the photon absorption enhancer is ICG dye. In some preferred embodiments, the dye is administered intravenously. On advantage of "ICG-mediated LLLT treatment" is that the ICG dye can be used to serve two important functions, namely, to assist with visualization of ocular blood vessels, which aids the delivery of electromagnetic energy directly to the ocular blood vessels, and as a therapeutic agent to enhance absorption of photons from the laser beam and/or from the visible aiming beam.

Furthermore, without intending to be limited to any theory, it is believed that the ICG photosensitive dye also functions as an energy transporting/transferring molecule involved in mediating the effects of LLLT treatment. Laser-excited ICG molecules acting as hematogenous chromophores can be transported as photonic energy along with different levels of ROS to local and distant tissues as a result of direct treatment to the choroidal or retinal vasculature at the time of treatment which can be performed even hours after ICG injection. ICG dye is a potent chromophore for infrared radiation with a broad absorption range between 600 to 900 nm, which includes both the diode 650 nm aiming laser and the 810 nm wavelength laser beam, as indicated in the specifications of one of the lasers that can be used, the Iridex OcuLight SLx micropulse laser. This can result in photodynamic effects from the intravenous ICG. As discussed above, research shows that "ICG blood clearance is biphasic" and ICG fluorescence can be detected at least 2 hours after injection (Mordon S; Devoisselle J M; Soulie-Begu S and Desmettre T. Indocyanine Green: Physicochemical Factors Affecting Its Fluorescence in Vivo. *Microvascular Research* 1998; 55, 146-152). It has been proposed that there is selective fixation of ICG on the vessel wall of CNV (choroidal neovascularization) compared to normal choroidal vessels.

Spectral evidence of wavelength shifts in later ICG fluorescence intensity "could be due to a localization of ICG molecules at sites more hydrophobic than serum proteins" and propose these sites "could be either the endothelial wall or white cells such as leukocytes . . . The amphiphilic properties of ICG are consistent with binding of some ICG molecules on sites other than plasmatic proteins after injection." (Mordon et al, 1998). Thus, ICG may localize or accumulate on the vascular endothelium or on leukocytes over time and thus contribute to a selective localized photodynamic effect and to systemic effects respectively. The former process would require even less laser energy to be used to cause sufficient 15% reduction in vessel diameter resulting in MNV closure in the specific situation for neovascularization in AMD.

When ICG is used as a photon absorption enhancer, immediate LLLT treatment after an IV bolus of ICG is not necessary but can be delayed and yet have photodynamic effect since visibly detectable ICG can remain several hours later despite relatively rapid liver clearance. Research has demonstrated both that serum levels of ICG and ICG fluorescence can be detected for at least 120 minutes after IV injection (Mordon et al, 1998). In abdominal surgery, physical detection is possible up to 6 hours after IV injection. (Boni L, David G, Mangano A, et al. Clinical applications of indocyanine green (ICG) enhanced fluorescence in laparoscopic surgery. *Surg Endosc* 2015: 29:2046-2055). Also, "humans can detect IR at wavelengths longer than 1,000 nm" up to 1355 nm (Palczewska et al, 2014). Thus, the diagnostic technique is capable of identifying abnormal ICG fluorescence (peak shifts to 826 nm at 120 minutes) (Mordon et al, 1998) and any delayed phosphorescence under direct visualization with the enhanced sensitivity up to 1,000,000-fold under dark adaptation (maximal after 20-30 minutes) with the contact lens in place. This is possible even up to at least 2 hours or even longer after injection because "ICG blood clearance is biphasic" (Mordon et al, 1998).

Combination Therapies

Compositions and methods of the invention may be administered in combination with any standard therapy known in the art. For example, as discussed above, the present disclosure contemplates that, when treating a patient who has been diagnosed with cancer, the LLLT treatment described herein may be combined as an adjunct with other standard treatments for cancer, such as chemotherapy, radiotherapy, and the like.

In another embodiment, an LLLT treatment as described herein is administered together with an agent that promotes the recruitment, survival, proliferation or transdifferentiation of a stem cell (e.g., a hematopoietic stem cell). Such agents include, for example, collagens, fibronectins, laminins, integrins, angiogenic factors, anti-inflammatory factors, glycosaminoglycans, antibodies and fragments thereof, functional equivalents of these agents, and combinations thereof.

Maintenance of Physiological Homeostasis

In yet another aspect of this disclosure, there are provided methods for treating a human being for maintenance of good health and/or as an aid to preventing age-related tissue degeneration. Optimal functioning of a human being or other living organism is affected by many variables, such as body temperature and fluid balance, being kept within certain pre-set limits (homeostatic range). Other variables include the pH of extracellular fluid, the concentrations of sodium, potassium and calcium ions, as well as that of the blood sugar level, and these need to be regulated despite changes in the environment, diet, or level of activity. Each of these variables is controlled by one or more regulators or homeostatic mechanisms, which together maintain life. The metabolic processes of all organisms can only take place in very specific physical and chemical environments. The conditions vary with each organism, and with whether the chemical processes take place inside the cell or in the interstitial fluid bathing the cells. The best known homeostatic mechanisms in humans and other mammals are regulators that keep the composition of the extracellular fluid (or the "internal environment") constant, especially with regard to the temperature, pH, osmolality, and the concentrations of sodium, potassium, glucose, carbon dioxide, and oxygen. However, a great many other homeostatic mechanisms, encompassing many aspects of human physiology, control other entities in the body.

A wide variety of factors can cause a person or other living organism to have suboptimal health, such as disease, injury, inflammation, aging, malnutrition, inadequate hydration and inadequate exercise, to name a few. Often, such factors result in progressive and increasing deviations of biological processes from homeostasis, and thus deviations from normal biological function. The normal state of health of maintained by complex physiologic processes of constant surveillance for and repair of defective proteins and potential threats, such as bacteria, viruses and neoplasia. These normal physiologic processes and their actions are ideal as good health and function is the result of their normal function. While the normal function of these physiological processes are ideal, such homeostatic processes themselves are not always perfectively effective. Potential threats and abnormalities may either escape detection or exceed the ability for repair. Failure of surveillance and response may result from any number of reasons, including disease causing immunosuppression, evasion of detection by hiding of antigenic stimuli, such as occurring in certain cancers and retroviruses, and the onset and progression below the level of symptoms recognition and activation.

Without intending to be limited to any theory whereby the present invention achieves its advantageous results, it is believed that LLLT treatments as described herein stimulate production of biological factors or repairing abnormal cell proteins, to promote a return to homeostasis and normalize cell function. Agnostic to the cause of protein misfolding and consequent cellular dysfunction, LLLT treatment is thus a non-specific trigger of disease-specific repair.

In another aspect of this disclosure, there is provided a method for improving the health or suppressing age-related tissue generation in a subject that includes (i) selecting a patient having a need for improved overall health; and (ii) responding to the need by delivering pulsed electromagnetic energy to at least one ocular blood vessel of the patient. In certain embodiments, the pulsed electromagnetic energy comprises electromagnetic energy selected from infrared radiation, near infrared radiation, visible radiation, or other shorter or longer wavelength radiation, and combinations thereof. The treatment can be, for example, any of the pulsed LLLT treatment embodiments described herein.

As the invention has been shown to be an effective treatment for a number of non-ocular diseases, disorders or conditions without adverse treatment effects, and by virtue of its safety and effectiveness, it can also be used to treat a non-ocular disease, disorder or condition or delay the onset of symptoms of a non-ocular disease, disorder or condition prophylactically or as a preventative treatment for such disease, disorder or condition. Any treatment that improves biological function, and thus health, should also reduce disease severity, progression and untoward events. By beginning treatment early, prior to pathologic structural change, and maintaining the treatment benefit by regular functionally-guided re-treatment, structural and functional degeneration might thus be delayed if not prevented. Even modest early reductions in the rate of disease progression may lead to significant long-term reductions and complications. By mitigating the consequences of the primary defect, the course of disease may be muted, progression slowed, and complications reduced.

Further reference is made to the following experimental examples. The examples are given for the purpose of illustrating various embodiments of the invention and are not meant to limit the present invention in any fashion. The present examples, along with the methods described herein are presently representative of preferred embodiments, are provided only as examples, and are not intended as limitations on the scope of the invention. Changes therein and other uses which are encompassed within the spirit of the invention as defined by the scope of the claims will occur to those skilled in the art.

EXAMPLES

All of the patients discussed in the following examples were administered pulsed LLLT treatments delivered directly into the vasculature of one or both eyes, usually multiple times spaced apart one or more months. The LLLT treatments were administered specifically to treat eye diseases, but were later discovered to also produce remarkable results relating to concurrent non-ocular medical conditions, which were improved significantly or even "cured" through the LLLT treatments.

Example 1

Treatment of a Diabetes Mellitus Patient with Pulsed LLLT

Patient #1 had long been treated for insulin-dependent diabetes mellitus, ultimately requiring 300 units of insulin a day via an insulin pump. She was treated with pulsed LLLT for bilateral diabetic retinopathy and early wet AMD multiple times over a period of years with improved vision in both eyes. Later, it was learned that her insulin dependence had completely disappeared, and her pancreas began to produce endogenous insulin documented by laboratory testing for the first time after some 50 years to the great surprise of her endocrinologists. This is so rare that she may be only one of a handful of such cases out of the many millions of diabetics in the world. She no longer required any exogenous insulin to her great delight.

Example 2

Treatment of a Diabetes Mellitus Patient with Pulsed LLLT

Patient #2 had been treated for non-insulin dependent diabetes for multiple decades and had received pulsed LLLT treatments to both eyes months apart, over several years, guided by fluorescein angiography specifically to include the vascular microaneurysms and other vascular anomalies, but usually without a grid pattern and using micropulse throughout all phases, with gradually increasing power over time during the session. After multiple pulsed LLLT treatments, his hemoglobulin A1C had markedly improved and his oral diabetic medications had stopped to the pleasant surprise of his doctors. His diabetes mellitus is now diet-controlled after many years of being on oral hypoglycemic agents.

Example 3

Treatment of a Diabetes Mellitus Patient with Pulsed LLLT

Patient #3 had long been treated for diabetes mellitus with retinopathy and neuropathy was treated with pulsed LLLT treatments for diabetic retinopathy multiple times over several years to address vascular anomalies in both eyes. Patient #3 not only reported better vision after the pulsed LLLT treatment but also much better glucose control, pain relief and return of the lost sensation from neuropathy, all of which required less medications.

Example 4

Treatment of a Cancer Patient with Pulsed LLLT

Patient #4 had been treated for squamous cell carcinoma of the tongue by surgical excision and reconstruction involving the larynx with a 95% chance of recurrence within one year. Pulsed LLLT treatment was performed bilaterally via the ocular route multiple times initially for wet AMD and later for clinically significant diabetic retinopathy. Patient #4 reported "feeling good" with better vision after every laser treatment and is documented to have improved Snellen visual acuity in both eyes. Patient #4 continuously asked for more laser at virtually every visit because she was so pleased that the laser helped improve her vision almost immediately after each treatment. At last follow-up, seven years after her surgery, she did not have any recurrence of her squamous carcinoma to the great and pleasant surprise of her oncologists.

Example 5

Treatment of a Cancer Patient with Pulsed LLLT

Patient #5 underwent treatment for kidney cancer and had a negative prognosis. He received multiple pulsed LLLT treatments for background diabetic retinopathy directly targeting vascular anomalies such as microaneurysms, with gradually increasing fluence until a minimal reaction in the wall of the vascular lesions, in addition to a grid pattern. In addition to improved vision, patient #4's kidney cancer also improved and did not progress to the surprise of his oncologists.

Example 6

Treatment of a Multiple Sclerosis Patient with Pulsed LLLT

Patient #6, a former nurse, had been treated for debilitating symptomatic multiple sclerosis for multiple decades, which condition failed to improve after multiple diverse treatment protocols, even including cancer chemotherapy agents. She was treated with pulsed LLLT treatments (similar to Phase II) for retinal breaks in the retinal periphery but with Phase I and Phase III provided directly to the choroidal circulation in the periphery. In addition to the retinal breaks being successfully treated, she also reported that her multiple sclerosis symptoms disappeared almost immediately that same afternoon. She remained symptom free from her multiple sclerosis for many months. Sometime later, she returned again with multiple sclerosis symptoms and requested another laser treatment. The pulsed LLLT treatment was applied again and once again her multiple sclerosis symptoms completely disappeared almost immediately, again that same afternoon.

Example 7

Treatment of a Heart Disease Patient with Pulsed LLLT

Patient #7 was being treated for heart disease and had suffered a heart attack. His doctors were concerned that he would have eventually have fatal cardiac complications leading to heart failure and arrhythmia. He underwent pulsed LLLT treatments multiple times for wet AMD and to his cardiologists' surprise, his cardiac function subsequently improved with an amazing unexplained improvement in cardiac function as measured by a remarkably improved ejection fraction (a critical index measurement in heart failure).

Example 8

Treatment of Hypertensive Patients with Pulsed LLLT

Multiple patients that had been diagnosed with hypertension and either diabetic retinopathy from long-standing diabetes mellitus or symptomatic "subclinical" neovascular AMD who were treated multiple times over months to years with ocular delivery of pulsed LLLT to the retinal or choroidal vasculature not only reported improved vision but also better blood pressure control with either elimination or reduction of antihypertensive medications.

Example 9

Treatment of Patients with Arthritis or Chronic Pain with Pulsed LLLT

Multiple patients that had been diagnosed with arthritis and/or that were suffering from lower back pain and either diabetic retinopathy from long-standing diabetes mellitus or symptomatic "subclinical" neovascular AMD who were treated multiple times over months to years with ocular delivery of pulsed LLLT to the retinal or choroidal vasculature not only reported improved vision but also reduced arthritis symptoms and improved pain control with either elimination or reduction of anti-arthritis or pain medications.

While embodiments of the present disclosure have been described herein, it is to be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

As will be appreciated from the descriptions herein, a wide variety of aspects and embodiments are contemplated by the present disclosure, examples of which include, without limitation, the aspects and embodiments listed below:

What is claimed is:
1. A method for ameliorating a non-ocular disease/disorder in a subject, comprising:

selecting a patient based on a diagnosis for a non-ocular disease/disorder;

responding to the diagnosis by delivering pulsed electromagnetic energy to at least one ocular blood vessel of the patient to ameliorate at least one symptom of the non-ocular disease/disorder; wherein delivering pulsed electromagnetic energy comprises administering a pulsed low level laser/light therapy (LLLT); wherein the pulsed LLLT treatment comprises stimulating the ocular blood vessel with a sub-threshold laser treatment; and wherein the electromagnetic energy has a wavelength of from about 380 nm to about 11,000 nm; and applying a second dose of electromagnetic energy at one or more different wavelengths wherein the second dose of electromagnetic energy has one or more wavelengths of from about 193 nm to about 1 mm.

2. The method of claim 1 wherein the pulsed electromagnetic energy comprises electromagnetic energy selected from infrared radiation, near infrared radiation, visible light radiation and combinations thereof.

3. The method of claim 1 wherein the at least one ocular blood vessel comprises a member selected from the group consisting of a retinal blood vessel, a choroidal blood vessel and combinations thereof.

4. The method of claim 1 wherein the at least one ocular blood vessel comprises a member selected from the group consisting of a neuroretinal cell, a serum component, a blood cell, a lymphatic cell, an immune cell or a component thereof, an extracellular molecule, an atom, an ion, and combinations thereof.

5. The method of claim 3 wherein the choroidal blood vessel comprises a choroidal feeding vessel.

6. The method of claim 3 wherein the choroidal blood vessel comprises a choroidal draining vessel.

7. The method of claim 1 wherein the method reduces at least one symptom of the non-ocular disease/disorder.

8. The method of claim 1 wherein the non-ocular disease/disorder is selected from the group consisting of cancer, breast cancer related lymphedema, heart disease, hypertension, metabolic/endocrine disorders, diabetes mellitus, diabetic foot ulcers, diabetic neuropathy, cerebrovascular disorders, spinal cord injuries, obesity, dyslipidemia, liver disease, renal disease, traumatic brain injury, dermatologic disorders, onychomycosis, infections including fungal, drug-resistant infections, microbiome related disorders, immune/complement system disorders, dental disorders, oral mucositis, memory disorders, psychiatric disorders, musculoskeletal disorders, bone disorders, osteoporosis, neurodegenerative diseases, excess subcutaneous adiposity, wound healing, poor exercise performance issues, sperm motility and velocity issues, chronic pain, inflammatory disorders, pulmonary disorders, and other degenerative aging disease or other systemic disorders or such disorder(s) one may be at increased risk of developing.

9. The method of claim 1 wherein the pulsed LLLT treatment has predetermined laser parameters selected from the group consisting of laser manufacturer and type, wavelength and frequency, duty cycle, mode, power, irradiance/power density, fluence/energy density, beam profile, spot size, spot number, laser target and laser pattern, short and ultra-short pulse and envelope on durations and off intervals, repeat and off intervals and durations, pulse train duration and envelope duration, pulse and repetition frequency, envelope and pulse train frequency, dosing frequency, session frequency, ocular delivery device, type of contact lens and lubricating ointment for ocular delivery.

10. The method of claim 9 wherein the pulsed energy parameters are selected and applied to the ocular blood vessel to cause resonant or nonresonant light/phonon/photon interactions with molecules/matter within and/or around the ocular blood vessel or ocular tissue.

11. The method of claim 1 wherein the electromagnetic energy has a wavelength of from about 600 nm to about 1100 nm.

12. The method of claim 1 wherein the first wavelength is about 650 nm and wherein the second wavelength is about 810 nm.

13. The method of claim 1 wherein the sub-threshold laser treatment comprises a duty cycle of from about 0.4% to about 100%.

14. The method of claim 1 wherein the sub-threshold laser treatment comprises a duty cycle of from about 2% to about 25%.

15. The method of claim 1 wherein the sub-threshold laser treatment comprises a power of from about 50 mW to about 2000 mW.

16. The method of claim 1 wherein the sub-threshold laser treatment comprises an irradiance of from about 0.059 $W/cm^2$ to about 63,000 $W/cm^2$.

17. The method of claim 1 wherein the sub-threshold laser treatment comprises an energy density of from about 0.024 $J/cm^2$ to about 150 $J/cm^2$ per laser beam.

18. The method of claim 1 wherein the sub-threshold laser treatment comprises a pulse duration of no greater than about 1 ms.

19. The method of claim 1 wherein a micropulse from a laser delivers the pulsed electromagnetic energy.

20. The method of claim 19 wherein the micropulse has a duration of from about 0.1 milliseconds to about 1.0 milliseconds.

21. The method of claim 1 wherein the sub-threshold laser treatment comprises a pulse interval of from about 1.0 ms to about 10.0 ms.

22. The method of claim 1 wherein the method comprises, before delivering the pulsed electromagnetic energy, injecting a dye or other medication, a nanoparticle material, or a biologic material intravenously into the subject.

23. The method of claim 22 wherein the dye is selected from the group consisting of indocyanine green, fluorescein and verteporfin.

* * * * *